US010407737B2

(12) United States Patent
Cohen et al.

(10) Patent No.: US 10,407,737 B2
(45) Date of Patent: Sep. 10, 2019

(54) METHODS AND KITS FOR IDENTIFYING PRE-CANCEROUS COLORECTAL POLYPS AND COLORECTAL CANCER

(71) Applicant: BIO-MARCARE TECHNOLOGIES LTD., Jerusalem (IL)

(72) Inventors: Dana Cohen, Lapid (IL); Vardit Moshayoff, Jerusalem (IL); Ouriel Faktor, Rehovot (IL)

(73) Assignee: BIO-MARCARE TECHNOLOGIES LTD., Jerusalem (IL)

( * ) Notice: Subject to any disclaimer, the term of this patent is extended or adjusted under 35 U.S.C. 154(b) by 0 days.

(21) Appl. No.: 15/300,859

(22) PCT Filed: Apr. 2, 2015

(86) PCT No.: PCT/IL2015/050362
§ 371 (c)(1),
(2) Date: Sep. 30, 2016

(87) PCT Pub. No.: WO2015/155765
PCT Pub. Date: Oct. 15, 2015

(65) Prior Publication Data
US 2017/0058357 A1 Mar. 2, 2017

Related U.S. Application Data

(60) Provisional application No. 61/977,636, filed on Apr. 10, 2014.

(51) Int. Cl.
| | | |
|---|---|---|
| *C07H 21/04* | (2006.01) | |
| *C12Q 1/68* | (2018.01) | |
| *C12Q 1/6886* | (2018.01) | |
| *A61K 31/513* | (2006.01) | |
| *A61K 31/519* | (2006.01) | |
| *A61K 31/555* | (2006.01) | |
| *A61K 31/7068* | (2006.01) | |

(52) U.S. Cl.
CPC .......... *C12Q 1/6886* (2013.01); *A61K 31/513* (2013.01); *A61K 31/519* (2013.01); *A61K 31/555* (2013.01); *A61K 31/7068* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2005/0014165 A1 | 1/2005 | Lee et al. |
| 2005/0048494 A1 | 3/2005 | Wang |
| 2007/0010469 A1 | 1/2007 | Chan et al. |
| 2007/0037159 A1* | 2/2007 | Sugiura ................. A61K 31/00 435/6.11 |
| 2010/0330079 A1 | 12/2010 | Ruegg |
| 2012/0329077 A1 | 12/2012 | Markowitz |

FOREIGN PATENT DOCUMENTS

| | | |
|---|---|---|
| CN | 103667437 | 3/2014 |
| JP | 2006101701 A | 4/2006 |
| JP | 2009528061 A | 8/2009 |
| JP | 2009528825 A | 8/2009 |
| JP | 2011512332 A | 4/2011 |
| WO | 02/058534 | 8/2002 |
| WO | 2004/106515 | 12/2004 |
| WO | 2011012136 | 2/2011 |
| WO | 2012103250 | 8/2012 |
| WO | 2012149609 A1 | 11/2012 |
| WO | 2013/110817 | 8/2013 |

OTHER PUBLICATIONS

Wen et al. Neurourol Urodyn, vol. 30, No. 8, pp. 1627-1632, Nov. 2011 (Year: 2011).*
Jee et al. Cell Cycle, vol. 9, pp. 4703-4710, Dec. 2010 (Year: 2010).*
Mohammed et al. (Oncology Letters, vol. 2, pp. 719-724, 2011 (Year: 2011).*
Hoshikawa et al. Physiol Genomics, vol. 12, pp. 209-219 (2003) (Year: 2003).*
Bandrés et al., (2007). A gene signature of 8 genes could identify the risk of recurrence and progression in Dukes' B colon cancer patients. Oncology reports, 17(5), 1089-1094.
Chao et al., (2013) Blood RNA biomarker panel detects both left- and right-sided colorectal neoplasms: a case-control study. J Exp Clin Cancer Res 23;32: 44.
Chen et al., (2008) Characterization of microRNAs in serum: a novel class of biomarkers for diagnosis of cancer and other diseases. Cell research, 18(10), 997-1006.
Collado et al., (2007) Genomic profiling of circulating plasma RNA for the analysis of cancer. Clinical chemistry, 53(10), 1860-1863.
Coskun et al., (2012) MicroRNAs in inflammatory bowel disease-pathogenesis, diagnostics and therapeutics. World J Gastroenterol, 18(34), 4629-4634.
Cunningham et al., (2010) Colorectal cancer. Lancet 20;375(9719):1030-47.
Ganepola et al., (2010) Gene expression profiling of primary and metastatic colon cancers identifies a reduced proliferative rate in metastatic tumors. Clinical & experimental metastasis, 27(1), 1-9.
Ganepola et al., (2014) Use of blood-based biomarkers for early diagnosis and surveillance of colorectal cancer. World J Gastrointest Oncol, 6(4), 83-97.

(Continued)

*Primary Examiner* — Jeanine A Goldberg
(74) *Attorney, Agent, or Firm* — The Roy Gross Law Firm, LLC; Roy Gross

(57) ABSTRACT

Methods and kits for identifying a subject having pre-cancerous advanced polyps or colorectal cancer based on the expression profile(s) of specific mRNA biomarkers. Methods and kits for diagnosing, preventing, managing therapy, monitoring and identifying predisposition to colorectal cancer.

5 Claims, 11 Drawing Sheets
Specification includes a Sequence Listing.

(56) References Cited

OTHER PUBLICATIONS

Garcia et al., (2009) Extracellular tumor-related mRNA in plasma of lymphoma patients and survival implications. PloS one, 4(12), e8173.

Gonzalo et al., (2013) Gene expression profiling of serrated polyps identifies annexin A10 as a marker of a sessile serrated adenoma/polyp. The Journal of pathology, 230(4), 420-429.

Marshall et al., (2010) A blood-based biomarker panel for stratifying current risk for colorectal cancer. International Journal of Cancer, 126(5), 1177-1186.

Mohammed et al., (2011). EPAS1 mRNA in plasma from colorectal cancer patients is associated with poor outcome in advanced stages. Oncology letters, 2(4), 719-724.

Notterman et al., (2001) Transcriptional gene expression profiles of colorectal adenoma, adenocarcinoma, and normal tissue examined by oligonucleotide arrays. Cancer research, 61(7), 3124-3130.

Quintero et al., (2012) Colonoscopy versus fecal immunochemical testing in colorectal-cancer screening. New England Journal of Medicine, 366(8), 697-706.

Shen et al., (2013) MicroRNAs as potential biomarkers in human solid tumors. Cancer letters, 329(2), 125-136.

Silva et al., (2002) Detection of epithelial tumour RNA in the plasma of colon cancer patients is associated with advanced stages and circulating tumour cells. Gut, 50(4), 530-534.

Silva et al., (2002) RNA is more sensitive than DNA in identification of breast cancer patients bearing tumor nucleic acids in plasma. Genes, Chromosomes and Cancer, 35(4), 375-376.

Xu et al., (2013) Gene expression analysis of peripheral blood cells reveals toll-like receptor pathway deregulation in colorectal cancer. PloS one, 8(5), e62870.

International Search Report for PCT/IL2015/050362 Completed Jun. 18, 2015; dated Jun. 22, 2015 4 pages.

Written Opinion for PCT/12015/050362 Completed Jun. 18, 2015; dated Jun. 22, 2015.

Kim et al., (2011) Genetic and expressional alterations of CHD genes in gastric and colorectal cancers. Histopathology 58(5): 660-8.

* cited by examiner

METHODS AND KITS FOR IDENTIFYING PRE-CANCEROUS COLORECTAL POLYPS AND COLORECTAL CANCER

This application is a 35 U.S.C. § 371 national phase application of PCT/IL2015/050362, filed Apr. 2, 2015, which claims priority to U.S. 61/977,636 filed on Apr. 10, 2015. Both applications are incorporated herein by reference as if fully set forth.

FIELD OF THE INVENTION

The present invention relates, according to some embodiments, to methods and kits for identifying a subject having pre-cancerous advanced polyps or colorectal cancer based on the expression profile(s) of specific mRNA biomarkers. The present invention further comprises methods and kits for diagnosing, preventing, managing therapy, monitoring and identifying predisposition to colorectal cancer.

BACKGROUND OF THE INVENTION

Colorectal cancer (CRC) is one of the most common cancers accounting for approximately 10% of all cancer cases and approximately 8% of all cancer deaths. Solid cancers are normally diagnosed based on a histo pathological tissue evaluation, where the gold standard for CRC is fiber-optic colonoscopy. This technology is labor intensive, time consuming, costly and extremely invasive. The alternative of fecal occult blood test (FOBT), while not as invasive, is known to suffer from low sensitivity.

Screening and monitoring assays are essential for early detection and management of cancer. Blood-based tests enable large-scale screening of clinically asymptomatic (supposedly healthy) individuals, for diagnosis, monitoring and prediction of cancer. Furthermore, blood-based sampling is prevalent and convenient, and therefore may increase compliance in asymptomatic populations.

Bonilla et al. (Oncology Letters, 2, 719-714, 2011) disclose mRNA biomarkers associated with poor outcome in patients suffering from advanced stages of colorectal cancer.

Comprehensive lists of hundreds of genes that may be associated with colorectal cancer were disclosed, for example, in Ye et al., Plos one, 2013; 8 (5), e62870; and Garcia et al., Clinical Chem. 53 (10): 1860-1863, 2007. Marshall et al. (Int J Cancer 2010; 126: 1177-1186) disclose a biomarker for CRC based on RNA extracted from peripheral blood cells corresponding to a panel of seven genes: ANXA3, CLEC4D, LMNB1, PRRG4, TNFAIP6, VNN1 and IL2RB.

US 2010/0330079 discloses a method for the detection of protein biomarkers for early diagnosis and management of colorectal cancer. The method includes obtaining quantitative information about the expression of 51 genes in peripheral blood.

WO 2011/012136 discloses a method for discriminating between CRC and non-cancerous samples based on the expression level of a group of miRNAs.

There is an unmet need for cost-effective, rapid, accurate and minimally invasive methods and kits for early detection and treatment of pre-cancerous advanced polyps and colorectal cancer, with improved sensitivity and specificity.

SUMMARY OF THE INVENTION

The present invention provides methods and kits for identifying colon cancer and precancerous polyps in a subject. Advantageously, the methods and kits of the invention differentiate a colon having precancerous advanced polyps from colorectal cancer, based on a non-invasive molecular based analysis. Moreover, the methods and kits of the invention provide a diagnostic platform with high sensitivity (at least 60%) and high specificity (above 85%).

The present invention is premised on the discovery that disease-associated biomarkers can be identified in plasma or other bodily fluids long before an overt disease is apparent. Another advantage conferred by the biomarkers of the present invention arises from the fact that the biomarkers are extracellular, thereby originate from all body tissues. Moreover, these biomarkers are not affected by the immune response. The presence or absence of these biomarkers from the plasma footprints of patients suffering from colorectal cancer is provided herein as early diagnostic tools, for which treatment strategies can be devised and administered to prevent, delay or reverse the formation of neoplastic colorectal cells. One or combinations of several of the disease-associated biomarkers of the present invention are useful to diagnose subjects suffering from precancerous advanced polyps or colorectal cancer, or advantageously, to diagnose those subjects who are asymptomatic for colorectal cancer.

Surprisingly, as demonstrated herein, the methods of the invention use the expression profile of a finite number of nucleic acid sequences biomarkers to identify a healthy subject, a subject having colorectal cancer and a subject having precancerous advanced polyps. Furthermore, the biomarkers of the invention are identified in plasma specimen, which is remote from the site of disease. Unexpectedly, said plasma based biomarkers provide a differentially expressed gene profile which correlates at high specificity and high sensitivity with the pathology examination report.

According to some embodiments, there is provided a method for identifying a subject having colorectal cancer or precancerous advanced colorectal polyps, the method comprising:

(a) providing a biological sample from a subject;

(b) measuring the expression levels of a biomarker comprising a nucleic acid sequences set forth in SEQ ID NO: 1 in said biological sample; and (c) identifying an expression level of said biomarker above a cutoff value for said biomarker, thereby identifying said subject as having colorectal cancer or precancerous advanced colorectal polyps.

According to some embodiments, said biomarker comprises SEQ ID NO: 1 and further comprises at least one nucleic acid sequences selected from SEQ ID NOs: 2, 3, 5-7, 12 and 17. Each possibility is a separate embodiment of the present invention.

According to some embodiments, said biomarker comprises the nucleic acid sequences set forth in SEQ ID NOs: 1-3, 5-7, 12 and 17 and said subject is identified as having colorectal cancer.

According to some embodiments, said biomarker is consisting of the nucleic acid sequences set forth in SEQ ID NOs: 1-3, 5-7, 12 and 17.

According to some embodiments, said biomarker further comprises the nucleic acid sequences set forth in SEQ ID NOs: 1 and 5 and said subject is identified as having precancerous advanced colorectal polyps.

According to some embodiments, said biomarker is consisting the nucleic acid sequences set forth in SEQ ID NOs: 1 and 5.

According to some embodiments, said biomarker comprises SEQ ID NO: 1 and further comprises at least one nucleic acid sequences selected from SEQ ID NOs: 3, 4, 6 and 14. Each possibility is a separate embodiment of the present invention.

According to some embodiments, said biomarker comprises SEQ ID NOs: 1 and 4 and at least one nucleic acid sequences selected from SEQ ID NOs: 3, 6 and 14. Each possibility is a separate embodiment of the present invention.

According to some embodiments, said biomarker comprises SEQ ID NOs: 1, 3 and 4.

According to some embodiments, said biomarker comprises SEQ ID NOs: 1, 4, 6 and 14.

According to some embodiments, said biomarker comprises SEQ ID NOs: 1, 3, 4 and 14.

According to some embodiments, said biological sample is selected from the group consisting of blood, plasma, saliva, serum or a combination thereof. Each possibility is a separate embodiment of the present invention.

According to some embodiments, said biological sample is plasma extracted from peripheral blood.

According to some embodiments, the biomarker is circulating mRNA.

According to some embodiments, measuring the expression of said biomarker comprises at least one nucleic acid analysis technique selected from: polymerase chain reaction (PCR), quantitative PCR, nucleic acid sequencing technology, restriction digestion, specific hybridization, single stranded conformation polymorphism assays (SSCP) and electrophoretic analysis. Each possibility is a separate embodiment of the present invention.

According to some embodiments, measuring the expression of said biomarker comprises extracting mRNA from the plasma, reverse transcribing said mRNA into cDNA and measuring the expression level of said cDNA using quantitative-PCR.

According to some embodiments, there is provided a method for identifying a subject having colorectal cancer or precancerous advanced colorectal polyps, the method comprising:
 (a) providing a biological sample from the subject;
 (b) measuring the expression levels of a biomarker comprising a nucleic acid sequences set forth in SEQ ID NO: 2 in said biological sample; and
 (c) identifying an expression level of said biomarker above a cutoff value for said biomarker, thereby identifying said subject as having colorectal cancer or precancerous advanced colorectal polyps.

According to some embodiments, said biomarker comprises SEQ ID NO: 2 and further comprises at least one nucleic acid sequences selected from SEQ ID NOs: 1, 3, 5-7, 12 and 17. Each possibility is a separate embodiment of the present invention.

According to some embodiments, there is provided a method for identifying a subject having colorectal cancer or precancerous advanced colorectal polyps, the method comprising:
 (a) providing a biological sample from the subject;
 (b) measuring the expression levels of a biomarker comprising a plurality of nucleic acid sequences, said plurality comprises SEQ ID NO: 1 and at least one nucleic acid sequences selected from SEQ ID NOs: 2, 3, 5-7, 12 and 17 in said biological sample; and
 (c) identifying an expression level of said biomarker above a cutoff value for said biomarker, thereby identifying said subject as having colorectal cancer or precancerous advanced colorectal polyps.

According to some embodiments, there is provided a method for identifying a subject having colorectal cancer or precancerous advanced colorectal polyps, the method comprising:
 (a) providing a biological sample from the subject;
 (b) measuring the expression levels of a biomarker comprising a plurality of nucleic acid sequences, said plurality comprises SEQ ID NOs: 6, 9 and 14; and
 (c) identifying an expression level of said biomarker above a cutoff value for said biomarker, thereby identifying said subject as having colorectal cancer or precancerous advanced colorectal polyps.

According to some embodiments, the method further comprises providing the cutoff value for said biomarker. According to some embodiments, the method further comprises providing the cutoff value for each nucleic acid sequence corresponding to the biomarker. According to some embodiments, the method further comprises providing the cutoff value for the plurality of nucleic acid sequences corresponding to the biomarkers.

According to some embodiments, the method further comprises treating the subject having colorectal cancer or precancerous advanced colorectal polyps.

According to some embodiments, treating comprises at least one of administering a chemotherapeutic agent, performing bowel resection, applying radiation therapy and a combination thereof. Each possibility is a separate embodiment of the present invention.

According to some embodiments, the chemotherapeutic agent is selected from the group consisting of: 5-fluorouraeil, leucovorin, oxaliplatin, capecitabine and a combination thereof. Each possibility is a separate embodiment of the present invention.

According to some embodiments, there is provided a kit for identifying a subject having colorectal cancer, the kit comprising: (a) means for measuring the expression level of a biomarker comprising at least one nucleic acid sequences selected from the group consisting of SEQ ID NO: 1 to 17 in a biological sample obtained from a subject; and (b) means for determining a cutoff value for said at least biomarker or information regarding the cutoff value of said at least one biomarker, wherein an expression level of the at least one biomarker above said cutoff value identifies said subject as having colorectal cancer.

According to some embodiments, the means for measuring the expression levels of said biomarker are at least one oligonucleotide capable of amplifying at least one nucleic acid sequences selected from the group consisting of SEQ ID NO: 1 to 17, at least one oligonucleotide capable of hybridizing to said at least one nucleic acid sequence, a nucleotide primer pair flanking the at least one nucleic acid sequence and a combination thereof.

According to some embodiments, the at least one oligonucleotide capable of hybridizing to said at least one nucleic acid sequence comprises a detectable label.

According to some embodiments, the detectable label produces a signal that correlates with the expression level of said at least one biomarker.

According to some embodiments, the detectable label produces an optical signal.

According to some embodiments, said means is a nucleotide primer pair flanking the at least one nucleic acid sequence and the nucleotide primer pair comprises a detectable label.

According to some embodiments, the kit further comprising instructions of use thereof for identifying a subject having colorectal cancer.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
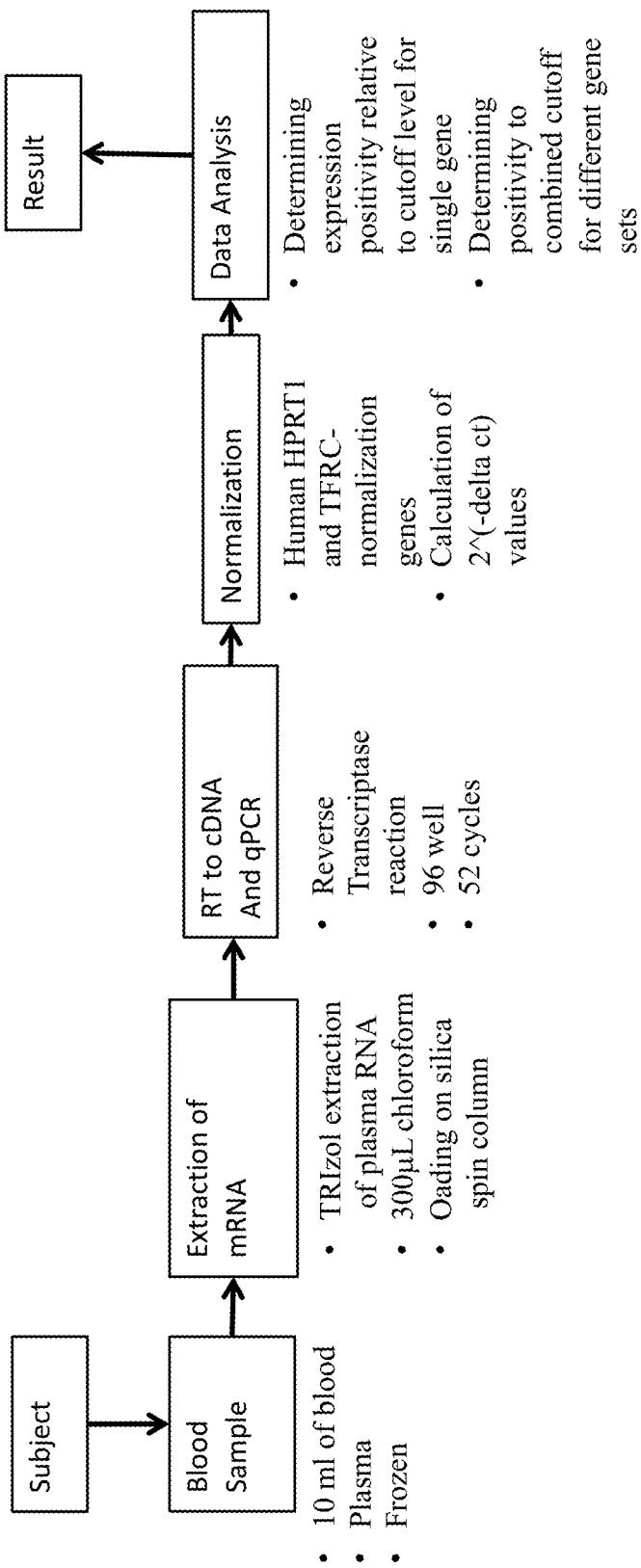
FIG. 1 shows an embodiment of the experimental procedures that are described in the examples below.

The present invention provides biomarkers and combinations thereof, applied for identifying precancerous advanced polyps and colorectal cancer.

The present invention thus concerns biomarkers and biomarker combinations and methods for analyzing plasma biomarkers implicated in precancerous advanced polyps and colorectal cancer. The biomarker of the invention includes one or more mRNA segments corresponding to 17 genes, set forth in SEQ ID NOs: 75-91, or fragments thereof, including the gene fragments set forth in SEQ ID NOs: 1-17.

The disclosed methods, kits, biomarkers and biomarker combinations of the present invention are designed to screen and identify colorectal cancer preferably with sensitivity equals or superior to 60% and specificity equals or superior to 85%.

In general, the methods of the present invention are useful for obtaining biomarker profiles and quantitative information about the expression of many different genes related to diagnosis, including early diagnosis, of precancerous advanced polyps and colorectal cancer in a blood sample.

The level of biomarkers may be measured electrophoretically or immunochemically, wherein the immunochemical detection may be achieved by radioimmunoassay, immunofluorescence assay or by an enzyme-linked immunosorbent assay. In some embodiments, the level of biomarkers is measured by qPCR.

Current molecular diagnostics for CRC have not been sensitive enough to distinguish precancerous advanced polyps from colorectal cancer. About 60% of patients are first diagnosed with late stage disease. Consequently, about $14B are spent annually on treatments and management of CRC patients in the US.

Thus, the diagnostic platform provided herein, offering high specificity and high sensitivity, yet low cost and improved patient compliance, overcomes the deficiencies of the current CRC diagnostics.

According to some embodiments, there is provided a method for identifying a subject having colorectal cancer or precancerous advanced colorectal polyps, the method comprising:

(a) providing a biological sample from a subject;

(b) measuring the expression levels of a biomarker comprising a nucleic acid sequences set forth in SEQ ID NO: 1 in said biological sample; and (c) identifying an expression level of said biomarker above a cutoff value for said biomarker, thereby identifying said subject as having colorectal cancer or precancerous advanced colorectal polyps.

According to some embodiments, there is provided a method for identifying a subject having colorectal cancer or precancerous advanced colorectal polyps, the method comprising:

(a) providing a biological sample from the subject;

(b) measuring the expression levels of a biomarker comprising a nucleic acid sequences set forth in SEQ ID NO: 2 in said biological sample; and (c) identifying an expression level of said biomarker above a cutoff value for said biomarker, thereby identifying said subject as having colorectal cancer or precancerous advanced colorectal polyps.

According to some embodiments, the biomarker comprises the nucleic acid sequence set forth in SEQ ID NO: 3. According to some embodiments, the biomarker comprises the nucleic acid sequence set forth in SEQ ID NO: 4. According to some embodiments, the biomarker comprises the nucleic acid sequence set forth in SEQ ID NO: 5. According to some embodiments, the biomarker comprises the nucleic acid sequence set forth in SEQ ID NO: 6. According to some embodiments, the biomarker comprises the nucleic acid sequence set forth in SEQ ID NO: 7. According to some embodiments, the biomarker comprises the nucleic acid sequence set forth in SEQ ID NO: 8. According to some embodiments, the biomarker comprises the nucleic acid sequence set forth in SEQ ID NO: 9. According to some embodiments the biomarker comprises the nucleic acid sequence set forth in SEQ ID NO: 10. According to some embodiments, the biomarker comprises the nucleic acid sequence set forth in SEQ ID NO: 11. According to some embodiments, the biomarker comprises the nucleic acid sequence set forth in SEQ ID NO: 12. According to some embodiments, the biomarker comprises the nucleic acid sequence set forth in SEQ ID NO: 13. According to some embodiments, the biomarker comprises the nucleic acid sequence set forth in SEQ ID NO: 14. According to some embodiments, the biomarker comprises the nucleic acid sequence set forth in SEQ ID NO: 15. According to some embodiments, the biomarker comprises the nucleic acid sequence set forth in SEQ ID NO: 16. According to some embodiments, the biomarker comprises the nucleic acid sequence set forth in SEQ ID NO: 17.

According to some embodiments, the biomarker comprises a plurality of nucleic acid sequences selected from SEQ ID NO: 1-17. According to some embodiments, the method comprises measuring the expression levels of the biomarker and determining a cutoff value for each nucleic acid sequence selected from SEQ ID NO: 1-17, wherein an expression level of at least one nucleic acid sequence of said plurality above the cutoff value indicates that said subject is having colorectal cancer or precancerous advanced colorectal cancer.

According to some embodiments, said biomarker comprises the nucleic acid sequences set forth in SEQ ID NO: 1 and further comprise at least one of SEQ ID NOs: 2-3, 5-7, 12 and 17 and said subject is identified as having colorectal cancer.

According to some embodiments, said biomarker comprises the nucleic acid sequences set forth in SEQ ID NOs: 1-3, 5-7, 12 and 17 and said subject is identified as having colorectal cancer.

According to some embodiments, said biomarker is consisting of the nucleic acid sequences set forth in SEQ ID NOs: 1-3, 5-7, 12 and 17.

According to some embodiments, said biomarker comprises SEQ ID NO: 1 and SEQ ID NO: 5.

According to some embodiments, said biomarker is consisting of SEQ ID NO: 1 and SEQ ID NO: 5.

According to some embodiments, said biomarker comprises SEQ ID NO: 1 and SEQ ID NO: 3. According to some embodiments, said biomarker comprises SEQ ID NO: 1 and SEQ ID NO: 4. According to some embodiments, said biomarker comprises SEQ ID NO: 1 and SEQ ID NO: 6. According to some embodiments, said biomarker comprises SEQ ID NO: 1 and SEQ ID NO: 14. According to some embodiments, said biomarker comprises SEQ ID NO: 1, SEQ ID NO: 3 and SEQ ID NO: 4. According to some embodiments, said biomarker comprises SEQ ID NO: 1, SEQ ID NO: 3 and SEQ ID NO: 6. According to some embodiments, said biomarker comprises SEQ ID NO: 1, SEQ ID NO: 3 and SEQ ID NO: 14. According to some embodiments, said biomarker comprises SEQ ID NO: 1, SEQ ID NO: 3, SEQ ID NO: 6 and SEQ ID NO: 14. According to some embodiments, said biomarker comprises SEQ ID NO: 1, SEQ ID NO: 4 and SEQ ID NO: 6. According to some embodiments, said biomarkers comprise SEQ ID NO: 1, SEQ ID NO: 4, SEQ ID NO: 6 and SEQ ID NO: 14. According to some embodiments, said biomarker comprises SEQ ID NO: 1, SEQ ID NO: 6 and SEQ ID NO: 14. According to some embodiments, said biomarker comprises SEQ ID NO: 6 and SEQ ID NO: 9. According to some embodiments, said biomarker comprises SEQ ID NO: 6 and SEQ ID NO: 14. According to some embodiments, said biomarker comprises SEQ ID NO: 9 and SEQ ID NO: 14. According to some embodiments, said biomarker comprise SEQ ID NO: 6, SEQ ID NO: 9 and SEQ ID NO: 14. According to some embodiments, said biomarker is consisting of any of the aforementioned combinations.

According to some embodiments, the present invention provides a method for identifying a subject having precancerous advanced colorectal polyps comprising: obtaining a biological sample from the subject; measuring the expression levels a biomarker comprising at least one nucleic acid sequence selected from the group set forth in SEQ ID NO: 1 to 17 (Table 1B) in said biological sample; and determining an expression level of said at least one nucleic acid sequence above its cutoff value thereby identifying the subject as having pre-cancerous advanced colorectal polyps or colon cancer.

According to some embodiments, determining an expression level of SEQ ID NO: 1 below the cutoff value of SEQ ID NO: 1, an expression level of at least one first biomarker below the cutoff value of said at least one first biomarker and an expression level of at least one second biomarker above a the cutoff value of said at least one second biomarker identifies the subject as having pre-cancerous advanced colorectal polyps, wherein said first biomarker is any one or more of SEQ ID NOs: 3-8 and 10-13 and 15-17 and wherein said second biomarker comprises at least one of SEQ ID NOs: 2, 9 and 14. Each possibility is a separate embodiment of the present invention.

According to some embodiments, said second biomarker comprises SEQ ID NO: 2. According to some embodiments, said second biomarker comprises SEQ ID NO: 9. According to some embodiments, said second biomarker comprises SEQ ID NO: 14. According to some embodiments, said second biomarker comprises SEQ ID NOs: 2 and 9. According to some embodiments, said second biomarker comprises SEQ ID NOs: 2 and 14. According to some embodiments, said second biomarker comprises SEQ ID NOs: 9 and 14.

According to some embodiments, the terms "precancerous advanced polyps", "precancerous", "advanced adenoma", "AD", "AA", and "polyps", as used herein, are interchangeable and refer to a colorectal polyp, neoplastic pre-cancerous lesions or other abnormal tissue growth or lesion that is likely to develop into a malignant tumor or adenomatous polyps. It has been shown that detection of precancerous advanced polyps lowers the incidence and mortality from CRC. In fact, around 85% of CRCs are sporadic and developed from adenomas.

According to some embodiments, adenomas that are larger than 1 cm, or those with severe dysplasia or a villous architecture are referred to as "advanced adenomas" and are generally considered to be the most relevant subset to detect in screening. The development of CRC from adenoma is estimated to require 5 to 10 years. Since most CRC cases develop from precancerous lesions, screening has substantial clinical benefits to patients.

According to some embodiments, a "biomarker" includes, but is not limited to, one or more of: a molecular indicator of a specific biological property; a biochemical feature or fact that can be used to detect colorectal cancer. Commonly, "biomarker" encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, electrolytes, elements, and other analytes or sample-derived measures. Biomarkers may also include mutated proteins or mutated nucleic acids. Biomarkers may also refer to non-analyte physiological markers of health status encompassing other clinical characteristics or risk factors of colorectal cancer such as, without limitation, age, ethnicity, and family history of cancer.

As used herein, the term "biomarker" refers to a nucleic acid sequence of a gene or a fragment thereof the expression of which is indicative of colon cancer or precancerous advanced colorectal polyps. The biomarker may be an mRNA or the cDNA corresponding thereto, which represent the gene or a fragment thereof. The biomarker comprise any one or more of SEQ ID NOs: 1-17. According to some embodiments, the biomarker comprises any one or more of SEQ ID NOs: 75-91 or fragments thereof, including but not limited to, any one or more of SEQ ID NOs: 1-17.

According to some embodiments, the terms "nucleic acid sequence", and "polynucleotide", as used herein, are used interchangeably, and include polymeric forms of nucleotides of any length, either deoxyribonucleotides or ribonucleotides, or analogs thereof. The following are non-limiting examples of polynucleotides: a gene or gene fragment, exons, introns, messenger RNA (mRNA), transfer RNA (tRNA), ribosomal RNA (rRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The term also includes both double- and single-stranded molecules.

RNA is highly labile, easily degradable, and therefore not likely to be stable or detectable outside of the protective cellular environment. However, RNA expression which is highly regulated in normal state becomes increasingly dysregulated in a pathological state, such as, cancer. Therefore, profiling RNA expression is useful for identifying cancer type and stage.

Moreover, use of circulating RNA from the plasma for the analysis of cancer is highly attractive for a number of reasons:
  (a) sampling requires a minimally invasive method (extraction of a small amount of blood);
  (b) sampling can be obtained repeatedly and at any time during tumor progression, allowing for analyzing response to treatment;
  (c) the overall simplicity makes it appropriate for use in the asymptomatic population at risk; and
  (d) a correlation was noted between circulating tumor cells and circulating tumor mRNA in colon cancer, and it was found that mRNA is more sensitive than DNA in the plasma of breast cancer patients.

According to some embodiments, the nucleic acid sequence representing the biomarker is circulating mRNA.

According to some embodiments, the term "circulating" refers to segments of nucleic acids found in the bloodstream.

According to some embodiments, the nucleic acid sequence representing the biomarker is a cDNA corresponding to circulating mRNA.

As used herein, the term "cDNA" refers to complementary DNA. According to some embodiments, cDNA refers to an isolated polynucleotide, nucleic acid molecule, or any fragment or complement thereof. According to some embodiments the cDNA is obtained by recombinant techniques or synthesized synthetically, may be double-stranded or single-stranded, representing coding and/or non-coding 5' and 3' sequences.

According to some embodiments, an "analyte" as used herein refers to any substance to be measured and optionally, utilized, for identifying subpopulations having certain disease or disorder. Stated otherwise, a biomarker (analyte) may be a characteristic that is objectively measured and evaluated as an indicator of normal biological processes, pathogenic processes or pharmacological responses to a therapeutic intervention.

According to some embodiments, the term "colon cancer" refers to cancers and/or neoplasms that form in the tissues of the colon (the longest part of the large intestine). Typically, colon cancers are adenocarcinomas (cancers that are initiated in cells that produce and release mucus and other fluids).

According to some embodiments, the term "rectal cancer" refers to cancers and/or neoplasms that form in the tissues of the rectum (the last several inches of the large intestine preceding the anus).

According to some embodiments, the term "colorectal cancer" in the context of the present invention includes, but is not limited to, cancer arises in either the colon or the rectum.

The present invention is based, in part, on the unexpected discovery that a distinct biomarker and a distinct set of biomarkers in a fluid (blood) sample or any excretions from a subject identify a cancerous state or a precancerous state of the subject with high specificity and sensitivity. Thus, identification according to the invention is accurate and reliable. Moreover, since the biomarkers of the invention are obtained from fluid samples (e.g., serum, plasma, or blood) or from excretions (e.g., stool or urine), the methods of the invention are advantageously non-invasive.

As used herein, the terms "identification", "identifying a subject as" and "identifies the subject as having" are interchangeable and encompass any one or more of screening for colorectal cancer; detecting the presence of, or severity of, cancer; prognosis of cancer; early diagnosis of cancer; diagnosing a precancerous advanced polyps; treatment efficacy and/or relapse of cancer; as well as a platform for selecting therapy and/or a treatment for cancer, optimization of a given therapy for cancer, and/or predicting the suitability of a therapy for specific subjects (e.g., patients) or subpopulations or determining the appropriate dosing of a therapeutic product in patients or subpopulations. Each possibility is a separate embodiment of the present invention.

According to some embodiments, the subject is a human subject.

According to some embodiments the sample obtained from the subject is a body fluid or excretion sample including, but not limited to, seminal plasma, blood, peripheral blood, serum, urine, prostatic fluid, seminal fluid, semen, the external secretions of the skin, respiratory, intestinal, and genitourinary tracts, tears, cerebrospinal fluid, sputum, saliva, milk, peritoneal fluid, pleural fluid, peritoneal fluid, cyst fluid, lavage of body cavities, broncho alveolar lavage, lavage of the reproductive system and/or lavage of any other organ of the body or system in the body and stool. Each possibility is a separate embodiment of the present invention.

According to some embodiments, obtaining a biological sample comprising tissue or fluid is carried out by any one or more of the following collection methods blood sampling, urine sampling, stool sampling, sputum sampling, aspiration of pleural or peritoneal fluids, fine needle biopsy, needle biopsy, core needle biopsy and surgical biopsy, and lavage. Each possibility is a separate embodiment of the present invention. Regardless of the procedure employed, once a biopsy/sample is obtained the level of the biomarkers can be determined and diagnosis can thus be made.

According to some embodiments, the sample obtained from the subject is peripheral blood.

According to some embodiments, the term "peripheral blood", as used herein, refers to blood comprising of red blood cells, white blood cells and platelets. Typically, the sample is a pool of circulating blood. According to some embodiments, the sample is a peripheral blood sample not sequestered within the lymphatic system, spleen, liver, or bone marrow.

According to some embodiments, the sample is a plasma sample. According to some embodiments, the sample is a plasma sample derived from peripheral blood.

According to some embodiments, the plurality of biomarkers described herein, optionally includes any sub-combination of biomarkers, and/or a combination featuring at least one other biomarker, for example a known biomarker.

According to some embodiments, as described herein, the plurality of biomarkers is correlated with colorectal cancer.

According to some embodiments, the term "a plurality", as used herein, refers to at least two. According to some embodiments, the term "a plurality" refers to at least 2, 3, 4, 5, 6, 7, 8, 9, 10, 11, 12, 13, 14, 15, 16 and 17.

According to some embodiments, "measuring the expression levels" comprises assessing the presence, absence, quantity or relative amount (which can be an "effective amount") of either a given substance, typically an mRNA or a cDNA, within a clinical or subject-derived sample, including qualitative or quantitative concentration levels of such substances, or otherwise evaluating the values or categorization of a subject's clinical parameters.

According to some embodiments, "measuring the expression levels" comprises determining the mRNA expression levels of said plurality of biomarkers or determining the amount, or relative amount, of cDNA corresponding to the expression level of the mRNA biomarker(s).

According to some embodiments, the cutoff value of the biomarker refers to an expression level which differentiates the population of healthy subjects from the population of non-healthy subject. According to some embodiments, the level of each biomarker set forth in SEQ ID NO: 1 to 17 is below the cutoff value of each of said biomarker in a population of healthy subject.

According to some embodiments, the cutoff value is a statistically significant value. According to some embodiments, the p value of the cutoff value is at most 0.05. According to some embodiments, an expression level of at least one biomarker above or below said cutoff value of said at least biomarker determines the CRC state of the subject.

According to some embodiments, determining the cutoff value for each biomarker includes measuring the expression level of said at least one biomarker in a large population of subjects that are either healthy, have precancerous advanced polyps or have colorectal cancer.

According to some embodiments, the methods of the invention further comprise reverse transcribing each of the mRNA biomarkers and obtaining the corresponding complimentary DNA (cDNA). According to some embodiments, measuring of the quantity of each cDNA is performed by quantitative polymerase chain reaction (qPCR).

According to some embodiments, the expression levels are measured by quantitative real-time PCR (qRT-PCR).

According to some embodiments, the pair of oligonucleotides are preferably selected to have compatible melting temperatures (Tm), e.g., melting temperatures which differ by less than that 7° C., preferably less than 5° C., more preferably less than 4° C., most preferably less than 3° C., ideally between 3° C. and 0° C.

As used herein, quantitative polymerase chain reaction (qPCR) is a method of quantitatively measuring the amplification of DNA using fluorescent probes. This technology utilizes oligonucleotides probes that have a fluorescent probe attached to the 5' end and a quencher to the 3' end. During PCR amplification, these probes hybridize to the target sequences located in the amplicon and as polymerase replicates the template with the probe bound, it also cleaves the fluorescent probe due to polymerase 5'-nuclease activity. Due to the close proximity between the quench molecule and the fluorescent probe normally prevents fluorescence from being detected, the decoupling results in the increase of intensity of fluorescence proportional to the number of the probe cleavage cycles.

According to some embodiments, the length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified". Many variables can influence the mean efficiency of PCR, including target DNA length and secondary structure, primer length and design, primer and dNTP concentrations, and buffer composition, to name but a few. Contamination of the reaction with exogenous DNA (e.g., DNA spilled onto lab surfaces) or cross-contamination is also a major consideration. These reaction conditions must be carefully optimized for each different primer pair and target sequence.

According to some embodiments, determining the expression levels of the biomarkers may comprise detection of the expression or expression levels of specific nucleic acid sequences via any means known in the art, and as described herein.

According to some embodiments, determining the quantity and/or concentration of cDNA or mRNA is performed by employing at least one probe or at least one primer, preferably a primer pair. Typically, the nucleic acid probe or primer is suitable for detecting the expression or expression levels of a specific biomarker of the present invention.

As used herein, a "primer" defines an oligonucleotide which is capable of annealing to (hybridizing with) a target sequence, thereby creating a double stranded region which can serve as an initiation point for DNA synthesis under suitable conditions.

According to some embodiments, the terminology "primer pair" refers herein to a pair of oligonucleotides (oligos) according to at least some embodiments of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions.

According to some embodiments of the present invention, oligonucleotide primers may be of any suitable length, depending on the particular assay format and the particular needs and targeted genomes employed. Optionally, the oligonucleotide primers are at least 12 nucleotides in length, preferably between 15 and 24 molecules, and they may be adapted to be especially suited to a chosen nucleic acid amplification system. As commonly known in the art, the oligonucleotide primers can be designed by taking into consideration the melting point of hybridization thereof with its targeted sequence (Sambrook et al., 1989, Molecular Cloning—A Laboratory Manual, 2nd Edition, CSH Laboratories).

According to some embodiments, the expression levels of the biomarkers of the present invention are determined using the primers listed in Table 2.

According to some embodiments, the "sensitivity" of a diagnostic assay is the percentage of diseased individuals who test positive (percent of "true positives"). Diseased individuals not detected by the assay are "false negatives". Subjects who are not diseased and who test negative in the assay are termed "true negatives." The "specificity" of the diagnostic assay is one (1) minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

According to some embodiments, the method disclosed herein distinguishes a disease or condition (particularly colorectal cancer) with a sensitivity of at least 19% at a specificity of at least 97% when compared to normal subjects (e.g., a healthy individual not afflicted with cancer). According to some embodiments, the method distinguishes a disease or condition with a sensitivity of at least 44% at a specificity of at least 92% when compared to normal subjects. According to some embodiments, the method distinguishes a disease or condition with a sensitivity of at least 56.5% at a specificity of at least 79% when compared to normal subjects. According to some embodiments, the method distinguishes a disease or condition with a sensitivity of at least 58% at a specificity of at least 92% when compared to subjects exhibiting symptoms that mimic disease or condition symptoms. According to some embodiments, the method distinguishes a disease or condition with a sensitivity of at least 66% at a specificity of at least 78% when compared to normal subjects. According to some embodiments, the method distinguishes a disease or condition with a sensitivity of at least 100% at a specificity of at least 85% when compared to normal subjects. According to some embodiments, the method distinguishes a disease or condition with a sensitivity of at least 56.5% at a specificity of at least 79% when compared to normal subjects. According to some embodiments, the method distinguishes precancerous advanced polyps with a sensitivity of at least 53% and colorectal cancer with a sensitivity of at least 87.5% at a specificity of at least 81% when compared to normal subjects.

According to some embodiments, the term "relative quantity" of a biomarker refers to an amount of a biomarker in a subject's sample that is consistent with diagnosis of a particular disease or condition. A relative quantity can be either in absolute amount (e.g., microgram/ml) or a relative amount (e.g., relative intensity of signals).

According to some embodiments, individual biomarkers and/or combinations of biomarkers may optionally be used for diagnosis of time of onset of a disease or condition. Such diagnosis may optionally be useful for a wide variety of conditions, including those conditions with an abrupt onset.

The skilled artisan will understand that associating an indicator with a predisposition to an adverse outcome is a performance (sensitivity & specificity) analysis. For example, an RNA biomarker expression level of greater than a pre-set cutoff value may signal that a patient is having CRC whereas an RNA biomarker expression level less than or equal to the pre-set cutoff value may indicate that a subject is healthy, or not having CRC.

Additionally, a change in biomarker concentration from baseline levels may be reflective of the status of a disease or its progression (if temporal monitoring is involved), or of the therapeutic effect of a treatment whereas the degree of change in biomarker expression level may be related to the severity of CRC. Statistical significance is often determined by comparing two or more populations, and determining a confidence interval (CI) and/or a p value.

According to some embodiments, the confidence intervals (CI) of the invention are 90%, 95%, 97.5%, 98%, 99%, 99.5%, 99.9% and 99.99%, while preferred p values are less than 0.1, 0.05, 0.025, 0.02, 0.01, 0.005, 0.001 or less than 0.0001. Exemplary statistical tests for identifying CRC and precancerous advanced polyps are described hereinafter.

According to some embodiments, the detection of a nucleic acid of interest in a biological sample may be carried out by any method known in the art. Optionally detection of a nucleic acid of interest is effected by hybridization-based assays using an oligonucleotide probe. Traditional hybridization assays include PCR, reverse-transcriptase PCR, Real-time PCR, quantitative PCR, quantitative real-time PCR, RNase protection, in-situ hybridization, primer extension, dot or slot blots (RNA), and Northern blots (i.e., for RNA detection). Other detection methods include kits containing probes on a dipstick setup and the like.

According to some embodiments, probes may be labeled according to numerous well known methods. Non-limiting examples of detectable markers include ligands, fluorophores, chemiluminescent agents, enzymes, and antibodies. Other detectable markers for use with probes, which can enable an increase in sensitivity of the method of the invention, include biotin and radio-nucleotides. It will become evident to the person of ordinary skill that the choice of a particular label dictates the manner in which it is bound to the probe.

According to some embodiments, the probes are selected from the probes listed in Table 2.

According to some embodiments, the probe oligonucleotides may be labeled subsequent to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, FAM, lissamine, phycoerythrin, rhodamine, Cy2, Cy3, Cy3.5, Cy5, Cy5.5, Cy7, FluorX and others can be attached to the oligonucleotides. Preferably, detection of the biomarkers of the invention is achieved by using TaqMan assays, preferably by using combined reporter and quencher molecules (Roche Molecular Systems Inc.).

According to some embodiments, detection of a nucleic acid of interest in a biological sample may also optionally be effected by NAT-based assays, which involve nucleic acid amplification technology, such as PCR for example (or variations thereof such as qPCR for example).

Amplification of a selected, or target, nucleic acid sequence may be carried out by a number of suitable methods. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the q3 replicase system and NASBA.

According to some embodiments, a nucleic acid sample from a subject is amplified under conditions which favor the amplification of the most abundant differentially expressed nucleic acid. According to some embodiments, reverse transcription into cDNA is carried out on an mRNA sample from a patient. According to some embodiments, the amplification of the differentially expressed nucleic acids is carried out simultaneously. It will be realized by a person skilled in the art that such methods could be adapted for the detection of differentially expressed proteins instead of differentially expressed nucleic acid sequences.

According to some embodiments, the nucleic acid (e.g., mRNA) for practicing the present invention may be obtained according to well known methods.

According to some embodiments, detection may also optionally be performed with a chip or other such device. The nucleic acid sample which includes the candidate region to be analyzed is optionally isolated, amplified and labeled with a reporter group. This reporter group may be a fluorescent group such as phycoerythrin. The labeled nucleic acid is then incubated with the probes immobilized on the chip using a fluidics station. Once the reaction is completed, the chip is inserted into a scanner and patterns of hybridization are detected. The hybridization data is collected, as a signal emitted from the reporter groups already incorporated into the nucleic acid, which is now bound to the probes attached to the chip. Since the sequence and position of each probe immobilized on the chip is known, the identity of the nucleic acid hybridized to a given probe can be determined.

It will be appreciated that when utilized along with automated equipment, the above described detection methods may be used to screen multiple samples for a disease and/or pathological condition both rapidly and easily.

According to some embodiment there is provided kit for identifying colorectal cancer or precancerous advanced colorectal polyps in a biological sample, the kit comprising one or more containers filled with a nucleotide primer pair flanking a biomarker comprising a nucleic acid sequences set forth in SEQ ID NO: 1, wherein said nucleotide primer pair is designed to selectively amplify a fragment of the genome of the individual in said sample that includes the biomarker.

According to some embodiments, the nucleotide primer pair is selected from the nucleotide primer pairs listed in Table 2.

According to some embodiments, said nucleotide primer pair comprises SEQ ID NOs: 40 and 41.

According to some embodiments, said biomarker further comprises at least one nucleic acid sequences selected from SEQ ID NOs: 2, 3, 5-7, 12 and 17 and said nucleotide primer pair comprises at least one of SEQ ID NOs: 30 and 31; SEQ ID NOs: 34 and 35; SEQ ID NOs: 67 and 68; SEQ ID NOs: 49 and 50; SEQ ID NOs: 52 and 53; SEQ ID NOs: 64 and 65; and SEQ ID NOs: 73 and 74, respectively.

According to some embodiments, said biomarker comprises the nucleic acid sequences set forth in SEQ ID NOs: 1-3, 5-7, 12 and 17, said nucleotide primer pair comprises SEQ ID NOs: 40 and 41; SEQ ID NOs: 30 and 31; SEQ ID NOs: 34 and 35; SEQ ID NOs: 67 and 68; SEQ ID NOs: 49 and 50; SEQ ID NOs: 52 and 53; SEQ ID NOs: 64 and 65; and SEQ ID NOs: 73 and 74 and said kit is for identifying colorectal cancer.

According to some embodiments, said biomarker is consisting the nucleic acid sequences set forth in SEQ ID NOs: 1-3, 5-7, 12 and 17, said nucleotide primer pair comprises SEQ ID NOs: 40 and 41; SEQ ID NOs: 30 and 31; SEQ ID NOs: 34 and 35; SEQ ID NOs: 67 and 68; SEQ ID NOs: 49 and 50; SEQ ID NOs: 52 and 53; SEQ ID NOs: 64 and 65; and SEQ ID NOs: 73 and 74 and said kit is for identifying colorectal cancer.

According to some embodiments, said biomarker comprises the nucleic acid sequences set forth in SEQ ID NOs: 1 and 5, said nucleotide primer pair comprises SEQ ID NOs: 95 and 96; and SEQ ID NOs: 67 and 68, and said subject is identified as having precancerous advanced colorectal polyps.

According to some embodiments, said biomarker is consisting the nucleic acid sequences set forth in SEQ ID NOs: 1 and 5, said nucleotide primer pair comprises SEQ ID NOs: 40 and 41; and SEQ ID NOs: 67 and 68 and said subject is identified as having precancerous advanced colorectal polyps.

According to some embodiments, said biomarker comprises SEQ ID NO: 1 and at least one nucleic acid sequences selected from SEQ ID NOs: 3, 4, 6 and 14, and said nucleotide primer pair comprises SEQ ID NOs: 40 and 41; and at least one of SEQ ID NOs: 34 and 35; SEQ ID NOs: 55 and 56; SEQ ID NOs: 49 and 50; SEQ ID NOs: 61 and 62, respectively.

According to some embodiments, said biomarker comprises SEQ ID NOs: 1 and 4 and at least one nucleic acid sequences selected from SEQ ID NOs: 3, 6 and 14 and said nucleotide primer pair comprises SEQ ID NOs: 40 and 41 and SEQ ID NOs: 55 and 56; and at least one of SEQ ID NOs: 34 and 35; SEQ ID NOs: 49 and 50; SEQ ID NOs: 61 and 62, respectively.

According to some embodiments, said biomarker comprises SEQ ID NOs: 1, 3 and 4 and said nucleotide primer pair comprises SEQ ID NOs: 40 and 41; SEQ ID NOs: 34 and 35 and SEQ ID NOs: 55 and 56.

According to some embodiments, said biomarker comprises SEQ ID NOs: 1, 4, 6 and 14 and said nucleotide primer pair comprises SEQ ID NOs: 40 and 41 SEQ ID NOs: 55 and 56; SEQ ID NOs: 49 and 50; and SEQ ID NOs: 61 and 62.

According to some embodiments, said biomarker comprises SEQ ID NOs: 1, 3, 4 and 14 and said nucleotide primer pair comprises SEQ ID NOs: 40 and 41; SEQ ID NOs: 34 and 35; SEQ ID NOs: 55 and 56; and SEQ ID NOs: 61 and 62.

According to some embodiments, the terms "cancer" and "colorectal cancer" are interchangeable.

According to some embodiments, the cancer is invasive. According to other embodiments, the cancer is non-invasive. According to yet other embodiments, the cancer is non metastatic. According to some embodiments, the cancer is metastatic. According to some embodiments, the cancer is a metastasis of colorectal cancer.

According to some embodiments, the kits and methods of the invention are used for monitoring individuals who are at high risk for colorectal cancer, such as, those who have been diagnosed in the past with localized disease, metastasized disease or those who are genetically linked to the disease, or those who have family members of first and second degree diagnosed in the past with cancer. Individuals with a history of inflammatory conditions of the colon such as ulcerative colitis or Crohn's colitis may also be considered as individuals who are in high risk groups for colorectal cancer. Molecular diagnostics according to the present invention may be used for monitoring individuals who are undergoing, or have been treated for, colorectal cancer, in order to determine if the cancer has been eliminated. Screening and diagnostic kits and methods according to the present invention may be used in the monitoring of individuals who have been identified as genetically predisposed such as by genetic screening and/or family histories. Screening and diagnostic kits and methods according to the present invention may be used in the monitoring of asymptomatic individuals whether or not identified as genetically predisposed.

The invention is useful for identifying individuals who show at least one symptom or characteristic of cancer, e.g. presence of polyps in the colon.

According to some embodiments, the present invention is used for monitoring individuals who have been identified as having family medical histories which include relatives who have suffered from colorectal cancer. Likewise, the invention is particularly useful to monitor individuals who have been treated and had tumors removed or are otherwise experiencing remission.

According to some embodiments, the present invention further provides a method for treating a subject having colorectal cancer, the method comprising identifying a subject having colorectal cancer or precancerous advanced colorectal polyps, and treating said subject, wherein treating comprises at least one of administering a chemotherapeutic agent, performing bowel resection, applying radiation therapy and a combination thereof.

According to some embodiments, the chemotherapeutic agents, includes, but is not limited to, 5-fluorouraeii, leucovorin, or oxaliplatin or capecitabine; and/or a monoclonal antibody, such as bevacizumab, cetuximab, or pamtunvumab, or alternative monoclonal antibody, or a combination thereof. Each possibility is a separate embodiment of the present invention.

According to some embodiments, treating a subject for precancerous advanced polyps comprises removal of said precancerous advanced polyps.

According to some embodiments, removal of said precancerous advanced polyps comprises performing one or more of colonoscopy, flexible sigmoidoscopy and open surgery. Each possibility is a separate embodiment of the present invention.

According to some embodiments, the identification, diagnosis, early diagnosis and/or prognosis of said subject according to the present invention enables a man skilled in the art (i.e., clinician or physician) to determine and/or manage the subject treatment regimen. Managing subject treatment includes determination of the severity of the cancerous state (e.g., cancer status). For example, if the severity of the cancerous state indicates that surgery is appropriate, the physician may schedule the patient for surgery. Likewise, if the severity of the cancerous state indicates late stage cancer or if the status is acute, no further action may be warranted. Furthermore, if the results show that treatment has been successful, no further management or treatment may be necessary. Alternatively, if the result of the methods of the present invention is inconclusive or there is reason that confirmation of status is necessary, the physician may order more diagnostic tests. Accordingly, patients that are found to have at least one biomarker with an expression level above the cutoff value that identifies them as having colorectal cancer may undergo additional diagnostic procedures.

As used herein, a "subject" commonly refers to mammalian subject. A mammalian subject may be human or non-human, preferably human.

According to some embodiments, a healthy subject is defined as a subject without detectable colorectal diseases or symptoms, colorectal associated diseases or precancerous advanced polyps, determined by conventional diagnostic methods.

Various embodiments and aspects of the present invention as delineated hereinabove and as claimed in the claims section below find experimental support in the following examples.

EXAMPLES

Example 1—Study Population and Specimen Preparation

Subjects at least 50 years old and scheduled for colonoscopy were participated in the study. To ensure that only average risk individuals were enrolled, the following were excluded from the study: previous CRC or adenomas; iron deficiency anemia or haematochezia (blood in the stool) within the previous 6 months; or family history indicating increased risk for the disease (two or more first degree relatives with CRC or one or more with CRC at age 50 years or less; or known Lynch syndrome or familial adenomatous polyposis).

Colonoscopy procedures, including polypectomy and biopsy, were performed by board certified endoscopists using screening standards and site specific standards for sedation, monitoring, imaging and equipment. Histopathology, diagnostic procedures, and staging of biopsy and surgical specimens used routine procedures. Samples from 137 subjects were available for selection into laboratory analysis, including 55 normal subjects, 47 with advanced adenomas and 35 with CRC. The clinical as well as histological parameters of the study groups are depicted in Table 1A.

TABLE 1A

| | Normal N = 55 (%) | Advanced Adenoma N = 47 (%) | CRC N = 35 (%) |
|---|---|---|---|
| Age | | | |
| <50 | 13 (24) | 2 (4) | 5 (14) |
| 50-<60 | 17 (31) | 12 (26) | 5 (14) |
| 60-<70 | 15 (27) | 15 (32) | 10 (29) |
| 70-<80 | 9 (16) | 16 (34) | 14 (40) |
| 80+ | 1 (2) | 2 (4) | 1 (3) |
| Gender | | | |
| Male | 30 (55) | 29 (62) | 19 (54) |
| Female | 25 (45) | 18 (38) | 16 (46) |
| Location | | | |
| Rectum | | 4 (9) | 11 (32) |
| Left | | 16 (34) | 12 (34) |
| Right | | 25 (53) | 12 (34) |
| Unknown (UK) | | 2 (4) | |
| Size | | | |
| <1 cm | | 12 (26) | |
| >=1 cm | | 35 (74) | |
| >=3 cm | | | |
| Villous component | | | |
| + | | 28 (60) | |
| − | | 19 (40) | |
| Tumor Differentiation (TD) Level | | | |
| Well | | | 5 (14) |
| Moderate | | | 20 (57) |
| Poor | | | 5 (14) |
| UK | | | 5 (14) |

TABLE 1A-continued

|  | Normal<br>N = 55<br>(%) | Advanced<br>Adenoma<br>N = 47<br>(%) | CRC<br>N = 35<br>(%) |
|---|---|---|---|
| Stage | | | |
| I |  |  | 5 (14) |
| II |  |  | 18 (51) |
| III |  |  | 11 (31) |
| IV |  |  | 0 (0) |
| UK |  |  | 1 (3) |

Following the consent of patients recruited for the study, about 10 ml of blood were provided before surgery or colonoscopy using a collection tube (vacutainer). The collected blood was kept refrigerated until further processing, up to 4 hours following the collection.

Plasma was separated from blood cells by centrifugation. The plasma was homogenized with TRIzol® Reagent (Invitrogen). Each volume of plasma was mixed with 3.5 volumes of TRIzol reagent. The mixture was divided into storage micro tubes and stored at −80° C. until further purification.

Total RNA extraction was performed according to the following protocol: 300 chloroform (119.38 g/mol) was added to each of four micro-tubes containing TRIzol™-plasma mixture of the same individual. The solution was mixed vigorously and incubated for 10 minutes at room temperature. Subsequently, the mixture was centrifuged for 15 minutes at 14,000 rpm at 4° C. The aqueous phase was transferred to a new tube and mixed vigorously with equal volume of chloroform, incubated for 3 minutes at room temperature and centrifuged for 15 minutes at 14,000 rpm at 4° C. Following the centrifugation, the upper phase was transferred to a new micro tube; next, a total of 1.4 ml RLT buffer from RNeasy™ mini kit (Qiagen) was added and tubes were mixed. Thereafter, 1.5 times volume of 100% EtOH per each separated upper phase was added. The solution was well mixed and incubated at −20° C. for overnight. Following this incubation, the solution was thawed and 700 μl of the mixture was loaded on an RNeasy™ spin column (Qiagen) and micro-centrifuged at 23° C., 10,000 g for 30 seconds and flow-through was discarded. The rest of the thawed sample was loaded and the column centrifuged, as described above until all the solution was filtered through RNeasy™ spin column. Further RNA purification was completed by following the RNeasy™ mini kit protocol (Qiagen). In short, spin column was loaded with the sample and was washed twice with 500 μl of RPE buffer were. Finally, RNA was eluted by adding 35 μl of RNase-free water. For complete re-suspension of the RNA, the eluted RNA was incubated firstly for 5 minutes in a heat block at 65° C. and secondly incubated on ice for 5 minutes, and span down. RNA quantity was measured using Nano-Drop™ instrument (Thermo Scientific).

In order to test for gene expression profile using gene expression chip array, total RNA was purified using TRIzol-plasma mixture of the same individual, thawed on ice and 15 mg of linear acrylamide and 200 μl of chloroform were added per each 1 ml of Trizol and mixed vigorously. After 10 minutes incubation at room temperature, the mixture was centrifuged for 15 minutes at 14000 rpm at 4° C. The aqueous phase was isolated and further RNA purification steps were performed as above described for RNA specimen preparation for qPCR.

For testing gene expression levels by qPCR, 10 microliter of plasma RNA was used for each cDNA reaction. The Reverse Trascriptase reaction was performed with qScript buffer mix and RT enzyme. The produced cDNA was stored at −20° C. For gene expression profiling using Affymetrix expression microarray, cDNA was synthesized, purified and was subjected to fragmentation and biotin labeling.

Example 2—Quantification of Expression Levels

Initially, 72 genes were tested for their expression levels in the different subpopulations of which 17 genes (Table 1B) were selected to the panel of biomarkers for the detection of colorectal cancer.

TABLE 1B

| SEQ<br>ID<br>NO: | Nucleic acid sequence | Corre-<br>sponding<br>gene | Gene<br>SEQ ID<br>NO: | Gene<br>Accession No.<br>(Genebank) |
|---|---|---|---|---|
| 1 | CCT TAC AGC AAC AGA AAG TGA AGG GCC<br>TAA AAA AAC TAG AGA ACT TCA AGA AAA<br>AAG AGG ACG AAA TCA AAC AAT GGT TAG<br>GGA AAG TTT CTC CTG AAG ATG TAG AAT<br>ATT TCA ATT GCC AAC AGG AGC TGG CTT<br>CAG | CHD2 | 75 | NM_001271.3 |
| 2 | AGG ATG AGT GAC GAG TTT GTG GAC TCC<br>TTT AAG AAG GGA CTT CCT CGC CCG AAG<br>AGC GCG GGC ACA GCA ACG CAG ATG CGG<br>C AAA GCT CCA GCT GGA CGC GAG TCT TCC<br>AGT CCT GGT GGG ATC GGA ACT TGG GCA G | BAD | 76 | NM_032989.2 |
| 3 | CCG TGC TGC TCA CCA AAG GTG AAA TTC<br>GAT GCT ACT GTG ATG CTG CCC ACT GTG<br>TAG CCA CTG GTT ATA TGT GTA AAT CTG<br>AGC | BAMBI | 77 | NM_012342.2 |
| 4 | GGA AGA GGT ATG GGA GGA CAT GGC TAT<br>GGT GGA GCT GGT GAT GCA AGT TCA GGT<br>TTT CAT GGT GGT CAT TTC GTA CAT ATG<br>AGA GGG TTG CCT TTT CGT GCA ACT GAA<br>AAT GAC ATT GCT AAT TTC TTC TCA CCA<br>CTA AAT CCA ATA CG | HNRNPH3 | 78 | NM_012207.2 |

TABLE 1B-continued

| SEQ ID NO: | Nucleic acid sequence | Corresponding gene | Gene SEQ ID NO: | Gene Accession No. (Genebank) |
|---|---|---|---|---|
| 5 | CGC CCT ACT ACA TGT CAC CGG AGA GGA TCC ATG AGA ACG GCT ACA ACT TCA AGT CCG ACA TCT GGT CCC TGG GCT GTC TGC TGT ACG AGA TGG CAG CCC TCC AGA GCC CCT TCT ATG GAG ATA AGA TGA ATC TCT TCT CCC TGT GCC A | NEK6 | 79 | NM_014397.5 |
| 6 | AGC CTA TGA ATT CTA CCA TGC GCT AGA CTC CGA GAA CAT GAC CAG AAC TTG TGC ACC AAG GGT CAG GTA GTA AGT GGC CAG TAC CGG ATG CTC GCA AAG | EPAS1 | 80 | NM_001430.4 |
| 7 | TGA AGA TGG AGG CAT TAT CCG GAG AAC CAA ACG GAA AGG AGA GGG ATA TTC AAA TCC AAA CGA GGG AGC AAC AGT AGA AAT CCA CCT GGA AGG CCG CTG TGG TGG AAG GAT GTT TGA CTG CAG AGA TGT GGC ATT CAC TGT G | FKBP5 | 81 | NM_001145776.1 |
| 8 | TGG CTC TCC TTG TCA TTT TCC AGG TAT GCC TGT GTC AAG ATG AGG TCA CGG ACG ATT ACA TCG GAG ACA ACA CCA CAG TGG ACT ACA CTT TGT TCG AGT CTT TGT GCT CCA AGA AGG ACG TGC GGA ACT TTA A | CCR7 | 82 | NM_001838.3 |
| 9 | CCA GTG GAA CTT TAG ACC TCA GCA AAC AGA AAT ATA TGT GGT GCC AGG AGA GAC TGC ACT GGC GTT TTA CAG AGC TAA GAA TCC TAC TGA CAA ACC AGT AAT GGA AAT TTC TAC ATA CAA TAT TGT TCC ATT GAA AGC TGG ACA GTA TTT | COX11 | 83 | NM_001162861.1 |
| 10 | CAA CAC CTT CCA CCA ATA CTC TGT GAA GCT GGG GCA CCC AGA CAC CCT GAA CCA GGG GGA ATT CAA AGA GCT GGT GCG AAA AGA TCT GCA AAT TTT CTC AAG AAG GAG AAT AAG AAT GAA AAG GTC ATA GAA CAC ATC ATG GAG G | S100A9 | 84 | NM_002965.3 |
| 11 | GTC ATC AAG CAC CTG AAC AGG TTC AAG TTC TTT CTT CAA AGA GTC ATC AGA ATA ACA TGG ATT GAA GAG ACT TCC GAA CAC TTG CTA TCT CTT GCT GCT GCT GTT TCA TGG AAG GAG A | CHPT1 | 85 | NM_020244.2 |
| 12 | CTC CCA TCT CAA AGC CCA TTA CAG AGT GCA TAC AGG TGA ACG GCC CTT TCC CTG CAC GTG GCC AGA CTG CCT AAA AAA GTT CTC C | KLF9 | 86 | NM_001206.2 |
| 13 | GTT TTC AAT GAG TAC CAG AGA ATG ACA GGC CGG GAC ATT GAG AAG AGC ATC TGC CGG GAG ATG TCC GGG GAC CTG GAG GAG GGC ATG CTG GCC GTG GTG AAA TGT CTC AAG AAT ACC CCA GCC TTC TTT GCG GAG AGG CTC AAC AAG GCC | ANXA11 | 87 | NM_145868.1 |
| 14 | GAC CCA CCC ACA TAC ATC AGG GAC CTC TCC ATC CAT CAT GCT GCG TCA CAG TCC ATG GCT CCA ATG GCT TGT TGA TCA GGA CCG TTG TGG GCT ATA ACT CTT GGG G TCT GCC ACT AAT TCG ACA TCA GTT TCA | KIAA1199 | 88 | NM_018689.1 |
| 15 | TCG AGG AAA GCT GAA AAT AAA TAT GCA GGA GGG AAC CCC GTT TGC GTG CGC CCA ACT CCC AAG TGG CAA AAA GGA ATT GGA GAA | KIAA10101 | 89 | NM_014736.5 |
| 16 | AAT GAG TTC CTT CTA CAG TCA GAT ATT GAC TTC ATC ATA TTG GAT TGG TTC CAC GCT ATC AAA AAT GCA ATT GAC AGA TTG CCA AAG GAT TCA AGT TGT CCA TCA AGA AAC CTG GAA TTA TTC AAA ATC AAG AGA TCC TCT AGC ACT GAA | ARHGAP15 | 90 | NM_018460.3 |

TABLE 1B-continued

| SEQ ID NO: | Nucleic acid sequence | Corresponding gene | Gene SEQ ID NO: | Gene Accession No. (Genebank) |
|---|---|---|---|---|
| 17 | CAG GAA GAT GGG CAA GAT GAT GGT GAA GGC CCT GTC AGA AGA GAT GGC AGA CAC TCT GGA GGA GGG CTC TGC CTC CCC GAC ATC TCC AGA CTA CAG CCT | SASH3 | 91 | NM_018990.3 |

Subsequently, the required volume of cDNA was diluted ×4, of which 2 µl were used for qPCR. For a typical qPCR reaction the PerfeCTa qPCR SuperMix (catalog #95065, Quanta) was used together with forwards and reverse primers (Table 2) set specific for each gene, hydrolysis probes and diluted cDNA in a final volume of 200 qPCR was performed in a 96 well PCR plate, for 52 cycles at Quanta's specified conditions, in ABI Prism 7900 system. The probes, fluorescently labeled, listed in Table 2 include one or more of the following labels: FAM at the 5' end (also known as 56-FAM), IABkFQ at the 3' end and may further include N,N-diethyl-4-(4-nitronaphthalen-1-ylazo)-phenylamine (also known as 'ZEN'). ZEN may be incorporated at any position. For example, ZEN may be incorporated at position 9 from the 3' end, position 10 from the 3' end, or in the middle of the probe (such that about the same number of nucleotides are stretched at the 3' and 5' directions counting from the ZEN position). The reference genes for normalization were human HPRT1 and human TFRC. Delta-delta Ct and relative quantification for each gene was calculated by DataAssist v3.0. Reference genes primers and probe sequences are as followed: hHPRT1 gene, forwards primer-TATGCTGAGGATTTGGAAAGG (SEQ ID NO: 18), reverse primer-CATCTCCTTCATCACATCTCG (SEQ ID NO: 19; final concentration 300 nM) probe-FAM-TATG-GACAGGACTGAACG-3'IABkFQ (SEQ ID NO: 20) with addition of 4 LNAs (final concentration 200 nM). hTFRC forwards primer-TTGCATATTCTGGAATCCCA (SEQ ID NO: 21), reverse primer-TCAGTTCCTTATAGGTGTC-CATG (SEQ ID NO: 22; final concentration 500 nM), probe-FAM-TCTGTGTCCTCGCAAAAA-3'IABkFQ (SEQ ID NO: 23) with addition of 5 LNAs (final concentration 250 nM). An exemplary flow chart of the process is shown in FIG. 1.

Figure 2A:
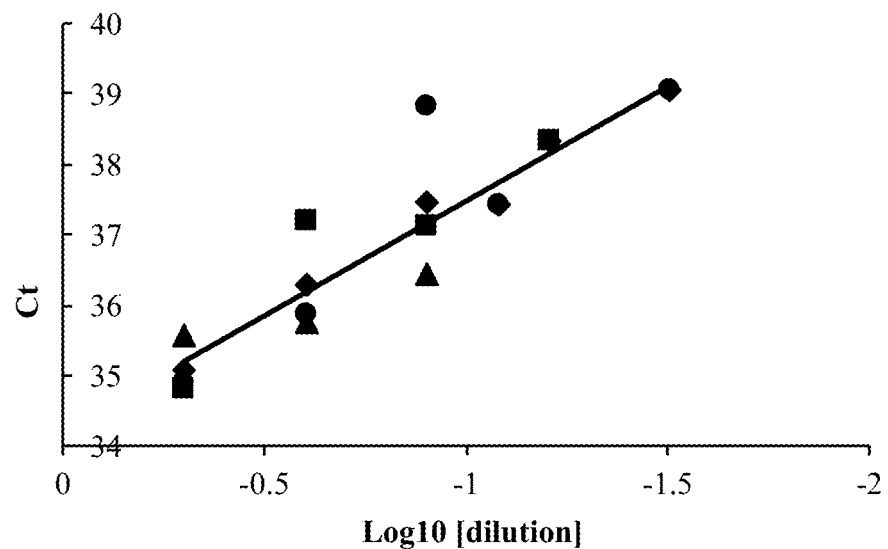
FIG. 2 depicts concentration calibration curves of the primers for each of the house keeping genes HPRT1 (A) and TFRC (B).
Figure 2B:
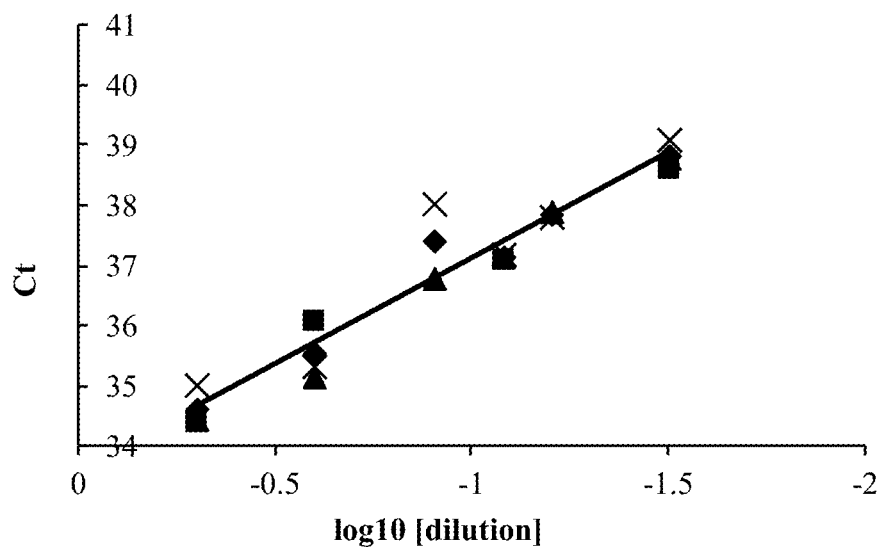
Figure 3A:
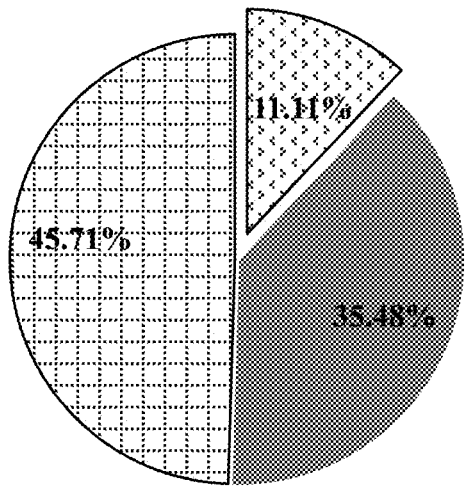
FIG. 3 depicts pie charts of true positive percentages (sensitivity) of subjects having colorectal cancer (Cancer), subjects having precancerous advanced polyps (Advanced Polyp) and the false positive percentage (one (1) minus specificity) of healthy (Normal) subpopulation for 6 different biomarkers: BAD (A; SEQ ID NO: 2), BAMBI (B; SEQ ID NO: 3), NEK6 (C; SEQ ID NO: 5), FKBP5 (D; SEQ ID NO: 7), EPAS1 (E; SEQ ID NO: 6) and CHD2 (F; SEQ ID NO: 1).
Figure 3B:
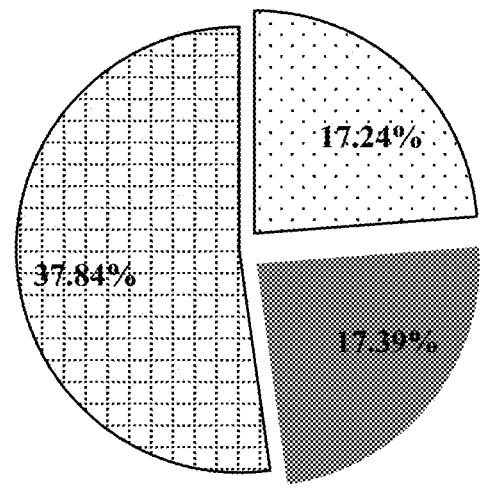
Figure 3C:
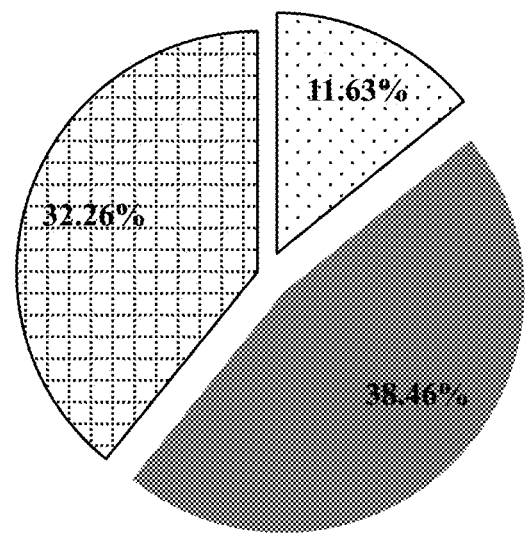
Figure 3D:
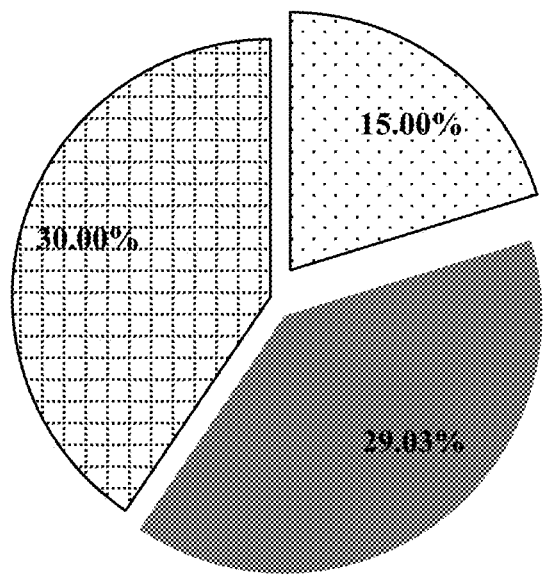
Figure 3E:
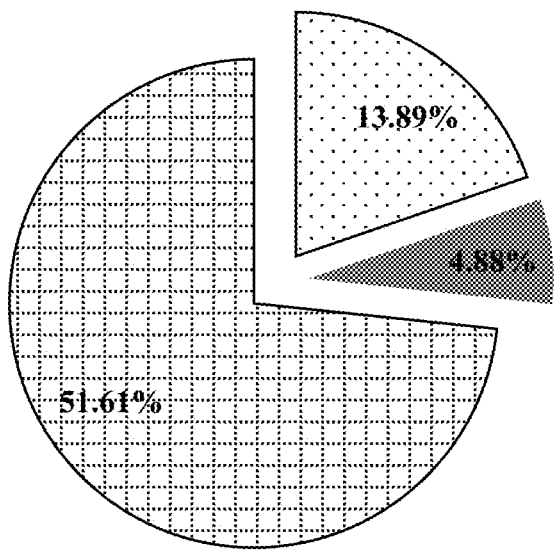
Figure 3F:
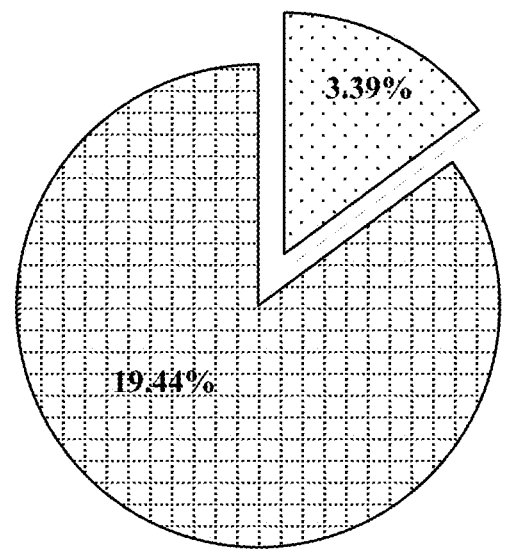

Determining primers and probe final concentration for the cDNA was carried out with 100 fold range calibration curve in 6 cDNA dilutions. Primers and probe concentration which showed the calibration curve optimal slope (−3.3) at accuracy of R2>0.95 were chosen as the optimal concentration for each gene (FIG. 2).

TABLE 2

| Gene Name | Primer/Probe Sequences | SEQ ID NO. |
|---|---|---|
| ANXA11 | | 87 |
| Probe | TGG CCG TGG TGA AAT GTC TCA AGA | 24 |
| Primer 1 (Fw) | GGC CTT GTT GAG CCT CTC | 25 |
| Primer 2 (Rev) | GTT TTC AAT GAG TAC CAG AGA ATG AC | 26 |
| ARHGAP15 | | 90 |
| Probe | CAG ATT GCC AAA GGA TTC AAG TTG TCC A | 27 |
| Primer 1 (Fw) | TTC AGT GCT AGA GGA TCT TTG G | 28 |
| Primer 2 (Rev) | AAT GAG TTC CTT CTA CAG TCA GAT | 29 |
| BAD | | 76 |
| Probe | CTG GAG CTT TGC CGC ATC TGC | 30 |
| Primer 1 (Fw) | AGG ATG AGT GAC GAG TTT GTG | 31 |
| Primer 2 (Rev) | CTG CCC AAG TTC CGA TCC | 32 |
| BAMBI | | 77 |
| Probe | TTC GAT GCT ACT GTG ATG CTG CCC | 33 |
| Primer 1 (Fw) | CCG TGC TGC TCA CCA AA | 34 |
| Primer 2 (Rev) | GCT CAG ATT TAC ACA TAT AAC CAG TG | 35 |
| CCR7 | | 82 |
| Probe | TG ACC TCA TC TTG ACA CAG GCA TAC C | 36 |
| Primer 1 (Fw) | TTA AAG TTC CGC ACG TCC TT | 37 |
| Primer 2 (Rev) | TGG CTC TCC TTG TCA TTT TCC | 38 |
| CHD2 | | 75 |
| Probe | CGA AAT CAA ACA ATG GTT AGG GAA AGT TTC TCC | 39 |
| Primer 1 (Fw) | CCT TAC AGC AAC AGA AAG TGA AG | 40 |
| Primer 2 (Rev) | CTG AAG CCA GCT CCT GTT | 41 |

TABLE 2-continued

| Gene Name | Primer/Probe Sequences | SEQ ID NO. |
|---|---|---|
| CHPT1 | | 85 |
| Probe | AGC AAG TGT TCG GAA GTC TCT TCA ATC C | 42 |
| Primer 1 (Fw) | TCT CCT TCC ATG AAA CAG CAG | 43 |
| Primer 2 (Rev) | GTC ATC AAG CAC CTG AAC AG | 44 |
| COX11 | | 83 |
| Probe | AAA ACG CCA GTG CAGTCT CTC CT | 45 |
| Primer 1 (Fw) | CCA GTG GAA CTT TAG ACCTCA G | 46 |
| Primer 2 (Rev) | AAA TACTGT CCA GCT TCA AAT GG | 47 |
| EPAS1 | | 80 |
| Probe | AGA GTC ACC AGA ACT TGT GCA CCA A | 48 |
| Primer 1 (Fw) | AGC CTA TGA ATT CTA CCA TGC G | 49 |
| Primer 2 (Rev) | CTT TGC GAG CAT CCG GTA | 50 |
| FKBP5 | | 81 |
| Probe | TC AAA CAT CC TTC CAC CAC AGC GG | 51 |
| Primer 1 (Fw) | CAC AGT GAA TGC CAC ATC TCT | 52 |
| Primer 2 (Rev) | TGA AGA TGG AGG CAT TAT CCG | 53 |
| HNRNPH3 | | 78 |
| Probe | TTC AGG TTT TCA TGG TGG TCA TTT CG | 54 |
| Primer 1 (Fw) | GGA AGA GGT ATG GGA GGA CA | 55 |
| Primer 2 (Rev) | CGT ATT GGA TTT AGT GGT GAG AAG | 56 |
| KIAA0101 | | 89 |
| Probe | AAA CGG GGT TCC CTC CTG CAT ATT | 57 |
| Primer 1 (Fw) | TCT GCC ACT AAT TCG ACA TCA G | 58 |
| Primer 2 (Rev) | CTC CAA TTC CTT TTT GCC ACT T | 59 |
| KIAA1199 | | 88 |
| Probe | CCT CTC CAT CCA TCA TAC ATT CTC TCG CT | 60 |
| Primer 1 (Fw) | GAC CCA CCC ACA TAC ATC AG | 61 |
| Primer 2 (Rev) | CCC AAA GAG TTA TAG CCC ACA A | 62 |
| KLF9 | | 86 |
| Probe | AG TGC ATA CA GGT GAA CGG CCC | 63 |
| Primer 1 (Fw) | GGA GAA CTT TTT AAG GCA GTC TG | 64 |
| Primer 2 (Rev) | CTC CCA TCT CAA AGC CCA TT | 65 |
| NEK6 | | 79 |
| Probe | AG GAT CCA TG AGA ACG GCT ACA ACT TC | 66 |
| Primer 1 (Fw) | TGG CAC AGG GAG AAG AGA T | 67 |
| Primer 2 (Rev) | CGC CCT ACT ACA TGT CAC C | 68 |
| S100A9 | | 84 |
| Probe | AG CTC TTT GA ATT CCC CCT GGT TCA | 69 |
| Primer 1 (Fw) | CCT CCA TGA TGT GTT CTA TGA CC | 70 |
| Primer 2 (Rev) | CAA CAC CTT CCA CCA ATA CTC T | 71 |
| SASH3 | | 91 |
| Probe | AGA AGA GAT GGC AGA CAC TCT GGA GG | 72 |
| Primer 1 (Fw) | AGG CTG TAG TCT GGA GAT GTC | 73 |
| Primer 2 (Rev) | CAG GAA GAT GGG CAA GAT GA | 74 |

Example 3—Data Analysis

The presence of pre-cancerous polyps, adenocarcinoma of the colon or normal colon by full colonoscopy was identified based on the presence or absence of the specific molecular markers and their combinations, as schematically exemplified in FIG. 2. For all statistical analysis SPSS package, version 21 (IBM SPSS Statistics) was applied.

Initially, blood was collected from subjects that underwent colonoscopy. Thereby, the results of the colonoscopy and the pathology report for cases where a biopsy sample was taken, or pathology report for carcinoma cases, were used as a reference for the state of the study group. The methodology was also used to identify gene combinations that can provide an optimal biomarker of advanced adenoma and cancer disease states. As detailed above, the study cohort (Table 1A) was designed to consist of 3 subject groups of normal subjects (n=55), advanced adenoma (AA; n=47) and colorectal cancer (CRC; n=35).

Normalization of gene expression by qPCR was based on the expression of two reference genes stably expressed in the plasma: HPRT1 and human TFRC. Primer-probe ratio was calibrated for low RNA amounts, yielding optimal PCR efficiency in 3 orders of magnitude of cDNA concentrations (linear dynamic range).

All PCR results were recorded as Relative Quantity (RQ) calculated by the formula: RQ=2^(-DeltaCt), where the DeltaCt is the difference between the Ct measured for a candidate detector gene marker and the reference housekeeping genes hHPRR1 and TFRC. The cutoff values were determined to ensure that all healthy subjects (Normal) fall below it. The cutoff values for representative biomarkers are listed in Table 3.

TABLE 3

| SEQ ID NO: | Biomarker | Cutoff Value |
|---|---|---|
| 1 | CHD2 | >10 |
| 2 | BAD | >28 |
| 3 | BAMBI | >3.5 |
| 5 | NEK6 | >3.3 |
| 6 | EPAS1 | >0.25 |
| 7 | FKBP5 | >2 |
| 12 | KLF9 | >7 |
| 17 | SASH3 | >2.6 |

Several analytic methods were applied to determine the state of the disease, based on data derived from samples taken from healthy subjects, subjects with precancerous advanced polyps and subject with colorectal cancer.

Figure 4A:
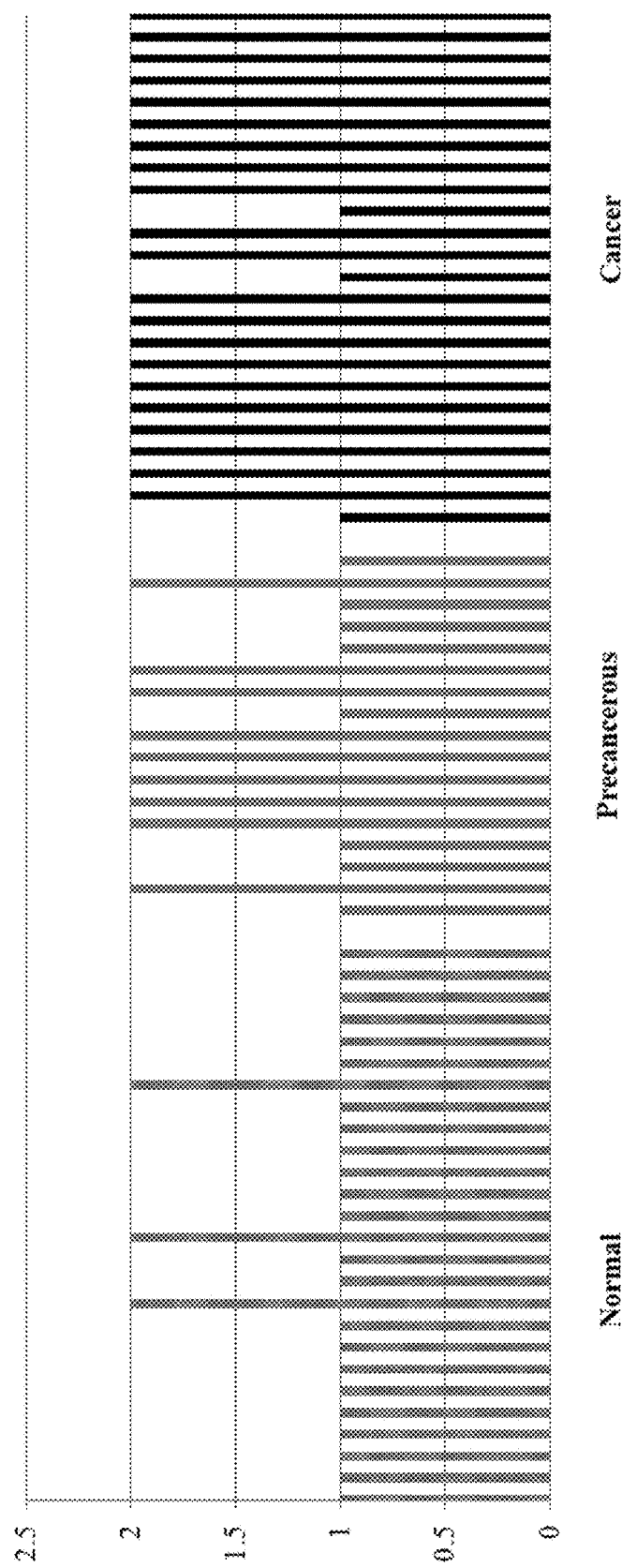
FIG. 4 exhibits the normalized expression levels (each column refers to a single subject) of two biomarker combinations: (A) COX11, KIAA1199 and BAD; and (B) CHD2 and EPAS1, in healthy (Normal-textured grey) subjects, subjects having precancerous advanced polyps (Precancerous-solid grey) and subjects having colorectal cancer (Cancer-solid black).
Figure 4B:
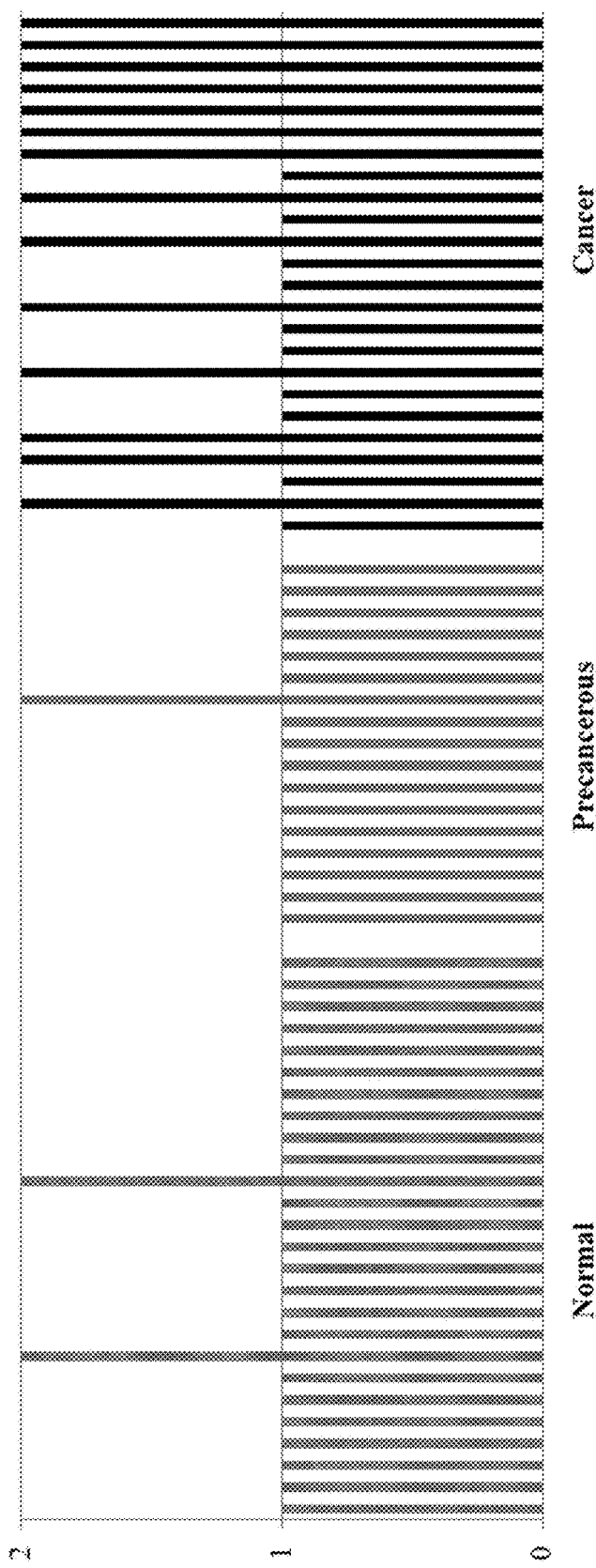

It was further established that by taking a combination of biomarkers the sensitivity of identification of colorectal cancer is improved while not compromising the specificity. In order to compare between the different values, corresponding to expression level ranges of each biomarker in the combination, a combinatorial data analysis algorithm was applied. Once a combination of biomarkers was chosen, the expression levels of each of the biomarkers, in the combination, was compared to its cutoff value. The cutoff values of representative biomarkers are listed in Table 3. Using this algorithm, a value of 1 was assigned to a combination of biomarkers, if the expression level of each biomarker in the combination was below its predetermined cutoff value. A value of 2 was assigned to a combination of biomarkers if the expression level of at least one biomarker in said combination was above its predetermined cutoff value. The assigned values (1 or 2) are also referred herein as normalized expression levels. The normalized expression levels in healthy (N), precancerous (AD) and cancer (CA) populations of the combinations COX11, KIAA1199 and BAD (SEQ ID NOs: 9, 14 and 2; Table 4A) and CHD2 and EPAS1 (SEQ ID NOs: 1 and 6; Table 4B) are presented in FIGS. 4A and 4B, respectively, where expression levels above the cutoff are presented in bold (Tables 4A and 4B).

TABLE 4A

| Clinical Group | Sample | Normalized Expression | | Binary Code CHD2 + EPAS1 |
|---|---|---|---|---|
| | | CHD2 | EPAS1 | |
| N | 3162 | 0.615 | 0.000 | 1 |
| N | 3166 | 1.496 | 0.000 | 1 |
| N | 3176 | 4.215 | 0.000 | 1 |

TABLE 4A-continued

| Clinical Group | Sample | Normalized Expression | | Binary Code CHD2 + EPAS1 |
|---|---|---|---|---|
| | | CHD2 | EPAS1 | |
| N | 3250 | 1.689 | 0.000 | 1 |
| N | 3253 | 2.646 | 0.119 | 1 |
| N | 3254 | 0.958 | 0.071 | 1 |
| N | 3255 | 0.062 | 0.066 | 1 |
| N | 3260 | 10.744 | 2.014 | 2 |
| N | 3263 | 2.000 | 0.000 | 1 |
| N | 3265 | 6.761 | 0.000 | 1 |
| N | 3267 | 1.428 | 0.087 | 1 |
| N | 3269 | 0.850 | 0.000 | 1 |
| N | 3274 | 0.000 | 0.000 | 1 |
| N | 3275 | 0.378 | 0.000 | 1 |
| N | 3280 | 0.000 | 0.000 | 1 |
| N | 3281 | 14.466 | 2.681 | 2 |
| N | 3297 | 2.695 | 0.000 | 1 |
| N | 3363 | 0.000 | 0.254 | 1 |
| N | 3386 | 2.733 | 0.104 | 1 |
| N | 3388 | 3.433 | 0.638 | 1 |
| N | 3420 | 0.000 | 0.000 | 1 |
| N | 3421 | 2.420 | 0.492 | 1 |
| N | 3422 | 2.603 | 0.137 | 1 |
| N | 3436 | 2.642 | 0.000 | 1 |
| N | 3438 | 3.678 | 0.000 | 1 |
| N | 3454 | 0.000 | 0.000 | 1 |
| AD | 3151 | 0.468 | 0.107 | 1 |
| AD | 3213 | 1.457 | 0.046 | 1 |
| AD | 3218 | 0.987 | 0.000 | 1 |
| AD | 3221 | 0.923 | 0.000 | 1 |
| AD | 3273 | 8.384 | 0.000 | 1 |
| AD | 3284 | 0.000 | 0.000 | 1 |
| AD | 3324 | 3.957 | 0.183 | 1 |
| AD | 3341 | 0.000 | 0.175 | 1 |
| AD | 3344 | 2.923 | 0.062 | 1 |
| AD | 3345 | 1.267 | 0.000 | 1 |
| AD | 3349 | 24.440 | 0.697 | 2 |
| AD | 3350 | 1.371 | 0.034 | 1 |
| AD | 3356 | 0.918 | 0.079 | 1 |
| AD | 3357 | 1.969 | 0.182 | 1 |
| AD | 3366 | 0.058 | 0.000 | 1 |
| AD | 3433 | 2.915 | 0.000 | 1 |
| AD | 3437 | 1.689 | 0.000 | 1 |
| CA | 3123 | 7.578 | 0.056 | 1 |
| CA | 3124 | 13.197 | 0.308 | 2 |
| CA | 3129 | 5.829 | 0.272 | 1 |
| CA | 3147 | 17.961 | 0.000 | 2 |
| CA | 3168 | 10.596 | 0.146 | 2 |
| CA | 3290 | 5.071 | 0.132 | 1 |
| CA | 3312 | 7.126 | 0.000 | 1 |
| CA | 3313 | 38.283 | 1.714 | 2 |
| CA | 3319 | 1.530 | 0.000 | 1 |
| CA | 3327 | 1.916 | 0.000 | 1 |
| CA | 3331 | 9.350 | 0.826 | 2 |
| CA | 3337 | 3.414 | 0.618 | 1 |
| CA | 3338 | 9.373 | 0.224 | 1 |
| CA | 3343 | 10.697 | 0.072 | 2 |
| CA | 3374 | 0.000 | 0.306 | 1 |
| CA | 3408 | 5.728 | 4.583 | 2 |
| CA | 3412 | 0.407 | 0.076 | 1 |
| CA | 3440 | 13.793 | 0.000 | 2 |
| CA | 3668 | 18.139 | 0.076 | 2 |
| CA | 3775 | 13.939 | 0.273 | 2 |
| CA | 3783 | 52.058 | 0.308 | 2 |
| CA | 3808 | 16.818 | 0.113 | 2 |
| CA | 3851 | 21.649 | 0.280 | 2 |
| CA | 3874 | 18.359 | 0.119 | 2 |

TABLE 4B

| Clinical Group | Sample | normalized expression COX11 | KIAA1199 | BAD | binary code COX11 + KIAA1199 + BAD |
|---|---|---|---|---|---|
| N | 3162 | 0.980 | 0.000 | 6.067 | 1 |
| N | 3166 | 2.512 | 0.158 | 18.188 | 1 |
| N | 3176 | 1.792 | 0.333 | 5.400 | 1 |
| N | 3250 | 2.104 | 0.147 | 27.796 | 1 |
| N | 3253 | 0.736 | 0.000 | 18.516 | 1 |
| N | 3254 | 2.755 | 0.000 | 14.599 | 1 |
| N | 3255 | 1.784 | 0.000 | 19.566 | 1 |
| N | 3260 | 2.309 | 0.000 | 2.433 | 1 |
| N | 3263 | 1.130 | 0.242 | 10.024 | 1 |
| N | 3265 | 4.605 | 0.175 | 53.725 | 2 |
| N | 3267 | 1.413 | 0.238 | 20.857 | 1 |
| N | 3269 | 0.723 | 0.000 | 17.216 | 1 |
| N | 3274 | 2.973 | 0.000 | 92.903 | 2 |
| N | 3275 | 0.474 | 0.000 | 4.467 | 1 |
| N | 3280 | 0.917 | 0.000 | 0.000 | 1 |
| N | 3281 | 2.034 | 0.000 | 4.253 | 1 |
| N | 3297 | 2.313 | 0.000 | 3.447 | 1 |
| N | 3363 | 0.000 | 0.197 | 0.000 | 1 |
| N | 3386 | 1.943 | 0.000 | 20.101 | 1 |
| N | 3388 | 3.940 | 0.513 | 62.090 | 2 |
| N | 3420 | 0.366 | 0.255 | 2.675 | 1 |
| N | 3421 | 0.957 | 0.000 | 13.040 | 1 |
| N | 3422 | 0.979 | 0.256 | 9.763 | 1 |
| N | 3436 | 2.485 | 0.178 | 5.612 | 1 |
| N | 3438 | 2.589 | 0.234 | 15.265 | 1 |
| N | 3454 | 1.900 | 0.000 | 11.171 | 1 |
| AD | 3151 | 0.158 | 0.000 | 4.425 | 1 |
| AD | 3213 | 1.401 | 0.031 | 38.429 | 2 |
| AD | 3218 | 2.275 | 0.000 | 15.083 | 1 |
| AD | 3221 | 0.680 | 0.000 | 15.657 | 1 |
| AD | 3273 | 1.509 | 0.000 | 48.621 | 2 |
| AD | 3284 | 3.068 | 0.000 | 17.120 | 2 |
| AD | 3324 | 4.656 | 0.158 | 33.911 | 2 |
| AD | 3341 | 1.547 | 0.874 | 19.982 | 2 |
| AD | 3344 | 4.337 |  | 13.003 | 2 |
| AD | 3345 | 1.168 | 0.091 | 3.817 | 1 |
| AD | 3349 | 11.598 | 1.224 | 6.193 | 2 |
| AD | 3350 | 3.384 | 0.115 | 3.674 | 2 |
| AD | 3356 | 0.991 | 0.149 | 7.143 | 1 |
| AD | 3357 | 1.537 | 0.206 | 26.014 | 1 |
| AD | 3366 | 0.336 | 0.000 | 6.222 | 1 |
| AD | 3433 | 5.796 | 0.240 | 62.200 | 2 |
| AD | 3437 | 1.591 | 0.179 | 7.289 | 1 |
| CA | 3123 | 1.941 | 0.000 | 11.771 | 1 |
| CA | 3124 | 7.232 | 0.416 | 18.660 | 2 |
| CA | 3129 | 3.624 | 0.419 | 11.240 | 2 |
| CA | 3147 | 14.408 | 0.238 | 57.370 | 2 |
| CA | 3168 | 10.313 | 0.037 | 10.152 | 2 |
| CA | 3290 | 5.633 | 0.408 | 9.478 | 2 |
| CA | 3312 | 5.958 | 0.545 | 24.071 | 2 |
| CA | 3313 | 25.183 | 4.720 | 100.340 | 2 |
| CA | 3319 | 7.096 | 0.358 | 42.461 | 2 |
| CA | 3327 | 4.907 | 0.000 | 1.694 | 2 |
| CA | 3331 | 9.995 | 0.435 | 51.915 | 2 |
| CA | 3337 | 2.163 | 0.339 | 12.153 | 1 |
| CA | 3338 | 8.872 | 0.576 | 26.613 | 2 |
| CA | 3343 | 9.892 | 0.223 | 39.434 | 2 |
| CA | 3374 | 0.000 | 0.000 | 0.000 | 1 |
| CA | 3408 | 5.382 | 0.000 | 53.354 | 2 |
| CA | 3412 | 1.377 | 0.611 | 31.927 | 2 |
| CA | 3440 | 8.658 | 0.000 | 88.402 | 2 |
| CA | 3668 | 13.485 | 0.214 | 2.661 | 2 |

Example 4—Identification of Colorectal Cancer

To identify colorectal cancer with at least one biomarker the biomarker's sensitivity towards cancer and specificity were chosen to be the highest and the sensitivity to precancerous advanced polyps is minimal. The results of single biomarker analysis, considering biomarkers with an expression level above the predetermined cutoff, are presented hereinafter, in Table 5. For example, as shown in Table 5, CHD2 (SEQ ID NO: 1) show a specificity of 97% and sensitivity of 19% in detection of colorectal cancer.

A combination or a subgroup of biomarkers may be used for identification of the subject as having colorectal cancer, while not compromising the specificity, by applying the combinatorial data analysis algorithm.

As shown in Table 6 combinatorial data analysis may increase the sensitivity of identification of two biomarkers, BAMBI (SEQ ID NO: 3) and HNRNHP3 (SEQ ID NO: 4) in comparison to the sensitivity of each of the biomarkers alone.

In Table 7 it is shown that combinatorial data analysis may increase the sensitivity of identification of two biomarkers, CHD2 (SEQ ID NO: 1) and EPAS1 (SEQ ID NO: 6) in comparison to the sensitivity of each of the biomarkers.

In Table 8 it is shown that combinatorial data analysis increases the sensitivity of identification of three biomarkers, BAMBI (SEQ ID NO: 3), HNRNPH3 (SEQ ID NO: 4) and CHD2 (SEQ ID NO: 1) in comparison to the sensitivity of each of the biomarkers.

TABLE 5

| Biomarker | Total sample no. | Normal Sample analysis Above cutoff/Total | % | Advanced polyp Sample analysis Above cutoff/Total | % | Cancer Sample analysis above cutoff/Total | % |
|---|---|---|---|---|---|---|---|
| BAD | 144 | 4/62 | 6.5% | 16/46 | 34.8% | 16/36 | 44.4% |
| BAMBI | 141 | 10/58 | 17.2% | 8/46 | 17.4% | 14/37 | 37.8% |
| NEK6 | 113 | 5/43 | 11.6% | 15/39 | 38.5% | 10/31 | 32.3% |
| EPAS1 | 108 | 5/36 | 13.9% | 2/41 | 4.9% | 16/31 | 51.6% |
| FKBP5 | 81 | 6/40 | 15.0% | 9/31 | 29.0% | 3/10 | 30.0% |
| CCR7 | 71 | 8/35 | 22.9% | 2/22 | 9.1% | 2/14 | 14.3% |
| CHD2 | 140 | 2/59 | 3.4% | 0/45 | 0.0% | 7/36 | 19.4% |
| COX11 | 106 | 12/51 | 23.5% | 3/27 | 11.1% | 5/28 | 17.9% |
| S100A9 | 73 | 5/31 | 16.1% | 4/21 | 19.0% | 5/21 | 23.8% |
| CHPT1 | 61 | 9/24 | 37.5% | 2/16 | 12.5% | 8/21 | 38.1% |

TABLE 5-continued

| | | Clinical Group | | | | |
|---|---|---|---|---|---|---|
| | | Normal Sample analysis | | Advanced polyp Sample analysis | | Cancer Sample analysis |
| Biomarker | Total sample no. | Above cutoff/ Total | % | Above cutoff/ Total | % | above cutoff/ Total | % |
| KLF9 | 98 | 8/44 | 18.2% | 4/34 | 11.8% | 5/20 | 25.0% |
| ANXA11 | 29 | 4/13 | 30.8% | 0/12 | 0.0% | 2/4 | 50.0% |
| KIAA1199 | 60 | 8/26 | 30.8% | 0/16 | 0.0% | 9/18 | 50.0% |
| KIAA0101 | 55 | 7/31 | 22.6% | 3/18 | 16.7% | 0/6 | 0.0% |
| ARHGAP15 | 52 | 7/29 | 24.1% | 2/18 | 11.1% | 2/5 | 40.0% |
| SASH3 | 98 | 7/33 | 21.2% | 11/40 | 27.5% | 4/25 | 16.0% |
| HNRNPH3 | 69 | 2/34 | 5.88% | 0/18 | 0.00% | 6/17 | 35.29% |

TABLE 6

| Group/ Diagnosis | Biomarker (s) | No. of Patients | No. of Positive | Sensitivity | Specificity |
|---|---|---|---|---|---|
| Group 1/ Colonoscopy Negative | BAMBI | 24 | 4 | N/R | 83.3 |
| Group 2/ Advanced polyp | BAMBI | 12 | 0 | 0.0 | N/R |
| Group 3/ Cancer (stages I-III) | BAMBI | 23 | 9 | 39.1 | N/R |
| Group 1/ Colonoscopy Negative | HNRNPH3 | 24 | 1 | N/R | 95.8 |
| Group 2/ Advanced polyp | HNRNPH3 | 12 | 0 | 0.0 | N/R |
| Group 3/ Cancer (stages I-III) | HNRNPH3 | 23 | 7 | 30.4 | N/R |
| Group 1/ Colonoscopy Negative | BAMBI + HNRNPH3 | 24 | 5 | N/R | 79.2 |
| Group 2/ Advanced polyp | BAMBI + HNRNPH3 | 12 | 0 | 0.0 | N/R |
| Group 3/ Cancer (stages I-III) | BAMBI + HNRNPH3 | 23 | 13 | 56.5 | N/R |

TABLE 7

| Group[1] | Biomarker (s) | No. of Patients | No. of Positive | Sensitivity | Specificity |
|---|---|---|---|---|---|
| Group 1 | CHD2 | 26 | 2 | N/R | 92.3 |
| Group 2 | CHD2 | 17 | 1 | 5.9 | N/R |
| Group 3 | CHD2 | 24 | 12 | 50.0 | N/R |
| Group 1 | EPAS1 | 26 | 2 | N/R | 92.3 |
| Group 2 | EPAS1 | 17 | 0 | 0.0 | N/R |
| Group 3 | EPAS1 | 24 | 3 | 12.5 | N/R |
| Group 1 | CHD2 + EPAS1 | 26 | 1 | N/R | 92.3 |
| Group 2 | CHD2 + EPAS1 | 17 | 1 | 5.9 | N/R |
| Group 3 | CHD2 + EPAS1 | 24 | 14 | 58.3 | N/R |

[1]Groups are assigned to diagnosis as in Table 6.

TABLE 8

| Group[2] | Biomarker (s) | No. of Patients | No. of Positive | Sensitivity | Specificity |
|---|---|---|---|---|---|
| Group 1 | BAMBI | 23 | 3 | N/R | 87.0 |
| Group 2 | BAMBI | 10 | 0 | 0.0 | N/R |
| Group 3 | BAMBI | 21 | 9 | 42.9 | N/R |
| Group 1 | HNRNPH3 | 23 | 1 | N/R | 95.7 |
| Group 2 | HNRNPH3 | 10 | 0 | 0.0 | N/R |
| Group 3 | HNRNPH3 | 21 | 7 | 33.3 | N/R |
| Group 1 | CHD2 | 23 | 1 | N/R | 95.7 |
| Group 2 | CHD2 | 10 | 0 | 0.0 | N/R |
| Group 3 | CHD2 | 21 | 7 | 33.3 | N/R |
| Group 1 | BAMBI + HNRNHP3 + CHD2 | 23 | 5 | N/R | 78.3 |
| Group 2 | BAMBI + HNRNHP3 + CHD2 | 10 | 0 | 0.0 | N/R |
| Group 3 | BAMBI + HNRNHP3 + CHD2 | 21 | 14 | 66.7 | N/R |

[2]Groups are assigned to diagnosis as in Table 6.

In Table 9 it is shown that combinatorial data analysis increases the sensitivity of identification of four biomarkers, CHD2 (SEQ ID NO: 1), EPAS1 (SEQ ID NO: 6), HNRNPH3 (SEQ ID NO: 4) and KIAA1199 (SEQ ID NO: 13) in comparison to the sensitivity of each of the biomarkers.

TABLE 9

| Group[3] | Biomarker (s) | No. of Patients | No. of Positive | Sensitivity | Specificity |
|---|---|---|---|---|---|
| Group 1 | CHD2 | 13 | 1 | N/R | 92.3 |
| Group 2 | CHD2 | 10 | 0 | 0.0 | N/R |
| Group 3 | CHD2 | 13 | 9 | 69.2 | N/R |
| Group 1 | EPAS1 | 13 | 0 | N/R | 100.0 |
| Group 2 | EPAS1 | 10 | 0 | 0.0 | N/R |
| Group 3 | EPAS1 | 13 | 4 | 30.8 | N/R |
| Group 1 | HNRNPH3 | 13 | 0 | N/R | 100.0 |
| Group 2 | HNRNPH3 | 10 | 0 | 0.0 | N/R |
| Group 3 | HNRNPH3 | 13 | 4 | 30.8 | N/R |
| Group 1 | KIAA1199 | 13 | 1 | N/R | 92.3 |
| Group 2 | KIAA1199 | 10 | 1 | 10.0 | N/R |
| Group 3 | KIAA1199 | 13 | 9 | 69.2 | N/R |
| Group 1 | CHD2 + EPAS1 + HNRNPH3 + KIAA1199 | 13 | 2 | N/R | 84.6 |
| Group 2 | CHD2 + EPAS1 + HNRNPH3 + KIAA1199 | 10 | 1 | 10.0 | N/R |
| Group 3 | CHD2 + EPAS1 + HNRNPH3 + KIAA1199 | 13 | 13 | 100.0 | N/R |

[3]Groups are assigned to diagnosis as in Table 6.

In another analytic approach, two datasets of qPCR delta Ct results have been defined, Cancer-Healthy and AD-Healthy. Relationship between genes, as well as dispersion measures of genes among case-healthy groups, were calculated.

In the Cancer-Healthy dataset the correlation between the eight genes listed in Table 3 revealed two clusters of genes that were highly correlated to each other. Cluster 1 includes the genes CHD2, BAD and BAMBI (SEQ ID NOs: 1-3, respectively) and Cluster 2 includes the genes NEK6, FKBP5 and SASH3 (SEQ ID NOs: 5, 7 and 17, respectively). According to these findings the following features were generated:

1. Max_BAD_BAMBI_CHD2—this feature corresponds to the maximum value from the three genes CHD2, BAD and BAMBI (SEQ ID NOs: 1-3, respectively);
2. Max_FKBP5_SASH3_NEK6—this feature corresponds to the maximum value from the three genes NEK6, FKBP5 and SASH3 (SEQ ID NOs: 5, 7 and 17, respectively).

Logistic regression was used to develop a classification model for Cancer-Healthy using four features:
a) Max_BAD_BAMBI_CHD2;
b) Max_FKBP5_SASH3_NEK6;
c) EPAS1; and
d) KLF9.

The analysis resulted with the following model equation:

$$Y \sim max\_BAD\_BAMBI\_CHD2 + 5 \times max\_FKBP5NEK6SASH3 + 23 \times EPAS1 - 3 \times KLF9 - 25.$$

Figure 5:
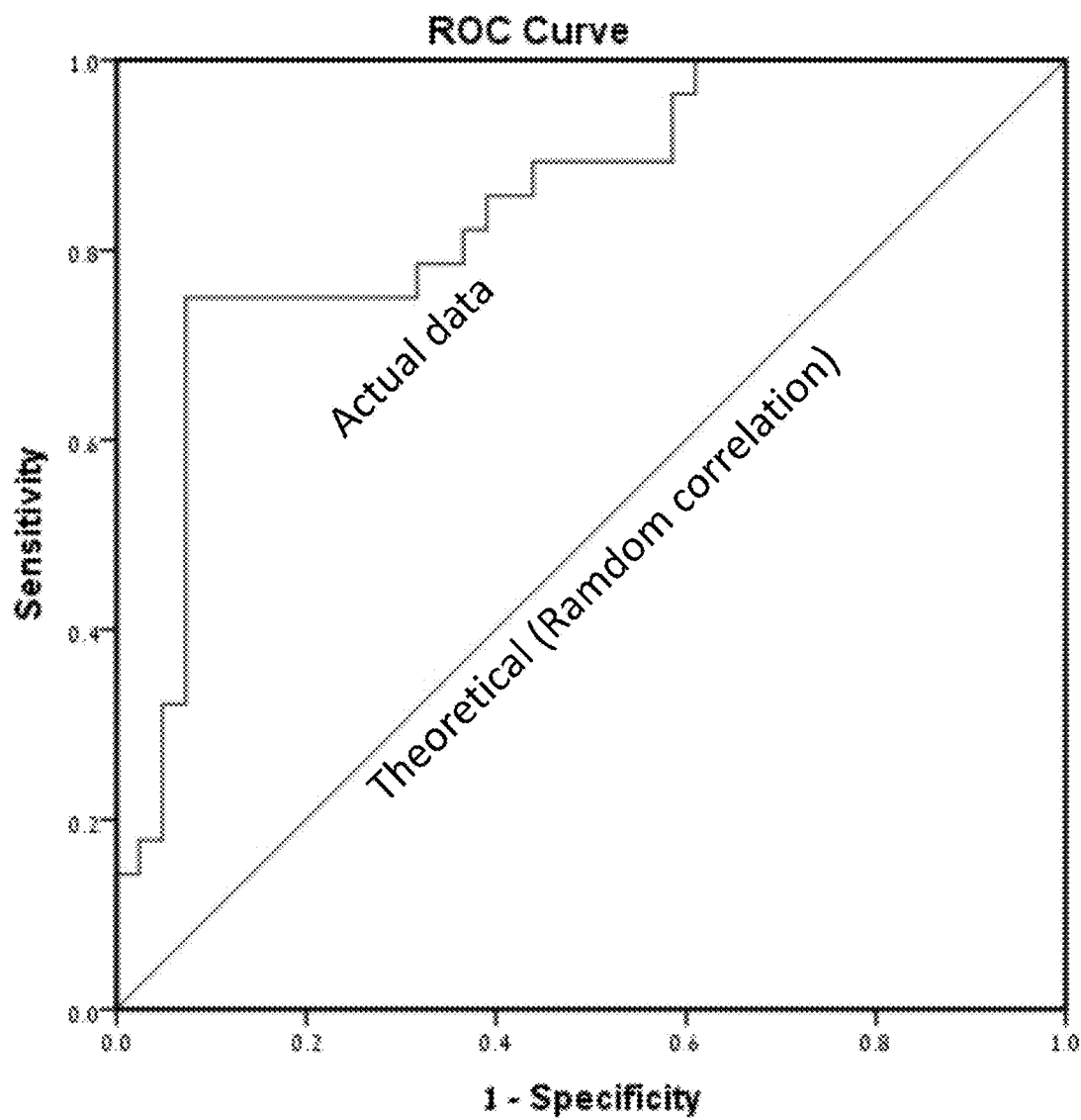
FIG. 5 is a ROC analysis for the maximum values of the biomarkers BAD; BAMBI; CHD2; FKBP5; SASH3; NEK6; EPAS1 and KLF9 (SEQ ID NOs: 2, 3, 1, 7, 17, 5, 6, and 12, respectively, and AUC of cluster-model in healthy (Control) and cancer (CA) yielding sensitivity of 75% and specificity of 93%.
Figure 6:
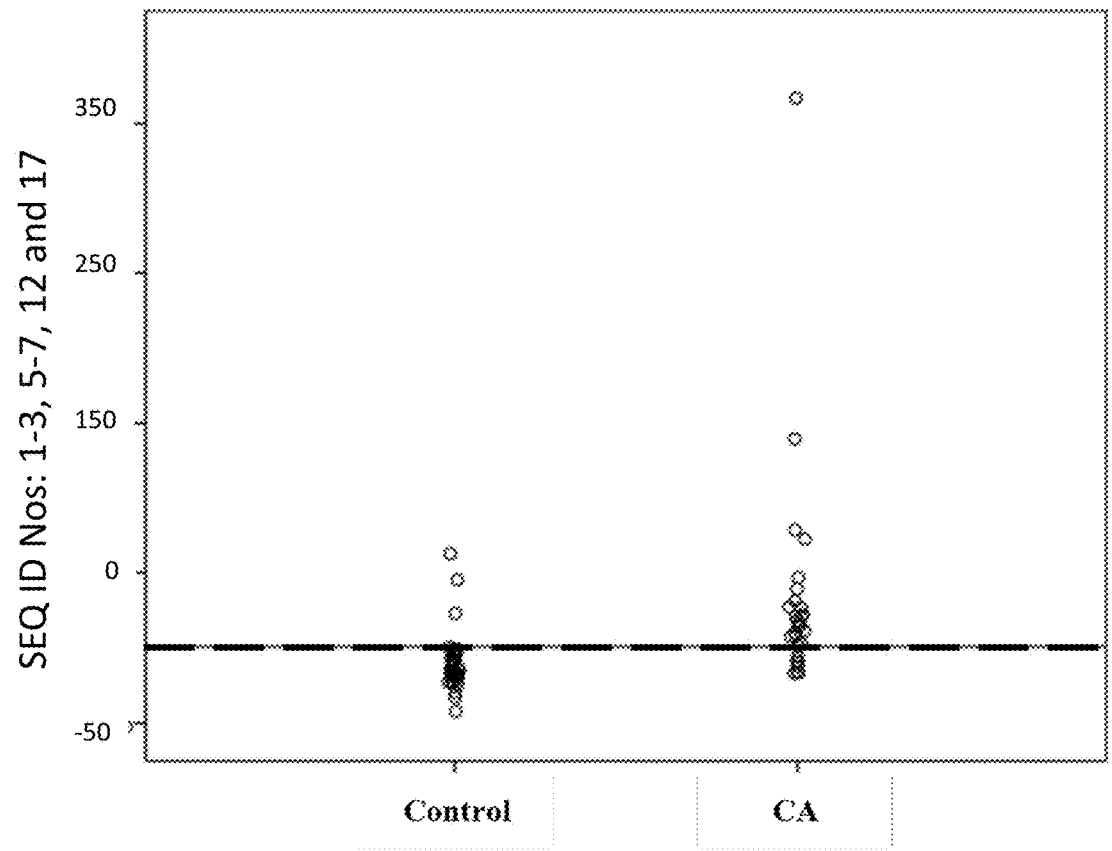
FIG. 6 shows sample distribution, corresponding to the markers of FIG. 5, of cluster-model healthy (Control) and cancer (CA), with the dashed line denoting specificity above 85% and Max Youden index point (0.84).

Receiving operating characteristic (ROC) curve analysis was used to evaluate the separation capability of the model (FIG. 5) and yield (84.3% AUC, 95% Asymptotic CI: 74.8%-93.9%, P value<0.001). The specificity above 85% point and the maximum Youden index point (sensitivity+ specificity −1) met at a point 0.84 with performance sensitivity of 75% and specificity of 93% (FIG. 6).

The case processing summary is provided in Table 10:

| Label | Valid N (listwise) |
| --- | --- |
| Positive[a] | 28 |
| Negative[b] | 41 |
| Missing | 27 |

[a]subject for which gene result was positive, under the nonparametric assumption
[b]subject for which gene result was negative (null hypothesis: true area = 0.5)
c - subjects for which results were missing For the Healthy-AD database t-test and/or stepwise-regression model were used to select the features that participated in model building. BAD and NEK6 (SEQ ID NOs: 2 and 5, respectively) were selected and the equation for this model was as follows:

$$Y \sim BAD + 11 \times NEK6 - 48$$

Figure 7:
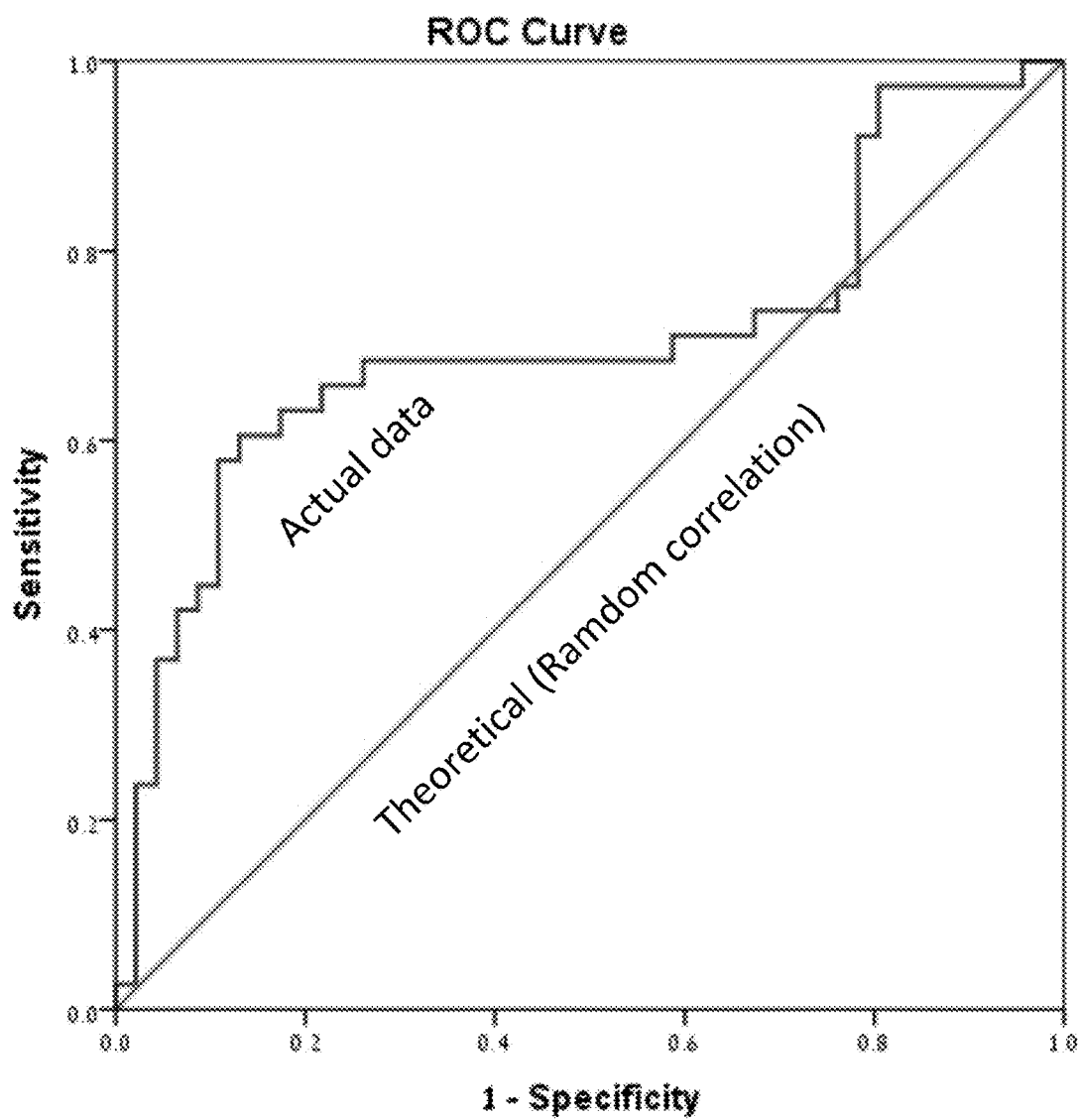
FIG. 7 is a ROC analysis for the maximum values of the biomarkers BAD and NEK6, and AUC of cluster-model in healthy (Control) and precancerous (AD) yielding sensitivity of 60% and specificity of 87%.
Figure 8:
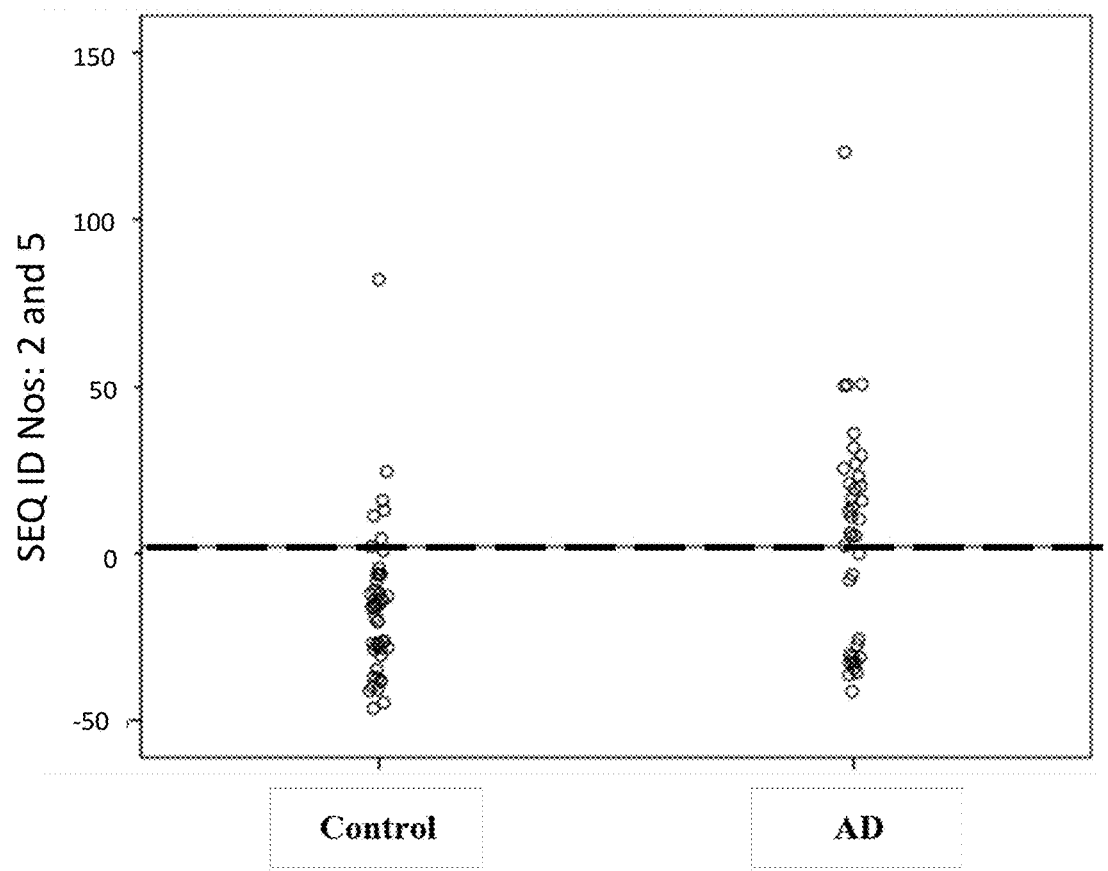
FIG. 8 shows sample distribution, corresponding to the markers of FIG. 7, of cluster-model healthy (Control) and precancerous (AD), with the dashed line denoting specificity above 85% and Max Youden index point (2).

ROC analysis was used to evaluate the separation capability of the model (FIG. 7) on Healthy-AD and yielded 70.5% AUC (95% Asymptotic CI: 58.5%-82.5%, P value<0.001). The specificity above 85% point and the maximum Youden index point meet at a point 2 with performance sensitivity of 60% and specificity of 87% (FIG. 8).

The case processing summary is provided in Table 11:

| Label | Valid N (listwise) |
| --- | --- |
| Positive[a] | 38 |
| Negative[b] | 46 |
| Missing | 24 |

[a]subject for which gene result was positive, under the nonparametric assumption
[b]subject for which gene result was negative (null hypothesis: true area = 0.5)
c - subjects for which results were missing These analyses strongly demonstrated that although purified plasma RNA is not of good quality it is still possible to identify genes with relevance the detection of advanced adenoma or colorectal carcinoma.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating colorectal cancer or precancerous advanced colorectal polyps in a subject, the method comprising:
   (a) obtaining sample mRNA from the subject;
   (b) detecting overexpression of SEQ ID NO: 2 and SEQ ID NO: 5;
   (c) treating the subject with overexpression of SEQ ID NO: 2 and SEQ ID NO: 5, wherein the treatment comprises at least one of administering a chemotherapeutic agent, performing bowel resection, applying radiation therapy and a combination thereof.

2. The method of claim 1, wherein the method further comprises detecting overexpression of at least one nucleic acid selected from SEQ ID NO: 1, 3, 6, 7, 12 and 17.

3. The method of claim 1, wherein the method further comprises detecting overexpression of each of SEQ ID NO: 1, 3, 6-7, 12 and 17.

4. The method of claim 1, wherein the step of detecting comprises reverse transcribing said sample mRNA into cDNA and measuring the presence of the biomarker in the cDNA.

5. The method of claim 4, wherein said measuring the presence of the biomarker in the cDNA is performed by quantitative-PCR.

* * * * *

SEQUENCE LISTING

<160> NUMBER OF SEQ ID NOS: 91

<210> SEQ ID NO 1
<211> LENGTH: 138
<212> TYPE: DNA
<213> ORGANISM: Artificial sequence
<220> FEATURE:
<223> OTHER INFORMATION: Polynucleotide

<400> SEQUENCE: 1
ccttacagca acagaaagtg aagggcctaa aaaaactaga gaacttcaag aaaaaagagg      60
acgaaatcaa acaatggtta gggaaagttt ctcctgaaga tgtagaatat ttcaattgcc     120
aacaggagct ggcttcag                                                   138

<210> SEQ ID NO 2
<211> LENGTH: 137
<212> TYPE: DNA
<213> ORGANISM: Artificial sequence
<220> FEATURE:
<223> OTHER INFORMATION: Polynucleotide

<400> SEQUENCE: 2
aggatgagtg acgagtttgt ggactccttt aagaagggac ttcctcgccc gaagagcgcg     60
ggcacagcaa cgcagatgcg gcaaagctcc agctggacgc gagtcttcca gtcctggtgg    120
gatcggaact tgggcag                                                   137

<210> SEQ ID NO 3
<211> LENGTH: 84
<212> TYPE: DNA
<213> ORGANISM: Artificial sequence
<220> FEATURE:
<223> OTHER INFORMATION: Polynucleotide

<400> SEQUENCE: 3
ccgtgctgct caccaaaggt gaaattcgat gctactgtga tgctgcccac tgtgtagcca     60
ctggttatat gtgtaaatct gagc                                            84

<210> SEQ ID NO 4
<211> LENGTH: 149
<212> TYPE: DNA
<213> ORGANISM: Artificial sequence
<220> FEATURE:
<223> OTHER INFORMATION: Polynucleotide

<400> SEQUENCE: 4
ggaagaggta tgggaggaca tggctatggt ggagctggtg atgcaagttc aggttttcat     60
ggtggtcatt tcgtacatat gagagggttg ccttttcgtg caactgaaaa tgacattgct    120
aatttcttct caccactaaa tccaatacg                                      149

<210> SEQ ID NO 5
<211> LENGTH: 148
<212> TYPE: DNA
<213> ORGANISM: Artificial sequence
<220> FEATURE:
<223> OTHER INFORMATION: Polynucleotide

<400> SEQUENCE: 5
cgccctacta catgtcaccg gagaggatcc atgagaacgg ctacaacttc aagtccgaca     60
tctggtccct gggctgtctg ctgtacgaga tggcagccct ccagagcccc ttctatggag    120
ataagatgaa tctcttctcc ctgtgcca                                       148

<210> SEQ ID NO 6
<211> LENGTH: 99
<212> TYPE: DNA
<213> ORGANISM: Artificial sequence
<220> FEATURE:
<223> OTHER INFORMATION: Polynucleotide

<400> SEQUENCE: 6
agcctatgaa ttctaccatg cgctagactc cgagaacatg accagaactt gtgcaccaag     60
ggtcaggtag taagtggcca gtaccggatg ctcgcaaag                            99

<210> SEQ ID NO 7
<211> LENGTH: 142

<212> TYPE: DNA
<213> ORGANISM: Artificial sequence
<220> FEATURE:
<223> OTHER INFORMATION: Polynucleotide

<400> SEQUENCE: 7

```
tgaagatgga ggcattatcc ggagaaccaa acggaaagga gagggatatt caaatccaaa    60
cgaaggagca acagtagaaa tccacctgga aggccgctgt ggtggaagga tgtttgactg   120
cagagatgtg gcattcactg tg                                             142
```

<210> SEQ ID NO 8
<211> LENGTH: 133
<212> TYPE: DNA
<213> ORGANISM: Artificial sequence
<220> FEATURE:
<223> OTHER INFORMATION: Polynucleotide

<400> SEQUENCE: 8

```
tggctctcct tgtcattttc caggtatgcc tgtgtcaaga tgaggtcacg gacgattaca    60
tcggagacaa caccacagtg gactacactt tgttcgagtc tttgtgctcc aagaaggacg   120
tgcggaactt taa                                                       133
```

<210> SEQ ID NO 9
<211> LENGTH: 150
<212> TYPE: DNA
<213> ORGANISM: Artificial sequence
<220> FEATURE:
<223> OTHER INFORMATION: Polynucleotide

<400> SEQUENCE: 9

```
ccagtggaac tttagacctc agcaaacaga aatatatgtg gtgccaggag agactgcact    60
ggcgttttac agagctaaga atcctactga caaaccagta attggaattt ctacatacaa   120
tattgttcca tttgaagctg gacagtattt                                     150
```

<210> SEQ ID NO 10
<211> LENGTH: 145
<212> TYPE: DNA
<213> ORGANISM: Artificial sequence
<220> FEATURE:
<223> OTHER INFORMATION: Polynucleotide

<400> SEQUENCE: 10

```
caacaccttc caccaatact ctgtgaagct ggggcaccca gacaccctga accaggggga    60
attcaaagag ctggtgcgaa aagatctgca aattttctca agaaggagaa taagaatgaa   120
aaggtcatag aacacatcat ggagg                                          145
```

<210> SEQ ID NO 11
<211> LENGTH: 118
<212> TYPE: DNA
<213> ORGANISM: Artificial sequence
<220> FEATURE:
<223> OTHER INFORMATION: Polynucleotide

<400> SEQUENCE: 11

```
gtcatcaagc acctgaacag gttcaagttc tttcttcaaa gagtcatcag aataacatgg    60
attgaagaga cttccgaaca cttgctatct cttgctgctg ctgtttcatg gaaggaga     118
```

<210> SEQ ID NO 12
<211> LENGTH: 85
<212> TYPE: DNA

```
<213> ORGANISM: Artificial sequence
<220> FEATURE:
<223> OTHER INFORMATION: Polynucleotide

<400> SEQUENCE: 12
ctcccatctc aaagcccatt acagagtgca tacaggtgaa cggcccttc cctgcacgtg      60 gccagactgc cttaaaaagt tctcc                                          85

<210> SEQ ID NO 13
<211> LENGTH: 150
<212> TYPE: DNA
<213> ORGANISM: Artificial sequence
<220> FEATURE:
<223> OTHER INFORMATION: Polynucleotide

<400> SEQUENCE: 13
gttttcaatg agtaccagag aatgacaggc cgggacattg agaagagcat ctgccgggag     60
atgtccgggg acctggagga gggcatgctg gccgtggtga aatgtctcaa gaataccca    120 gccttctttg cggagaggct caacaaggcc                                    150

<210> SEQ ID NO 14
<211> LENGTH: 106
<212> TYPE: DNA
<213> ORGANISM: Artificial sequence
<220> FEATURE:
<223> OTHER INFORMATION: Polynucleotide

<400> SEQUENCE: 14
gacccaccca catacatcag ggacctctcc atccatcatg ctgcgtcaca gtccatggct     60
ccaatggctt gttgatcaag gacgttgtgg gctataactc tttggg                  106

<210> SEQ ID NO 15
<211> LENGTH: 111
<212> TYPE: DNA
<213> ORGANISM: Artificial sequence
<220> FEATURE:
<223> OTHER INFORMATION: Polynucleotide

<400> SEQUENCE: 15
tctgccacta attcgacatc agtttcatcg aggaaagctg aaaataaata tgcaggaggg     60
aaccccgttt gcgtgcgccc aactcccaag tggcaaaaag gaattggaga a            111

<210> SEQ ID NO 16
<211> LENGTH: 150
<212> TYPE: DNA
<213> ORGANISM: Artificial sequence
<220> FEATURE:
<223> OTHER INFORMATION: Polynucleotide

<400> SEQUENCE: 16
aatgagttcc ttctacagtc agatattgac ttcatcatat tggattggtt ccacgctatc     60
aaaaatgcaa ttgacagatt gccaaaggat tcaagttgtc catcaagaaa cctggaatta   120
ttcaaaatcc aaagatcctc tagcactgaa                                    150

<210> SEQ ID NO 17
<211> LENGTH: 99
<212> TYPE: DNA
<213> ORGANISM: Artificial sequence
<220> FEATURE:
<223> OTHER INFORMATION: Polynucleotide

<400> SEQUENCE: 17
```
caggaagatg ggcaagatga tggtgaaggc cctgtcagaa gagatggcag acactctgga    60
ggagggctct gcctccccga catctccaga ctacagcct                            99

<210> SEQ ID NO 18
<211> LENGTH: 21
<212> TYPE: DNA
<213> ORGANISM: Artificial sequence
<220> FEATURE:
<223> OTHER INFORMATION: Polynucleotide

<400> SEQUENCE: 18
tatgctgagg atttggaaag g                                               21

<210> SEQ ID NO 19
<211> LENGTH: 21
<212> TYPE: DNA
<213> ORGANISM: Artificial sequence
<220> FEATURE:
<223> OTHER INFORMATION: Polynucleotide

<400> SEQUENCE: 19
catctccttc atcacatctc g                                               21

<210> SEQ ID NO 20
<211> LENGTH: 18
<212> TYPE: DNA
<213> ORGANISM: Artificial sequence
<220> FEATURE:
<223> OTHER INFORMATION: Polynucleotide

<400> SEQUENCE: 20
tatggacagg actgaacg                                                   18

<210> SEQ ID NO 21
<211> LENGTH: 20
<212> TYPE: DNA
<213> ORGANISM: Artificial sequence
<220> FEATURE:
<223> OTHER INFORMATION: Polynucleotide

<400> SEQUENCE: 21
ttgcatattc tggaatccca                                                 20

<210> SEQ ID NO 22
<211> LENGTH: 23
<212> TYPE: DNA
<213> ORGANISM: Artificial sequence
<220> FEATURE:
<223> OTHER INFORMATION: Polynucleotide

<400> SEQUENCE: 22
tcagttcctt ataggtgtcc atg                                             23

<210> SEQ ID NO 23
<211> LENGTH: 18
<212> TYPE: DNA
<213> ORGANISM: Artificial sequence
<220> FEATURE:
<223> OTHER INFORMATION: Polynucleotide

<400> SEQUENCE: 23
tctgtgtcct cgcaaaaa                                                   18

<210> SEQ ID NO 24

<211> LENGTH: 24
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 24
tggccgtggt gaaatgtctc aaga            24

<210> SEQ ID NO 25
<211> LENGTH: 18
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 25
ggccttgttg agcctctc            18

<210> SEQ ID NO 26
<211> LENGTH: 26
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 26
gttttcaatg agtaccagag aatgac            26

<210> SEQ ID NO 27
<211> LENGTH: 28
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 27
cagattgcca aaggattcaa gttgtcca            28

<210> SEQ ID NO 28
<211> LENGTH: 22
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 28
ttcagtgcta gaggatcttt gg            22

<210> SEQ ID NO 29
<211> LENGTH: 24
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 29
aatgagttcc ttctacagtc agat            24

<210> SEQ ID NO 30
<211> LENGTH: 21
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 30

```
ctggagcttt gccgcatctg c                                              21

<210> SEQ ID NO 31
<211> LENGTH: 21
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 31
aggatgagtg acgagtttgt g                                              21

<210> SEQ ID NO 32
<211> LENGTH: 18
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 32
ctgcccaagt tccgatcc                                                  18

<210> SEQ ID NO 33
<211> LENGTH: 24
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 33
ttcgatgcta ctgtgatgct gccc                                           24

<210> SEQ ID NO 34
<211> LENGTH: 17
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 34
ccgtgctgct caccaaa                                                   17

<210> SEQ ID NO 35
<211> LENGTH: 26
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 35
gctcagattt acacatataa ccagtg                                         26

<210> SEQ ID NO 36
<211> LENGTH: 26
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 36
tgacctcatc ttgacacagg catacc                                         26

<210> SEQ ID NO 37
<211> LENGTH: 20
<212> TYPE: DNA
```

<213> ORGANISM: ARTIFICIAL SEQUENCE
<220> FEATURE:
<223> OTHER INFORMATION: POLYNUCLEOTIDE

<400> SEQUENCE: 37
ttaaagttcc gcacgtcctt                                               20

<210> SEQ ID NO 38
<211> LENGTH: 21
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 38
tggctctcct tgtcattttc c                                             21

<210> SEQ ID NO 39
<211> LENGTH: 33
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 39
cgaaatcaaa caatggttag ggaaagtttc tcc                                33

<210> SEQ ID NO 40
<211> LENGTH: 23
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 40
ccttacagca acagaaagtg aag                                           23

<210> SEQ ID NO 41
<211> LENGTH: 18
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 41
ctgaagccag ctcctgtt                                                 18

<210> SEQ ID NO 42
<211> LENGTH: 28
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 42
agcaagtgtt cggaagtctc ttcaatcc                                      28

<210> SEQ ID NO 43
<211> LENGTH: 21
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 43
tctccttcca tgaaacagca g                                             21

<210> SEQ ID NO 44
<211> LENGTH: 20
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 44
gtcatcaagc acctgaacag                                         20

<210> SEQ ID NO 45
<211> LENGTH: 23
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 45
aaaacgccag tgcagtctct cct                                     23

<210> SEQ ID NO 46
<211> LENGTH: 22
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 46
ccagtggaac tttagacctc ag                                      22

<210> SEQ ID NO 47
<211> LENGTH: 23
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 47
aaatactgtc cagcttcaaa tgg                                     23

<210> SEQ ID NO 48
<211> LENGTH: 25
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 48
agagtcacca gaacttgtgc accaa                                   25

<210> SEQ ID NO 49
<211> LENGTH: 22
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 49
agcctatgaa ttctaccatg cg                                      22

<210> SEQ ID NO 50
<211> LENGTH: 18
<212> TYPE: DNA
<213> ORGANISM: ARTIFICIAL SEQUENCE
<220> FEATURE:

```
<223> OTHER INFORMATION: POLYNUCLEOTIDE

<400> SEQUENCE: 50
ctttgcgagc atccggta                                                    18

<210> SEQ ID NO 51
<211> LENGTH: 24
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 51
tcaaacatcc ttccaccaca gcgg                                             24

<210> SEQ ID NO 52
<211> LENGTH: 21
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 52
cacagtgaat gccacatctc t                                                21

<210> SEQ ID NO 53
<211> LENGTH: 21
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 53
tgaagatgga ggcattatcc g                                                21

<210> SEQ ID NO 54
<211> LENGTH: 26
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 54
ttcaggtttt catggtggtc atttcg                                           26

<210> SEQ ID NO 55
<211> LENGTH: 20
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 55
ggaagaggta tgggaggaca                                                  20

<210> SEQ ID NO 56
<211> LENGTH: 24
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 56
cgtattggat ttagtggtga gaag                                             24
```

```
<210> SEQ ID NO 57
<211> LENGTH: 24
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 57
aaacggggtt ccctcctgca tatt                                              24

<210> SEQ ID NO 58
<211> LENGTH: 22
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 58
tctgccacta attcgacatc ag                                                22

<210> SEQ ID NO 59
<211> LENGTH: 22
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 59
ctccaattcc tttttgccac tt                                                22

<210> SEQ ID NO 60
<211> LENGTH: 29
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 60
cctctccatc catcatacat tctctcgct                                         29

<210> SEQ ID NO 61
<211> LENGTH: 20
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 61
gacccaccca catacatcag                                                   20

<210> SEQ ID NO 62
<211> LENGTH: 22
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 62
cccaaagagt tatagcccac aa                                                22

<210> SEQ ID NO 63
<211> LENGTH: 22
<212> TYPE: DNA
<213> ORGANISM: ARTIFICIAL SEQUENCE
<220> FEATURE:
<223> OTHER INFORMATION: POLYNUCLEOTIDE
```

```
<400> SEQUENCE: 63
agtgcataca ggtgaacggc cc                                             22

<210> SEQ ID NO 64
<211> LENGTH: 23
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 64
ggagaacttt ttaaggcagt ctg                                            23

<210> SEQ ID NO 65
<211> LENGTH: 20
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 65
ctcccatctc aaagcccatt                                                20

<210> SEQ ID NO 66
<211> LENGTH: 27
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 66
aggatccatg agaacggcta caacttc                                        27

<210> SEQ ID NO 67
<211> LENGTH: 19
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 67
tggcacaggg agaagagat                                                 19

<210> SEQ ID NO 68
<211> LENGTH: 19
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 68
cgccctacta catgtcacc                                                 19

<210> SEQ ID NO 69
<211> LENGTH: 25
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 69
agctctttga attcccctg gttca                                           25

<210> SEQ ID NO 70
<211> LENGTH: 23
```

```
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 70
cctccatgat gtgttctatg acc                                          23

<210> SEQ ID NO 71
<211> LENGTH: 22
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 71
caacaccttc caccaatact ct                                           22

<210> SEQ ID NO 72
<211> LENGTH: 26
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 72
agaagagatg gcagacactc tggagg                                       26

<210> SEQ ID NO 73
<211> LENGTH: 21
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 73
aggctgtagt ctggagatgt c                                            21

<210> SEQ ID NO 74
<211> LENGTH: 20
<212> TYPE: DNA
<213> ORGANISM: ARTIFICIAL SEQUENCE
<220> FEATURE:
<223> OTHER INFORMATION: POLYNUCLEOTIDE

<400> SEQUENCE: 74
caggaagatg ggcaagatga                                              20

<210> SEQ ID NO 75
<211> LENGTH: 9374
<212> TYPE: DNA
<213> ORGANISM: HOMO SAPIENS

<400> SEQUENCE: 75
ctcagagctg ggaaggaggc tctagatggc ggctgtgcct tagagagagc gcgctctgct    60
ccctgccttt gcctcacttt acgcaacttt ccctaacttt cgggcagcct caggggggccc   120 ccgtagcccc ctgcctttcc tagggactta ctggggtcga ttcgaacctt tttttgggag    180
aaaagcagct tttaggagct ttcttttcgt gccttgttgg aaagaagcag ccgtactgag    240
agcccaggtc gttgttttttt ccagcttaga agccatggcg cacctccatt tttgtgcgct   300
ctcctaatga ggttttttttt ctttcggacc tgttttagta ttaattattg ctttattttt   360
ttgaccagtt aacatatttg agggttattt tatttatttt tcgtttttta acggaggatt    420
```

```
ttgcctttat ttttaattat ttgggatctg atatttttct actagtagat aggactcttg    480
gtttggacat actacatgga tcagtaaata cctgggcaca ggacttcaaa gcaaacacag    540
attccccctc ccccttaata tttaagaatt aaaagatgat gagaaataag gacaaaagcc    600
aagaggagga cagttcgcta cacagcaatg catcgagtca ctcagcctct gaagaagctt    660
cgggttcaga ctcaggcagt cagtcggaaa gtgagcaggg aagtgatcca ggaagtggac    720
atggcagcga gtcgaacagc agctctgaat cttctgagag tcagtcggaa tctgagagcg    780
aatcagcagg ttccaaatcc cagccagtcc tcccagaagc caaagagaag ccagcctcta    840
agaaggaacg gatagctgat gtgaagaaga tgtgggaaga atatcctgat gtttatgggg    900
tcaggcggtc aaaccgaagc agacaagaac catcgcgatt taatattaag gaagaggcaa    960
gtagcgggtc tgagagtggg agcccaaaaa gaagaggcca gaggcagctg aaaaaacaag   1020
aaaaatggaa acaggaaccc tcagaagatg aacaggaaca aggcaccagt gcagagagtg   1080
agccagaaca aaaaaagta aaagccagaa gacctgtccc cagaagaaca gtgcccaaac    1140
ctcgtgttaa aaagcagccg aagactcagc gtggaaagag aaaaaagcaa gattcttctg   1200
atgaggatga tgatgatgac gaagctccca aaaggcagac tcgtcgaaga gcggctaaaa   1260
acgttagtta caaagaagat gatgactttg agactgactc agatgatctc attgaaatga   1320
ctggagaagg agttgatgaa cagcaagata atagtgaaac tattgaaaag gtcttagatt   1380
caagactggg aaagaaagga gccactggag catctactac tgtatatgcg attgaagcta   1440
atggcgaccc tagtggtgac tttgacactg aaaaggatga aggtgaaatc cagtacctca   1500
tcaagtggaa gggttggtct acatccaca gcacatggga gagtgaagaa tccttacagc    1560
aacagaaagt gaagggccta aaaaaactag agaacttcaa gaaaaaagag gacgaaatca   1620
aacaatggtt agggaaagtt tctcctgaag atgtagaata tttcaattgc caacaggagc   1680
tggcttcaga gttgaataaa cagtatcaga tagtagaaag agtaatagct gtgaagacaa   1740
gtaaatctac attgggtcaa acagattttc cagctcatag tcggaagccg gcaccctcaa   1800
atgagcccga atatctatgt aaatggatgg gactccccta ttcagagtgt agctgggaag   1860
atgaagccct cattggaaag aaattccaga attgcattga cagcttccac agtaggaaca   1920
actcaaaaac catcccaaca agagaatgca aggccctgaa gcagagacca cgatttgtag   1980
ctttaaagaa acaacctgca tatttaggag gggagaatct ggaacttcga gattatcagc   2040
tagaaggtct aaactggcta gctcattcct ggtgcaaaaa taatagtgta atccttgctg   2100
atgaaatggg cctaggaaag accatccaga ccatatcatt cctctcctac tgttccacc    2160 aacaccagct gtatggcccc tttcttatag tcgtcccttt atccaccctc acctcatggc   2220
agagagagtt tgaaatctgg gcaccagaga ttaacgtagt ggtttacata ggtgacctga   2280
tgagcagaaa tacgatacgg gaatatgaat ggattcattc ccaaaccaaa agattgaagt   2340
tcaacgcact tataacaaca tatgagatcc tcttgaaaga taagactgtg ctgggcagta   2400
ttaactgggc cttttctggga gtggatgaag cccatcggtt gaagaatgat gactctttat   2460
tgtataaaac tctgattgat ttcaagtcca accataggct cctgattacg ggacccctc    2520 ttcagaattc cctcaaagag ctctggtcct tgctgcactt tattatgccg gagaagtttg   2580
aattttggga agattttgaa gaagaccatg ggaagggag agaaaatggc taccagagtc    2640
ttcataaggt gctagagcct ttccttctcc ggagagtcaa aaaagatgtg gagaaatccc   2700
ttcctgctaa agtggaacag attctcaggg tggagatgtc agcccttcag aaacagtatt   2760
acaagtggat tctgaccagg aattacaagg ctcttgccaa aggaacaaga ggcagcacat   2820
```

```
ctggttttct taatattgtg atggaactga aaaaatgttg caaccactgc tatctgatta    2880
aaccccctga agaaaatgaa agggaaaatg gacaggagat tcttctgtcc ctcataagga    2940
gcagtgggaa gttgatttta ttagacaaac tgttgacaag acttcgagaa agggggaatc    3000
gagtgcttat cttctctcag atggtgagaa tgttggatat cctggctgaa tacctaacta    3060
ttaaacacta tcctttccag cgtctggatg gttccatcaa gggagaaatc cgaaaacagg    3120
cactggacca cttcaatgca gatgggtctg aggacttctg tttcctgctc tcgacaaggg    3180
ctggtggcct gggaatcaat ttggcttcag cggacacagt cgtcatcttt gactctgact    3240
ggaaccccca gaatgacttg caggcacaag cccgagcgca tagaattggt caaaagaagc    3300
aggtaaatat ttaccgctta gttacaaagg ggactgtgga ggaggagatc atagaacggg    3360
ccaaaaagaa gatggtatta gatcatctgg tgattcagcg catggacacc actggccgga    3420
cgatcctgga aaacaactca ggaaggtcca actcaaatcc ttttaataaa gaagagctga    3480
cagctatttt gaaatttgga gcagaggatc tcttcaaaga actggaaggg gaggaatcag    3540
aacctcagga aatggatata gatgaaattt gcggttggc tgaaacgaga gagaatgaag    3600
tgtcaacaag tgcaacagat gaacttctat cacagtttaa ggttgccaac tttgcaacaa    3660
tggaagatga agaagagcta aagagcgtc ctcacaagga ctgggatgag atcattccag    3720
aggaacaaag gaaaaagta gaggaggaag agcggcagaa ggagctagaa gaaatttata    3780
tgctgcctcg aattcggagt tccactaaaa aggctcagac aaatgacagt gactctgaca    3840
ctgagtctaa gaggcaggcc cagagatcct ctgcttctga gagtgaaacg gaagactctg    3900
atgatgacaa gaagccaaag cgcagagggc gtccgaggag tgtgcggaag gacctcgtgg    3960
agggatttac tgatgcagag atccgaaggt tcatcaaggc ttataagaag tttggtctcc    4020
ctcttgaacg gctggagtgc atagcacgtg atgctgagct ggtagataag tcggtggcag    4080
atctgaagcg cctgggtgaa ctgatccaca cagctgtgt gtcagcaatg caggaatacg    4140
aagagcagct gaaagaaaat gccagcgagg gaaaaggacc agggaaaagg agaggtccaa    4200
caatcaagat atccggagtt caggttaatg tgaaatccat tatccaacat gaagaggagt    4260
ttgagatgct gcataaatct atccctgtgg acctgaaga aaaaaaaaaa tactgcttaa    4320
cctgtcgtgt caaagctgca cattttgatg tagagtgggg ggtggaagat gattctcgcc    4380
tgttgctggg gatttatgaa catggctatg gaaactggga gttaattaaa acagacccag    4440
agcttaaatt aactgacaaa attctgccgg tggagacaga taaaaagcct caggggaagc    4500
agctacagac ccgagcggat tacttgttga gctgctcag aaagggtctg gagaagaagg    4560
gggctgtgac aggtggggaa gaggccaaat taagaagcg gaagcctcgg gtaaagaagg    4620
aaaacaaagt gcccaggctg aaagaggagc atggaattga gctttcatct cctaggcatt    4680
cagataatcc atcagaagag ggagaagtga agatgatgg cttggaaaaa agtccaatga    4740
aaaaaaaaca gaagaagaaa gagaacaagg agaacaagga gaaacaaatg agttctagga    4800
aagacaaaga aggggacaag gaaagaaaga agtcaaaaga taagaaagag aagcctaaaa    4860
gtggtgatgc caaatcttcg agtaaatcaa agcgatctca gggtcctgtc catattacag    4920
caggaagtga acctgtcccc attggagagg atgaggatga tgatctggac caggagacat    4980
tcagcatatg taaggagagg atgaggcccg tgaaaaaggc actgaaacag ctcgacaaac    5040
ctgacaaggg gctcaacgtg caagaacagc tggaacacac ccggaactgc tgctgaaaa    5100
tcggagaccg gatagccgag tgccttaaag cctactcaga tcaggagcac atcaaactct    5160
```

```
ggaggaggaa cctatggatt tttgtttcca agtttacaga atttgatgct cgaaaactgc    5220
ataagttata caagatggct cataagaaaa ggtctcaaga agaagaggag caaaagaaga    5280
aagacgacgt gactgggggt aagaaaccat ttcgtccaga ggcctcaggc tccagccggg    5340
actctctgat atctcagtcc cataccteac acaaccttca ccctcagaag cctcatttgc    5400
ctgcctccca tggcccacag atgcatggac acccaagaga taactacaat caccccaaca    5460
agagacactt cagtaatgca gatcgaggag actggcagag ggaaagaaag ttcaactatg    5520
gtggtggcaa caacaatcca ccatggggaa gcgacaggca ccatcagtat gagcagcact    5580
ggtacaagga ccaccattat ggggaccggc gacatatgga tgcccaccgt tccggaagct    5640
atcgacccaa caacatgtcc agaaagaggc cttatgacca gtacagcagt gaccgagacc    5700
accggggaca cagagattat tatgacaggc accatcatga ctccaagcgg aggagatccg    5760
atgaatttag gcctcaaaat taccaccagc aggatttccg acgaatgtct gatcaccgcc    5820
ccgctatggg ctaccatggc cagggaccct cagaccatta ccgctctttc cacacagata    5880
aactggggga atataaacag cctctacccc cattgcaccc tgcagtctca gatcctcgct    5940
cacccccttc tcagaaatct cctcacgatt ccaagtcacc cctggatcat aggtctcctt    6000
tggagagatc actagaacag aaaaacaacc cagattataa ctggaatgtt cggaaaacat    6060
aaaggacagc tcgtaaagga gagagtaaga gtcaccaaac acgtggatat ttttggtctg    6120
atcctacagt agccggttat ctagaccagt aagtggagtt ttggacatgc tgctgctgtc    6180
aactcactgg ctgaaggagc acttcaagga atgggaggcc tttcactggg tccagctctg    6240
attcgggtca ccactcctgc actttggcac cccatcccat tccagcctag ttctggcctc    6300
ccactttgac gggcacttgg aggaggagct gactgtgtgt gtaccagctt cactgggatg    6360
tgtttcccca gtcaaggaac aggggatctt cagagtcatg aatgtttcct tgccagggtc    6420
agtgttccca ggaccttagt gcatggtcgg ggcaggaact ggtgcatgga ggctgctggg    6480
acctggtgaa cagtgtgtga tttggttgat ttggttcact ctgacatgat ggatgctgct    6540
gatggggagt ggcgagttgg ggcaagcggg tggggacaag cataggactt gaaggggagc    6600
aggtacaccc ctcaaaatgt gttcttggga agtgataca ctcggcctca ttatgtgaaa     6660
cctgtgggtg gggttggggt ggagaagtag agagagggca acagcttcca caactgcttc    6720
atctctgcca acactaattt ttcccacact gtctttgtac atttcagagc tttggtctcc    6780
tgagtgggcc tccttttccc actgtgccag ggaaggtagg tttctctggc tgactgagta    6840
ctgtgagtga ggcaacactg atgccagcat gggtcttact tgactgggga gtaggctgag    6900
tgaggggtag ggtgggtag gtggggagta gtgtggccag ggaactggaa tccctggtgg     6960
atttctgatt cctgtggtga gaaggaaagc tacaggacct ggagaagggg atgcagaggc    7020
aggcctgctg accaacttgt tgcaatcaca aaggtggggg tcctggtgca ggcagtgaac    7080
aggcttctaa tgtggggttc agtagtgcca gcaagtgggg gaaactttca gtattgcgct    7140
aggtcaacac ttcctgctgc atttccttcc ctttgcacag cttgaagaaa tagagtagac    7200
agaatcacac atcatgtggt gggcagatgg aaataagtac ctgtggtgaa caagtttcta    7260
ctgtagttgg agatcattag aattgaattc agtttctctt agaatataat caggtataaa    7320
cctaagttaa actttttccc aaacaaggag catccaaaga cacagtgact tgagctatag    7380
atagtaaaaa tcatacgaga gttgaactga gtcaggttta ggaagcaagt ttggttgcat    7440
caattaagca ggctcttttc aattgactga tgctggggcc ttcagtttta ttctcagtat    7500
agattgccag tattgttaag agtatccaaa ggcctttcta gatggagaca gaataactga    7560
```

```
cttgaacata cagtgtgcct gtaagtgtcc aggctcagag ctggtgaaaa cccttctgtt      7620
gggcgtgtgc agggttaaac tcctgaagta acttgtgagg acttcagtgc ttgctggtgt      7680
cctgggcagc accatgaatg cctttaccaa gacatgccaa gttggatccc ccgaatgaag      7740
cagatgtggc tgtggtgtga cccttgctcc ctgctacaca gagcatcgca gggctggcct      7800
gtgtggtttc cagatgaggg tctgggtccc ggaagcttgt gttgagagct cagtggaccc      7860
accccgcttg ctgaaccctc acagttcttg ggttgtcca gcctggactt gtagcacaca      7920
tgtcctgaag caaagctccg gtgactgcat gagccacctg gccacagtcc tcccatggag      7980
ggcctgccgt gacgctcagt ggagagggca gggcctgtgt ctccacttag gccacacagt      8040
gatgaggaaa ccacagatgg agcttcttgc cgataatact gactctagcc catgattgcc      8100
ttgcccaagc caaagaggaa ggttaggttg gcttgtcgag cccttgagcg ttgggagatg      8160
gggtgggaag gaggtgagcc cctgcagaga gttgggtagt gtccttcagg aatgaaagga      8220
ggggcaaagg agtcaccaga ggtcctgcat ttccatcagg gtttccacag tcatcagggc      8280
ttctctcttg agttgctgat aggagatgtg agttatgccc agagatgtct tatcgtgagg      8340
aaaaagaaac ttccttttgt tcacatttag gactctcagt gccatatgaa gtagcaaaag      8400
gcagtatcgg ccagatcagt gttacattga ttctaaaatt acagtgtccc cattagacaa      8460
ctatttaggg tgctggagta tgtttgaaga gtgtgctggg aaaaaggaag catttcttca      8520
ttgatttaaa tcagtatgaa tattatatgc ctaaataaaa aatttgcaca ggtaaattct      8580
ctcacttgtg aatgggagaa gctgccccag gaatctgtga ggatggtatt ccctggagtc      8640
tggctttgaa agatttcatt gttggtagaa ataacaggtt gagaaagagg gagttagcat      8700
cacctaaaac ctgcacgtga acaagggttg acatgataca ctatggcctt agaaaagggc      8760
caggtgaaac cccaagctaa tcactgcggt cttcagagc cggacagaca ggtgccagca      8820
gagcccgggg ctcactctcc tttcagtcat tcctcagccc ttcgaaggga agcccaaaca      8880 cttttgcacgc tgtgctgcag acattctggc ctggtgtgtc tgaaagttgc atcagtcctc      8940
acggtgcaaa cacagttgat ttaggaagtc acacaatgac actgaaatcc tacagaccaa      9000
aatccacttg tcagcaggag cagcagccca ggccagcac cagcggtctt ccggctcctc      9060
tgagggctgc cacgttgggc gaggggagcc atgccaaggg tccaggctgc tttaggccat      9120
ctgtgcccca ctcatctggg gacagatggt ttttctttat tgtaaaattg tggacttta      9180 aaacctgttg actaaacagt aattaattta tatttgtgaa aaatgccact gtcctagtga      9240
tttctgatgt aaataatgtt gtttatatag tatgtattaa attttcctac attgtaaaac      9300
tgctgtactt ttgattcttg tatattaaaa agtgttactg agcattttta gaattgggct      9360
aacaaaaaaa aaaa                                                         9374
```

<210> SEQ ID NO 76
<211> LENGTH: 986
<212> TYPE: DNA
<213> ORGANISM: Homo sapiens

<400> SEQUENCE: 76

```
aactagggcc cggagcccgg ggtgctggag ggaggcggca ggcccgggtc aggggcctcg        60
agatcgggct tgggcccaga gcatgttcca gatcccagag tttgagccga gtgagcagga      120
agactccagc tctgcagaga ggggcctggg ccccagcccc gcaggggacg ggccctcagg      180
ctccggcaag catcatcgcc aggccccagg cctcctgtgg gacgccagtc accagcagga      240
```

-continued

```
gcagccaacc agcagcagcc atcatggagg cgctggggct gtggagatcc ggagtcgcca      300
cagctcctac cccgcgggga cggaggacga cgaaggatg ggggaggagc ccagcccctt      360
tcggggccgc tcgcgctcgg cgcccccaa cctctgggca gcacagcgct atggccgcga      420
gctccggagg atgagtgacg agtttgtgga ctcctttaag aagggacttc ctcgcccgaa      480
gagcgcgggc acagcaacgc agatgcggca aagctccagc tggacgcgag tcttccagtc      540
ctggtgggat cggaacttgg gcaggggaag ctccgccccc tcccagtgac cttgctcca       600 catcccgaaa ctccacccgt tcccactgcc ctgggcagcc atcttgaata tgggcggaag      660
tacttccctc aggcctatgc aaaaagagga tccgtgctgt ctcctttgga gggagggctg      720
acccagattc ccttccggtg cgtgtgaagc cacggaaggc ttggtcccat cggaagtttt      780
gggttttccg cccacagccg ccggaagtgg ctccgtggcc ccgccctcag gctccgggct      840
ttcccccagg cgcctgcgct aagtcgcgag ccaggtttaa ccgttgcgtc accgggaccc      900 gagccccgc gatgccctgg gggccgtgct cactaccaaa tgttaataaa gcccgcgtct      960
gtgccgccga aaaaaaaaaa aaaaaa                                           986
```

```
<210> SEQ ID NO 77
<211> LENGTH: 1732
<212> TYPE: DNA
<213> ORGANISM: Homo sapiens

<400> SEQUENCE: 77
tttacggcgc ggagccggag agacctgggc tggcgcgggc gggagctgcg gcggataccc       60
ttgcgtgctg tggagaccct actctcttcg ctgagaacgg ccgctagcgg ggactgaagg      120
ccgggagccc actcccgacc cggggctagc gtgcgtccct agagtcgagc ggggcaaggg      180
agccagtggc cgccgacggg ggaccgggaa acttttctgg gctcctgggc gcgccctgta      240
gccgcgctcc atgctccggc agcggcccga aacccagccc cgccgctgac ggcgcccgcc      300
gctccgggca gggcccatgc cctgcgcgct ccggggtcg taggctgccg ccgagccggg      360
gctccggaag ccggcggggg cgccgcggcc gtgcggggcg tcaatggatc gccactccag      420
ctacatcttc atctggctgc agctggagct ctgcgccatg gccgtgctgc tcaccaaagg      480
tgaaattcga tgctactgtg atgctgccca ctgtgtagcc actggttata tgtgtaaatc      540
tgagctcagc gcctgcttct ctagacttct tgatcctcag aactcaaatt ccccactcac      600
ccatggctgc ctggactctc ttgcaagcac gacagacatc tgccaagcca acaggcccg      660 aaaccactct ggcaccacca tacccacatt ggaatgctgt catgaagaca tgtgcaatta      720
cagagggctg cacgatgttc tctctcctcc caggggtgag gcctcaggac aaggaaacag      780
gtatcagcat gatggtagca gaaaccttat caccaaggtg caggagctga cttcttccaa      840
agagttgtgg ttccgggcag cggtcattgc cgtgcccatt gctggagggc tgattttagt      900
gttgcttatt atgttggccc tgaggatgct tcgaagtgaa aataagaggc tgcaggatca      960
gcggcaacag atgctctccc gtttgcacta cagctttcac ggacaccatt ccaaaaaggg     1020
gcaggttgca aagttagact tggaatgcat ggtgccggtc agtgggcacg agaactgctg     1080
tctgacctgt gataaaatga gacaagcaga cctcagcaac gataagatcc tctcgcttgt     1140
tcactggggc atgtacagtg gcacgggaa gctggaattc gtatgacgga gtcttatctg     1200
aactacactt actgaacagc ttgaaggcct tttgagttct gctggacagg agcactttat     1260
ctgaagacaa actcatttaa tcatctttga gagacaaaat gacctctgca aacagaatct     1320
tggatatttc ttctgaagga ttatttgcac agacttaaat acagttaaat gtgttatttg     1380
```

```
cttttaaaat tataaaaagc aaagagaaga ctttgtacac actgtcacca gggttatttg    1440
catccaaggg agctggaatt gagtacctaa ataaacaaaa atgtgcccta tgtaagcttc    1500
tacatcttga tttattgtaa agatttaaaa gaaatatata tattttgtct gaaatttaat    1560
agtgtctttc ataaatttaa ctgggaaacg tgagacagta catgttaatt atacaaatgg    1620
ccatttgctg ttaataattt gttctcaact ctaggatgtg gcttggtttt ttttttctc     1680 ttttcttttt taaacaagac caagatcttg cttattcttc catgaaaaaa aa            1732

<210> SEQ ID NO 78
<211> LENGTH: 2427
<212> TYPE: DNA
<213> ORGANISM: Homo sapiens

<400> SEQUENCE: 78
agttctcgct ccgcccccca cttcttgctc gttccctccc atcccccaa gccagtagct      60 gtgctgcgca gctccctaag cggttgtcac cgctggagac ggttgggaga accgttgtgg    120
cgagcgctac acgaggcaaa cgacttctcc cttctttgaa ctggaccccg cgagcaccag    180
agtcggcgta actatcgcct gacaggcatt taaatcaaac ggtattgaga tggattgggt    240
tatgaaacat aatggtccaa atgacgctag tgatgggaca gtacgacttc gtggactacc    300
atttggttgc agcaaagagg aaatagttca gttctttcaa gggttggaaa tcgtgccaaa    360
tgggataaca ttgacgatgg actaccaggg gagaagcaca ggggaggcct tcgtgcagtt    420
tgcttcaaag gagatagcag aaaatgctct ggggaaacac aaggaaagaa tagggcacag    480
gtatattgag atcttcagaa gtagcaggag tgaaatcaaa ggatttatg atccaccaag     540 aagattgctg ggacagcgac cgggaccata tgatagacca ataggaggaa gaggggggtta   600 ttatggagct gggcgtggaa gtatgtatga cagaatgcga cgaggaggtg atggatatga    660
tggtggttat ggaggttttg atgactatgg tggctataat aattacggct atgggaatga    720
tggctttgat gacagaatga gagatggaag aggtatggga ggacatggct atggtggagc    780
tggtgatgca agttcaggtt ttcatggtgg tcatttcgta catatgagag ggttgccttt    840
tcgtgcaact gaaaatgaca ttgctaattt cttctcacca ctaaatccaa tacgagttca    900
tattgatatt ggagctgatg gcagagccac aggagaagca gatgtagagt ttgtgacaca    960
tgaagatgca gtagctgcca tgtctaaaga taaaaataac atgcaacatc gatatattga   1020
actcttcttg aattctactc ctggaggcgg ctctggcatg ggaggttctg aatgggagg    1080 ctacggaaga gatggaatgg ataatcaggg aggctatgga tcagttggaa gaatgggaat   1140
ggggaacaat tacagtggag gatatggtac tcctgatggt ttgggtggtt atggccgtgg   1200
tggtggaggc agtggaggtt actatgggca aggcggcatg agtggaggtg gatggcgtgg   1260
gatgtactga aagcaaaaac accaacatac aagtcttgac aacagcatct ggtctactag   1320
actttcttac agatttaatt tcttttgtat tttaagaact ttataatgac tgaaggaatg   1380
tgttttcaaa atattatttg gtaaagcaac agattgtgat gggaaaatgt tttctgtagg   1440
tttatttgtt gcatactttg acttaaaaat aaatttttat attcaaacca ctgatgttga   1500
tactttttat atactagtta ctcctaaaga tgtgctgcct tcataagatt tgggttgatg   1560
tatttactta ttagttctac aagaagtagt gtggtgtaat tttagaggat aatggttcac   1620
ctctgcgtaa actgcaagtc ttaagcagac atctggaata gagcttgaca ataattagt    1680 gtaacttttt tctttagttc ctcctggaca acactgtaaa tataaagcct aaagatgaag   1740
```

| | |
|---|---|
| tggcttcagg agtataaatt cagctaatta tttctatatt attattttc aaatgtcatt | 1800 |
| tatcaggcat agctctgaaa cattgatgat ctaagaggta ttgatttctg aatattcata | 1860 |
| attgtgttac ctgggtatga gagtgttgga agctgaattc tagccctaga ttttggagta | 1920 |
| aaacccttc agcacttgac cgaaatacca aaatgtctc caaaaaattg atagttgcag | 1980 |
| gttatcgcaa gatgtcttag agtagggtta aggttctcag tgacacaaga attcagtatt | 2040 |
| aagtacatag gtatttacta tggagtataa ttctcacaat tgtattttca gttttctgcc | 2100 |
| caatagagtt taaataactg tataaatgat gactttaaaa aaatgtaagc aacaagtcca | 2160 |
| tgtcatagtc aataaaaaca atcctgcagt tgggttttgt atctgatccc tgcttggagt | 2220 |
| tttagtttaa agaatctata tgtagcaagg aaaaggtgct ttttaatttt aatcccttg | 2280 |
| atcaatatgg ctttttttcca aattggctaa tggatcaaaa tgaaacctgt tgatgtgaat | 2340 |
| tcagttattg aacttgttac ttgttttgc cagaaatgtt attaataaat gtcattgtgg | 2400 |
| gagataatag taaaaaaaaa aaaaaaa | 2427 |

<210> SEQ ID NO 79
<211> LENGTH: 2645
<212> TYPE: DNA
<213> ORGANISM: Homo sapiens

<400> SEQUENCE: 79

| | |
|---|---|
| gggcgggcgc gcgggcgcgc gggcccgcgc aggcggtggc ggcggcggcg gaaccgagct | 60 |
| gacgggcgtg cggccgctgc gccgcaaact cgtgtgggac gcaccgctcc agccgcccgc | 120 |
| gggccagcgc accggtcccc cagcggcagc cgagcccgcc cgcgcgccgt tcgtgccctc | 180 |
| gtgaggctgg catgcaggat ggcaggacag cccggccaca tgccccatgg agggagttcc | 240 |
| aacaacctct gccacaccct ggggcctgtg catcctcctg acccacagag gcatcccaac | 300 |
| acgctgtctt ttcgctgctc gctggcggac ttccagatcg aaaagaagat aggccgagga | 360 |
| cagttcagcg aggtgtacaa ggccacctgc ctgctggaca ggaagacagt ggctctgaag | 420 |
| aaggtgcaga tctttgagat gatggacgcc aaggcgaggc aggactgtgt caaggagatc | 480 |
| ggcctcttga agcaactgaa ccacccaaat atcatcaagt atttggactc gtttatcgaa | 540 |
| gacaacgagc tgaacattgt gctggagttg gctgacgcag gggacctctc gcagatgatc | 600 |
| aagtacttta gaagcagaa gcggctcatc ccggagagga cagtatggaa gtactttgtg | 660 |
| cagctgtgca gcgccgtgga gcacatgcat tcacgccggg tgatgcaccg agacatcaag | 720 |
| cctgccaacg tgttcatcac agccacgggc gtcgtgaagc tcggtgacct tggtctgggc | 780 |
| cgcttcttca gctctgagac caccgcagcc cactccctag tggggacgcc ctactacatg | 840 |
| tcaccggaga ggatccatga aacggctac aacttcaagt ccgacatctg gtccctgggc | 900 |
| tgtctgctgt acgagatggc agccctccag agccccttct atggagataa gatgaatctc | 960 |
| ttctccctgt gccagaagat cgagcagtgt gactaccccc cactcccgg ggagcactac | 1020 |
| tccgagaagt tacgagaact ggtcagcatg tgcatctgcc ctgaccccca ccagagacct | 1080 |
| gacatcggat acgtgcacca ggtggccaag cagatgcaca tctggatgtc cagcacctga | 1140 |
| gcgtggatgc accgtgcctt atcaaagcca gcaccacttt gccttacttg agtcgtcttc | 1200 |
| tcttcgagtg gccacctggt agcctagaac agctaagacc acagggttca gcaggttccc | 1260 |
| caaaaggctg cccagcctta cagcagatgc tgaaggcaga gcagctgagg gaggggcgct | 1320 |
| ggccacatgt cactgatggt cagattccaa agtccttct ttatactgtt gtggacaatc | 1380 |
| tcagctgggt caataagggc aggtggttca gcgagccacg gcagcccct gtatctggat | 1440 |

```
tgtaatgtga atctttaggg taattcctcc agtgacctgt caaggcttat gctaacagga    1500
gacttgcagg agaccgtgtg atttgtgtag tgagcctttg aaaatggtta gtaccgggtt    1560
cagtttagtt cttagtatct tttcaatcaa gctgtgtgct taatttactc tgttgtaaag    1620
ggataaagtg gaaatcattt ttttccgtgg agtggtgatt ctgctaacat ttttatctac    1680
gttttataac ttggtgagtg acgatgagag ccctgcacct ggccagagtg tcacaggcaa    1740
aaggcatcgg gaagcaggag catcttcttg gcagccaggc tgggccatct tctcctggac    1800
acctgctgtg taccaggaac ttcgtcacct ccttgaatgc tggcggttca tttcatgatc    1860
agtgttaagc atttcctcc atgggaagga agcatgggat atagaaaagc gaagggctgt    1920
cctttacaaa ttctggttct gcaacttcct agcgtgactt tgggcttggg caagtttctt    1980
agccgttctg agccttcatt tcctcatctg tacaatgaga ttaatagtac ctatcatcta    2040
ccttcaggat tgctgacaga cagaatttga aataaaatat gcaagttagc taatacaaaa    2100
agtagatgat ccaaaaatgg tagccactca cccttcacaa actgaagtcc atggaccacg    2160
gaagtcgaga attaatgtac acctgtatca tgtgtaggaa accagaaatg tgttccttat    2220
ttcttgttcc caaacaggat taactgtgaa gactaatttta taaatgtgaa cctaagaaaa    2280
ctccacctct gaaggaaatc atttgaattt tgttttttgta cgtaaagtta accttccaat    2340
tgtctgagct gtcgtcactg acttcatgac agtctggccc tccagacaag agcagcgctg    2400
gcatcgggca ggtgattcct gacacctgct gcctgcaggc attcactgac caggcctttc    2460
ctggaggaaa cacccagggc cgggcggctg ctgtttccac acgtggactc ggatctgctg    2520
tgacaccgtc agcccgacag tctctccata tgcagccttt cctctgtact tttctccatg    2580
gttgaaataa aacagggtga ctgggagtta cttagaattc atgaagattt taaaaaaaaa    2640
aaaaa    2645
```

<210> SEQ ID NO 80
<211> LENGTH: 5184
<212> TYPE: DNA
<213> ORGANISM: Homo sapiens

<400> SEQUENCE: 80

```
gctttacact cgcgagcgga ccgccacacg ggtccggtgc ccgctgcgct tccgccccag     60
cgctcctgag gcggccgtac aatcctcggc agtgtcctga gactgtatgg tcagctcagc    120
ccggcctccg actccttccg actcccagca ttcgagccac ttttttttttt ctttgaaaac    180 tcagaaaagt gactcctttt ccagggaaaa aggaacttgg gttcccttct ctccgtcctc    240
ttttcgggtc tgacagcctc cacccactcc ttccccggac cccgcctccg cgcgcaggtt    300
cctcccagtc acctttctcc accccgccc ccgcacctag cccgccgcgc gccaccttcc    360
acctgactgc gcggggcgct cgggacctgc gcgcacctcg gaccttcacc acccgcccgg    420
gccgcgggga gcgacgagg gccacagccc ccaccccgcc agggagccca ggtgctcggc    480
gtctgaacgt ctcaaagggc cacagcgaca atgacagctg acaaggagaa gaaaaggagt    540
agctcggaga ggaggaagga gaagtcccgg gatgctgcgc ggtgccggcg gagcaaggag    600
acggaggtgt tctatgagct ggcccatgag ctgcctctgc cccacagtgt gagctcccat    660
ctggacaagg cctccatcat gcgactggca atcagcttcc tgcgaacaca caagctcctc    720
tcctcagttt gctctgaaaa cgagtccgaa gccgaagctg accagcagat ggacaacttg    780
tacctgaaag ccttggaggg tttcattgcc gtggtgaccc aagatggcga catgatctttt   840
```

```
ctgtcagaaa acatcagcaa gttcatggga cttacacagg tggagctaac aggacatagt      900
atctttgact tcactcatcc ctgcgaccat gaggagattc gtgagaacct gagtctcaaa      960
aatggctctg gttttgggaa aaaaagcaaa gacatgtcca cagagcggga cttcttcatg     1020
aggatgaagt gcacggtcac caacagaggc cgtactgtca acctcaagtc agccacctgg     1080
aaggtcttgc actgcacggg ccaggtgaaa gtctacaaca actgccctcc tcacaatagt     1140
ctgtgtggct acaaggagcc cctgctgtcc tgcctcatca tcatgtgtga accaatccag     1200
cacccatccc acatggacat ccccctggat agcaagacct tcctgagccg ccacagcatg     1260
gacatgaagt tcacctactg tgatgacaga atcacagaac tgattggtta ccaccctgag     1320
gagctgcttg ccgctcagc ctatgaattc taccatgcgc tagactccga aacatgacc      1380
aagagtcacc agaacttgtg caccaagggt caggtagtaa gtggccagta ccggatgctc     1440
gcaaagcatg ggggctacgt gtggctggag acccagggga cggtcatcta caaccctcgc     1500
aacctgcagc cccagtgcat catgtgtgtc aactacgtcc tgagtgagat tgagaagaat     1560
gacgtggtgt tctccatgga ccagactgaa tccctgttca gccccacct gatggccatg      1620
aacagcatct ttgatagcag tggcaagggg gctgtgtctg agaagagtaa cttcctattc     1680
accaagctaa aggaggagcc cgaggagctg gcccagctgg ctcccacccc aggagacgcc     1740
atcatctctc tggatttcgg gaatcagaac ttcgaggagt cctcagccta tggcaaggcc     1800
atcctgcccc cgagccagcc atgggccacg gagttgagga ccacagcac ccagagcgag      1860
gctgggagcc tgcctgcctt caccgtgccc caggcagctg ccccgggcag caccacccccc    1920 (?)
agtgccacca gcagcagcag cagctgctcc acgcccaata gccctgaaga ctattacaca     1980
tctttggata cgacctgaa gattgaagtg attgagaagc tcttcgccat ggacacagag      2040 (?)
gccaaggacc aatgcagtac ccagacggat ttcaatgagc tggacttgga gacactggca     2100
ccctatatcc ccatggacgg ggaagacttc agctaagcc ccatctgccc cgaggagcgg      2160
ctcttggcgg agaacccaca gtccaccccc cagcactgct tcagtgccat gacaaacatc     2220
ttccagccac tggcccctgt agccccgcac agtcccttcc tcctggacaa gtttcagcag     2280
cagctggaga gcaagaagac agagcccgag caccggccca tgtcctccat ctttcttgat     2340
gccggaagca agcatccct gccaccgtgc tgtggccagg ccagcacccc tctctcttcc      2400
atgggggca gatccaatac ccagtggccc ccagatccac cattacattt tgggcccaca     2460
aagtgggccg tcggggatca gcgcacagag ttcttgggag cagcgccgtt ggggccccct    2520
gtctctccac cccatgtctc cacctt caag acaaggtctg caaagggttt tggggctcga   2580 (?)
ggcccagacg tgctgagtcc ggccatggta gccctctcca acaagctgaa gctgaagcga     2640
cagctggagt atgaagagca agccttccag gacctgagcg gggggaccc acctggtggc      2700
agcacctcac atttgatgtg gaaacggatg aagaacctca ggggtgggag ctgccctttg    2760
atgccggaca agccactgag cgcaaatgta cccaatgata gttcacccca aaaccccatg     2820
aggggcctgg gccatccct gagacatctg ccgctgccac agcctccatc tgccatcagt     2880
cccggggaga acagcaagag caggttcccc ccacagtgct acgccaccca gtaccaggac     2940
tacagcctgt cgtcagccca aaggtgtca ggcatggcaa gccggctgct cgggccctca     3000
tttgagtcct acctgctgcc cgaactgacc agatatgact gtgaggtgaa cgtgcccgtg     3060
ctgggaagct ccacgctcct gcaaggaggg gacctcctca gagccctgga ccaggccacc     3120
tgagccaggc cttctacctg gcagcacct ctgccgacgc cgtcccacca gcttcactct      3180
ctccgtctgt ttttgcaact aggtatttct aacgccagca cactatttac aagatggact    3240
```

```
tacctggcag acttgcccag gtcaccaagc agtggccttt ttctgagatg ctcactttat      3300
tatccctatt tttaaagtac acaattgttt tacctgttct gaaatgttct taaattttgt      3360 aggattttt tcctccccac cttcaatgac ttctaattta tattatccat aggtttctct       3420
ccctccttct ccttctcaca cacaactgtc catactaaca agtttggtgc atgtctgttc      3480
ttctgtaggg agaagcttta gcttcatttt actaaaaaga ttcctcgtta ttgttgttgc      3540
caaagagaaa caaaaatgat tttgctttcc aagcttggtt tgtggcgtct ccctcgcaga      3600
gcccttctcg tttctttttt aaactaatca ccatattgta aatttcaggg ttttttttt      3660 tttgtttaag ctgactcttt gctctaattt tggaaaaaaa gaaatgtgaa gggtcaactc      3720
caacgtatgt ggttatctgt gaaagttgca cagcgtggct tttcctaaac tggtgttttt      3780
cccccgcatt tggtggattt tttattatta ttcaaaaaca taactgagtt ttttaaaaga      3840
ggagaaaatt tatatctggg ttaagtgttt atcatatata tgggtacttt gtaatatcta      3900
aaaacttaga aacggaaatg gaatcctgct cacaaaatca cttttaagatc ttttcgaagc      3960 tgttaatttt tcttagtgtt gtggacactg cagacttgtc cagtgctccc acggcctgta      4020
cggacactgt ggaaggcctc cctctgtcgg ctttttgcca tctgtgatat gccataggtg      4080
tgacaatccg agcagtggag tcattcagcg ggagcactgc gcgctatccc ctcacattct      4140
ctatgtacta tgtatgtatg tattattatt attgctgcca agagggtctg atggcacgtt      4200
gtggggtcgg ggggtggggc ggggaagtgc tctaactttt cttaaggttt tgttgctagc      4260
ccttcaagtg cactgagcta tgtgactcgg atggtctttc acacggcaca tttggacatt      4320
tccagaacta ccatgagatg gtttagacgg gaattcatgc aaatgagggg tcaaaaatgg      4380
tatagtgacc ccgtccacgt cctccaagct cacgaccttg gagccccgtg agctggact       4440 gaggaggagg ctgcacagcg ggagagcagc tggtccagac cagccctgca gcccccactc      4500
agccggcagc cagatggccc cgcaaggcct ccagggatgg cccctagcca caggccctgg      4560
ctgaggtctc tgggtcggtc agtgacatgt aggtaggaag cactgaaaat agtgttccca      4620
gagcactttg caactccctg ggtaagaggg acgacacctc tggttttca ataccaatta      4680 catggaactt ttctgtaatg ggtacaatga agaagtttct aaaaacacac acaaagcaca      4740
ttgggccaac tatttagtaa gcccggatag acttattgcc aaaaacaaaa aatagctttc      4800
aaaagaaatt taagttctat gagaaaattcc ttagtcatgg tgttgcgtaa atcatatttt     4860
agctgcacgg cattacccca cacagggtgg cagaacttga agggttactg acgtgtaaat      4920
gctggtattt gatttcctgt gtgtgttgcc ctggcattaa gggcattta cccttgcagt       4980 tttactaaaa cactgaaaaa tattccaagc ttcatattaa ccctacctgt caacgtaacg      5040
atttcatgaa cgttattata ttgtcgaatt cctactgaca acattataac tgtatgggag      5100 cttaactta taaggaaatg tattttgaca ctggtatctt attaaagtat tctgatccta       5160
ccactgaaaa aaaaaaaaaa aaaa                                            5184

<210> SEQ ID NO 81
<211> LENGTH: 3838
<212> TYPE: DNA
<213> ORGANISM: Homo sapiens

<400> SEQUENCE: 81
agtctcgggc ggcggtgtcc ggcgcgcggg cggcctgctg ggcgggctga agggttagcg       60
gagcacgggc aaggcggaga gtgacggagt cggcgagccc ccgcggcgac aggtaccggc      120
```

```
gccatggcca cggagatggg gcggccggcc gcggcgcccc gggagccgaa cgccctcctt    180
ccaggttctc tacttaaaag acaatgacta ctgatgaagg tgccaagaac aatgaagaaa    240
gccccacagc cactgttgct gagcagggag aggatattac ctccaaaaaa gacagggag     300 tattaaagat tgtcaaaaga gtggggaatg gtgaggaaac gccgatgatt ggagacaaag    360
tttatgtcca ttacaaagga aaattgtcaa atggaaagaa gtttgattcc agtcatgata    420
gaaatgaacc atttgtcttt agtcttggca aaggccaagt catcaaggca tgggacattg    480
gggtggctac catgaagaaa ggagagatat gccatttact gtgcaaacca gaatatgcat    540
atggctcggc tggcagtctc cctaaaattc cctcgaatgc aactctcttt tttgagattg    600
agctccttga tttcaaagga gaggatttat ttgaagatgg aggcattatc cggagaacca    660
aacggaaagg agagggatat tcaaatccaa acgaaggagc aacagtagaa atccacctgg    720
aaggccgctg tggtggaagg atgtttgact gcagagatgt ggcattcact gtgggcgaag    780
gagaagacca cgacattcca attggaattg acaaagctct ggagaaaatg cagcgggaag    840
aacaatgtat tttatatctt ggaccaagat atggttttgg agaggcaggg aagcctaaat    900
ttggcattga acctaatgct gagcttatat atgaagttac acttaagagc ttcgaaaagg    960
ccaaagaatc ctgggagatg gataccaaag aaaaattgga gcaggctgcc attgtcaaag   1020
agaagggaac cgtatacttc aagggaggca aatacatgca ggcggtgatt cagtatggga   1080
agatagtgtc ctggttagag atggaatatg gtttatcaga aaaggaatcg aaagcttctg   1140
aatcatttct ccttgctgcc tttctgaacc tggccatgtg ctacctgaag cttagagaat   1200
acaccaaagc tgttgaatgc tgtgacaagg cccttggact ggacagtgcc aatgagaaag   1260
gcttgtatag gaggggtgaa gcccagctgc tcatgaacga gtttgagtca gccaagggtg   1320
actttgagaa agtgctggaa gtaaaccccc agaataaggc tgcaagactg cagatctcca   1380
tgtgccagaa aaaggccaag gagcacaacg agcgggaccg caggatatac gccaacatgt   1440
tcaagaagtt tgcagagcag gatgccaagg aagaggccaa taaagcaatg ggcaagaaga   1500
cttcagaagg ggtcactaat gaaaaaggaa cagacagtca agcaatggaa gaagagaaac   1560
ctgagggcca cgtatgacgc cacgccaagg agggaagagt cccagtgaac tcggcccctc   1620
ctcaatgggc tttcccccaa ctcaggacag aacagtgttt aatgtaaagt tgttatagt    1680 ctatgtgatt ctggaagcaa atggcaaaac cagtagcttc ccaaaaacag ccccctgct    1740 gctgcccgga gggttcactg agggtggca cgggaccact ccaggtggaa caaacagaaa   1800
tgactgtggt gtgagggag tgagccagca gcttaagtcc agctcatttc agtttctatc    1860
aaccttcaag tatccaattc agggtccctg gagatcatcc taacaatgtg ggctgttag    1920 gttttacctt tgaactttca tagcactgca gaaacctta aaaaaaat gcttcatgaa     1980 tttctccttt cctacagttg ggtagggtag gggaaggagg ataagctttt gttttttaa    2040 tgactgaagt gctataaatg tagtctgttg cattttaac caacagaacc cacagtagag    2100
gggtctcatg tctccccagt tccacagcag tgtcacagac gtgaaagcca gaacctcaga   2160
ggccacttgc ttgctgactt agcctcctcc caaagtcccc ctcctcagcc agcctccttg    2220
tgagagtggc tttctaccac acacagcctg tccctggggg agtaattctg tcattcctaa   2280
aacacccttc agcaatgata atgagcagat gagagtttct ggattagctt ttcctatttt   2340
cgatgaagtt ctgagatact gaaatgtgaa aagagcaatc agaattgtgc ttttctccc    2400 ctcctctatt ccttttaggg aataatattc aatacacagt acttcctccc agcattgcta    2460
ctgctcagct tcttctttca ttctaatcct tgctattaag aatttaagac ttgtgcttac    2520
```

```
aatatttttg acctggagtg gatctattta catagtcatt taggatccat gcagctttt     2580 ttgtctttt  aagattattg gctcataagc atatgtatac tggtttatgg aactttattt    2640
acactcctct atcatgcaaa aaatttga   cttttagta  ctaagcttaa ttttaaaaa    2700 caaatctgt  agggttgaca aataaatagt tgctcttcta cactaggggt ttcacctgca    2760
ggtttgacac gcagttgctc gcttttcctg ccctgtcaag cttctctgtt ctggcgtgag    2820
ttgtgaaaga gttaagaca  gcttcccatg ccggtacaca gccagtagcc taaatctcca    2880
gtacttgagc tgaccattga actagggcaa gtcttaaatg tgtacatgta gttgaatttc    2940
agtccttacg ggtaaacaga ttgagcatgg ctctctattc cctcagccta agaaacactc    3000
atgggaatgc atttggcaac ccaaggaacc atttgcttaa acctggaaca tctcacctt    3060 ttaaatccta aaaacactg  gcagttatat tttaaattag ttttattt  tatgatggtt    3120 ttatcaaaag actttatta  ttagattggg acccccttca aacctaaaaa tcaagttatt    3180 tcctttata  atactttct  tccccatgga acaaatggga tcaatttgtg agttttttcc    3240
tttaatgata actaaaatcc ctctaatttc tcatttatgc ttttgtcttt tttatgaaat    3300 atttcttta  aaagcccag  tctcacctac gaaatatgaa gagcaaaagc tgatttttgct   3360 tacttgctaa actgttggga aagctctgta gagcatggtt ccagtgaggc caagattgaa    3420
atttgatact aaaaaggcca cctagctttt tgcagataac aaacaagaaa gctattccaa    3480
gactcagatg atgccagctg tctcccacgt gtgtattatg gttcaccagg gggaactggc    3540
aaaagtgtgt gtggggaggg gaagggtgtg tgagtggttc tgagcaaata actcagggt    3600 gcccattacc actcaagaag acacttcacg tattcttgta tcaaattcaa taatcttaaa    3660
caatttgtgt agaagtccac agacatcttt caaccacctt ttaggctgca tatggattgc    3720
caagtcagca tatgaggaat taaagacatt gtttttaaaa aaaaaaaatc atttagatgc    3780
acttttttgt gtgttcttta aataaatcca aaaaaatgt  gacttccaaa aaaaaaa      3838
```

<210> SEQ ID NO 82
<211> LENGTH: 2207
<212> TYPE: DNA
<213> ORGANISM: Homo sapiens

<400> SEQUENCE: 82

```
cacttcctcc ccagacaggg gtagtgcgag gccgggcaca gccttcctgt gtggttttac      60
cgcccagaga gcgtcatgga cctggggaaa ccaatgaaaa gcgtgctggt ggtggctctc     120
cttgtcattt tccaggtatg cctgtgtcaa gatgaggtca cggacgatta catcggagac     180
aacaccacag tggactacac tttgttcgag tctttgtgct ccaagaagga cgtgcggaac     240
tttaaagcct ggttcctccc tatcatgtac tccatcattt gtttcgtggg cctactgggc     300
aatgggctgg tcgtgttgac ctatatctat ttcaagaggc tcaagaccat gaccgatacc     360
tacctgctca acctggcggt ggcagacatc ctcttcctcc tgaccctcc  cttctgggcc     420 tacagcgcgg ccaagtcctg ggtcttcggt gtccactttt gcaagctcat ctttgccatc     480
tacaagatga gcttcttcag tggcatgctc ctacttcttt gcatcagcat tgaccgctac     540
gtggccatcg tccaggctgt ctcagctcac cgccaccgtg cccgcgtcct tctcatcagc     600
aagctgtcct gtgtgggcat ctggatacta gccacagtgc tctccatccc agagctcctg     660
tacagtgacc tccagaggag cagcagtgag caagcgatgc gatgctctct catcacagag     720
catgtggagg cctttatcac catccaggtg gcccagatgg tgatcggctt tctggtcccc     780
```

```
ctgctggcca tgagcttctg ttaccttgtc atcatccgca ccctgctcca ggcacgcaac      840
tttgagcgca acaaggccat caaggtgatc atcgctgtgg tcgtggtctt catagtcttc      900
cagctgccct acaatggggt ggtcctggcc cagacggtgg ccaacttcaa catcaccagt      960
agcacctgtg agctcagtaa gcaactcaac atcgcctacg acgtcaccta cagcctggcc     1020
tgcgtccgct gctgcgtcaa ccctttcttg tacgccttca tcggcgtcaa gttccgcaac     1080
gatctcttca agctcttcaa ggacctgggc tgcctcagcc aggagcagct ccggcagtgg     1140
tcttcctgtc ggcacatccg gcgctcctcc atgagtgtgg aggccgagac caccaccacc     1200
ttctccccat aggcgactct tctgcctgga ctagagggac ctctcccagg gtccctgggg     1260
tggggatagg gagcagatgc aatgactcag gacatccccc cgccaaaagc tgctcaggga     1320
aaagcagctc tccccctcaga gtgcaagccc ctgctccaga agatagcttc accccaatcc     1380
cagctacctc aaccaatgcc aaaaaagac agggctgata agctaacacc agacagacaa      1440
cactgggaaa cagaggctat tgtccccttaa accaaaaact gaaagtgaaa gtccagaaac    1500
tgttcccacc tgctggagtg aaggggccaa ggagggtgag tgcaagggc gtgggagtgg      1560
cctgaagagt cctctgaatg aaccttctgg cctcccacag actcaaatgc tcagaccagc     1620
tcttccgaaa accaggcctt atctccaaga ccagagatag tggggagact tcttggcttg     1680
gtgaggaaaa gcggacatca gctggtcaaa caaactctct gaaccccttcc ctccatcgtt    1740
ttcttcactg tcctccaagc cagcgggaat ggcagctgcc acgccgccct aaaagcacac     1800
tcatcccctc acttgccgcg tcgccctccc aggctctcaa caggggagag tgtggtgttt     1860
cctgcaggcc aggccagctg cctccgcgtg atcaaagcca cactctgggc tccagagtgg    1920
ggatgacatg cactcagctc ttggctccac tgggatggga ggagaggaca agggaaatgt    1980
caggggcggg gagggtgaca gtggccgccc aaggcccacg agcttgttct ttgttctttg    2040
tcacagggac tgaaaacctc tcctcatgtt ctgctttcga ttcgttaaga gagcaacatt    2100
ttacccacac acagataaag ttttcccttg aggaaacaac agctttaaaa gaaaagaaa      2160
aaaaagtct ttggtaaatg gcaaaaaaaa aaaaaaaaa aaaaaaa                     2207
```

<210> SEQ ID NO 83
<211> LENGTH: 838
<212> TYPE: DNA
<213> ORGANISM: Homo sapiens

<400> SEQUENCE: 83

```
ctcgcgagat ttgacctctc gtccctgaga ggcgggtggg tgttagttca gagggttatg       60
ggagggctct ggcgtcctgg atggaggtgc gttcctttct gtggctggcg ctggatccac      120
cctgggtctc caaccagggc tgcagagagg gtagagccgt tcttaggcc agagtggagt       180
gggacaggag gtgccgagag aggactgagg tggcttggga catggaagcg ctgcagcctt      240
cgagcccggc atccagcatt gcagccgccg cggcggccta agagctcgaa ccctttcaca      300
cgcgcgcagg aggaggagcg gcggcggcag aacaagacga ccctcactta cgtggccgct     360
gtcgccgtgg gcatgctggg ggcgtcctac gctgccgtac ccctttatcg gctctattgc     420
cagactactg gacttggagg atcagcagtt gcaggtcatg cctcagacaa gattgaaaac     480
atggtgcctg ttaaagatcg aatcattaaa attagcttta atgcagatgt gcatgcaagt     540
ctccagtgga actttagacc tcagcaaaca gaaatatatg tggtgccagg agagactgca     600
ctggcgtttt acagagctaa gaatcctact gacaaaccag taattggaat ttctacatac     660
aatattgttc catttgaagc tggacagtat ttcaataaaa tacaggtatt gtcttccagg     720
```

```
cttcaaagct gcacagagtc tacgttttag agagttggca cctttgatgt ggtagtgagc    780
tgatcatcca ctttcttcta aaataaagag aagaaaatgg ccagtaaaaa aaaaaaaa     838

<210> SEQ ID NO 84
<211> LENGTH: 586
<212> TYPE: DNA
<213> ORGANISM: Homo sapiens

<400> SEQUENCE: 84
aaacactctg tgtggctcct cggctttgac agagtgcaag acgatgactt gcaaaatgtc    60
gcagctggaa cgcaacatag agaccatcat caacaccttc caccaatact ctgtgaagct   120
ggggcaccca gacaccctga accagggggga attcaaagag ctggtgcgaa agatctgca   180
```
(Note: line at 180 contains "ggggcaccca gacaccctga accagggggga attcaaagag ctggtgcgaa agatctgca")

```
aaattttctc aagaaggaga ataagaatga aaaggtcata gaacacatca tggaggacct   240
ggacacaaat gcagacaagc agctgagctt cgaggagttc atcatgctga tggcgaggct   300
aacctgggcc tcccacgaga agatgcacga gggtgacgag ggccctggcc accaccataa   360
gccaggcctc ggggagggca ccccctaaga ccacagtggc caagatcaca gtggccacgg   420
ccacggccac agtcatggtg gccacggcca cagccactaa tcaggaggcc aggcacccct   480
gcctctaccc aaccagggcc ccggggcctg ttatgtcaaa ctgtcttggc tgtggggcta   540
ggggctgggg ccaaataaag tctcttcctc caagtcaaaa aaaaaa                  586

<210> SEQ ID NO 85
<211> LENGTH: 1567
<212> TYPE: DNA
<213> ORGANISM: Homo sapiens

<400> SEQUENCE: 85
cgccccaccc gcgagccgca gccgcggccc cacagcttct ggggctgggg ccccggcagc    60
cgggcaggcc ggcctgacct cgacctccgc cgtgcgggcc cgaccggtga gtccagcccg   120
gcagtcgcag gacccggccg ccagcctctc cctccacctc tccctgcccc cagcgccagg   180
cgcgggctgc gctcggtggc ggcggcgggg ccctcaggcg gccatggcgg caggcgccgg   240
ggccgggtcc gcgccgcgct ggctgagggc gctgagcgag ccgctgagcg cggcgcagct   300
gcggcgactg gaggagcacc gctacagcgc ggcgggcgtc tcgctgctcg agccgccgct   360
gcagctctac tggacctggc tgctccagtg gatcccgctc tggatggccc ccaactccat   420
caccctgctg gggctcgccg tcaacgtggt caccacgctc gtgctcatct cctactgtcc   480
cacggccacc gaagaggcac catactggac ataccttta tgtgcactgg actttttat    540 ttaccagtca ctggatgcta ttgatgggaa acaagccaga agaacaaact cttgttcccc   600
tttaggggag ctctttgacc atggctgtga ctctcttttcc acagtattta tggcagtggg   660
agcttcaatt gccgctcgct taggaactta tcctgactgg ttttttttct gctcttttat   720
tgggatgttt gtgttttatt gcgctcattg gcagacttat gtttcaggca tgttgagatt   780
tggaaaagtg gatgtaactg aaattcagat agctttagtg attgtctttg tgttgtctgc   840
atttggagga gcaacaatgt gggactatac gattcctatt ctagaaataa aattgaagat   900
ccttccagtt cttggatttc taggtggagt aatattttcc tgttcaaatt atttccatgt   960
tatcctccat ggtggtgttg gcaagaatgg atccactata gcaggcacca gtgtcttgtc   1020
acctggactc cacataggac taattattat actggcaata atgatctata aaagtcagc   1080 aactgatgtg tttgaaaagc atccttgtct ttatatccta atgtttggat gtgtctttgc   1140
```

```
taaagtctca caaaaattag tggtagctca catgaccaaa agtgaactat atcttcaaga    1200 cactgtctt ttggggccag gtcttttgtt tttagaccag tactttaata actttataga    1260
cgaatatgtt gttctatgga tggcaatggt gatttcttca tttgatatgg tgatatactt    1320
tagtgctttg tgcctgcaaa tttcaagaca ccttcatcta aatatattca agactgcatg    1380
tcatcaagca cctgaacagg ttcaagttct tcttcaaag agtcatcaga ataacatgga    1440
ttgaagagac ttccgaacac ttgctatctc ttgctgctgc tgtttcatgg aaggagatat    1500
taaacatttg tttaattttt atttaagtgt tatacctatt tcagcaaata aaatatttca    1560
ttgctta                                                              1567
```

<210> SEQ ID NO 86
<211> LENGTH: 5208
<212> TYPE: DNA
<213> ORGANISM: Homo sapiens

<400> SEQUENCE: 86

```
cttactcatt tgtgtttatt cttggactta tcctgacata atggggtttt tttaattata      60
gattcacact gcatttattc atcaccctg tcctctcatc cataactcaa atttactacc     120
agcaacacaa aatacaaaga tgtgtccagt ttcactacag ctcttcgcgt ttacaagtgt     180
cgagcgcttg cttcggaac gcccttgtga ttggccgagc caatgccagt gacatcaacc     240
aacttacttt tgattggaag gctggttgct gggactgtag cgtttgcagg aagtcactta     300
actgtttggg agctggaaaa ccgaagctga agttctcttt tgccatagga acgagcgcaa     360
ctgactagga aagatgtgtc ccaaagctcc gcaagctgga acgtgagcca ggaggcccgg     420
accggccacg ggaccgcgag gcactccgaa agtgtgcggc tgccccttcc ctgcctccca     480
gctgttaccc ttttaaatgt cagtgttcga ggctgtaggg gtagcacgag gcagcgaaac     540
ggaacagtcg gattggccgc acgcctcagt tctagacgca cctctccacc gaaggccgtt     600
ctgactggca gggggagaaa gtaaacagag ttgaatcacc ctcccactg gccaattgga     660 gggggtttgg tttgtgacgt gatgggattc tgcgaaattg ttactgagca agagaatgcc     720
ggaacggtgc ggaccggccg gagcagggt tcagaagccg tcagtggact cgggaaaaag     780
tgtctcttag acctggcgct cggcgggacc ctcgccaccc gcgtcggggt gatcgggtga     840
atgtcctggg gctttggctc gacggcgagg cggccgaggg cgtgcacctc tcttgcagtt     900
tcctctccca gcgcctcggg ggcgttttca gtcgaataaa cttgcgaccg ccacgtgtgg     960
catctttcca agggagccgg ctcagagggg ccggcgcgcc cgtcggggga tcgcggccgg    1020
cgcggggcag gggcggcggc tagaggcggc ggcgcggcgg agcccggggc cgtggatgct    1080
gcgtgcggag gcgctgccgg ttacgtaaag atgaggggct gaggtcgcct cggcgctcct    1140
gcgagtcgga agcgcccgc gcccccgccc ccttggccgc cgcgccgtgc cgcgccgcgc    1200
cgcgctcgtc gtccgaggcc agggcagggc gagccgaacc tccgcagcca ccgccaagtt    1260
tgtccgcgcc gcctgggctg ccgtcgcccg caccatgtcc gcggccgcct acatggactt    1320
cgtggctgcc cagtgtctgg tttccatttc gaaccgcgct gcggtgccgg agcatgggt    1380 cgctccggac gccgagcggc tgcgactacc tgagcgcgag gtgaccaagg agcacggtga    1440
cccgggggac acctggaagg attactgcac actggtcacc atcgccaaga gcttgttgga    1500
cctgaacaag taccgaccca tccagacccc ctccgtgtgc agcgacagtc tggaaagtcc    1560
agatgaggat atgggatccg acagcgacgt gaccaccgaa tctgggtcga gtccttccca    1620
cagcccggag gagagacagg atcctggcag cgcgcccagc ccgctctccc tcctccatcc    1680
```

```
tggagtggct gcgaagggga aacacgcctc cgaaaagagg cacaagtgcc cctacagtgg   1740
ctgtgggaaa gtctatggaa aatcctccca tctcaaagcc cattacagag tgcatacagg   1800
tgaacggccc tttccctgca cgtggccaga ctgccttaaa aagttctccc gctcagacga   1860
gctgacccgc cactaccgga cccacactgg ggaaaagcag ttccgctgtc cgctgtgtga   1920
gaagcgcttc atgaggagtg accacctcac aaagcacgcc cggcggcaca ccgagttcca   1980
ccccagcatg atcaagcgat cgaaaaaggc gctggccaac gctttgtgag gtgctgcccg   2040
tggaagccag ggagggatgg accccgaaag gacaaaagta ctcccaggaa acagacgcgt   2100
gaaaactgag ccccagaaga ggcacacttg acggcacagg aagtcactgc tctttggtca   2160
atattctgat tttcctctcc ctgcattgtt tttaaaaagc acattgtagc ctaagatcaa   2220
agtcaacaac actcggtccc cttgaagagg caactctctg aacccgtctc tgactgttgg   2280
agggaaggca aatgcttttg ggttttttgg ttttttgtttt tgttttttttt tctcctttta   2340 tttttttgcg ggggagggta gggagtgggg gggggggagg ggggtaaggc caagactggg   2400
gtagaatttt aaagattcaa cactggtgta catatgtccg ctgggtgagt tgacctgtgg   2460
cctcgcacag tgattctggg cccttttatgc ttgctgtctc tcagaattgt tttcttacct   2520
tttaatgtaa tgacgagtgt gcttcagttt gtttagcaaa accactctct tgaatcacgt   2580
taacttttga gattaaaaaa aaaaacgcca tagcacagct gtcttttatgc aagcaagagc   2640 acatctactc cagcatgatc tgtcatctaa agacttgaaa acaaaaaaca gttacttata   2700
gtcaatgggt aagcagagtc tgaatttata ctaatcaaga caaaccttttg aaaggttaca   2760 ctaagtacag aacttttaaa ccttgctttg tatgagttgt acttttttgaa cataagctgc   2820 acttttattt tctaatgcag aggatgaata agttaaatac atgctttgag gatagaagca   2880
gatgttctgt ttggcaccac gttataatct gcttatttta caatatacac gtttccctaa   2940
gaaatcatgg cagagatgtg agggcagaat atacacaaca gatgctgaag gagaaggagg   3000
gtagtgtttt gcaaaagaaa aagaaaagaa ccaacagaat tttaactcta ttaacttttc   3060 caaatttttcc tatgctttta gttaacatca ttattgtatc ctaatgccac taggggagag   3120
agcttttgac tctgttgggt tttatttgaa tgtgtgcata acagtaatga gatctggaaa   3180
cacctatttt ttggggaaaa aggtttgttg gtctccttcc tgtgttccta caaaactccc   3240
actctcaggt gcaagagtta tgtagaagga agggagctg aaataggaac agaaaaatca   3300 accccctataа ctagtgaaca ccaagggaaa ataccacaat gatttcagag gagactctgc   3360
aaaatcgtcc cttgtggaga atgcaggcaa catggaatac taggaatgaa atcacatcac   3420
tgtatctttt acatcaatag cctcaccact aatatatctt gtatctaggt gtctataatg   3480
gctgaaacca ctacatccat ctatgccatt tacctgaaaa cttaactgtg gcctttatga   3540
ggccagaaaa gtgaactgag ttttcgtagt taagacctca aatgagggga gtcagcagtg   3600 atcatgggg aaatgtttac attttttttt tcttcagaag taacgctttc tgatgatttt   3660
atctgatatt taaaacaggg agctatggtg cactctagtt tatacttgcg ctctgaaatg   3720
tgtaaacata gggtgcctac ctattcacc tgacccatac tcgtttctga ttcagaatca   3780
gtgtgggctc ctgcagtggg cgcgggtcac ggctgactcc aacttccaat acaacagcca   3840
tcactagcac agtgtttttt tgtttaacca acgtagttgt attagtagtt ctataaagag   3900
aactgctttt aacattaggg actgggagca gtccatggga taaaaaggaa agtgttttct   3960
cacgagaaaa catgtcagga aaataaaga acactttcta cctctgtttc agattttttga   4020
```

```
aacacttatt ttaaaccaaa ttttaatttc tgtgtccaaa ataagtttta aggacatctg    4080
ttcttccata cgaaataggt taggctgcct atttctcact gagctcatgg aatggttctg    4140
cttatgatac tctgcacgct gccttttagt gagtgaggag tttggggttg cctagcaact    4200
tgctaacttg taaaaagtca tctttccctc acagaaagaa acgaaagaaa gcaaagcaaa    4260
gtcagtgaaa gacaatcttt atagtttcag gagtaaatct aaatgtggct tttgtcaagc    4320
acttagatgg atataaatgc agcaacttgt tttaaaaaaa tgcacaattt acttcccaaa    4380
aaagttgtta cttgcctttt caagttgttg acaaacacac atttgatatt ctcttatatg    4440
ttatagtaat gtaacgtata aactcaagcc tttttattct ttgtgattaa atcctgtttt    4500
aaaatgtcac aaaacaggaa ccagcattct aattagattt actatatcaa gatatggttc    4560
aaataggact actagagttc attgaacact aaaactatga aacaattact ttttatatta    4620
aaaagaccat ggatttaact tatgaaaatc caaatgcagg atagtaattt ttgtttactt    4680
ttttaaccaa actgaatttt tgaaagacta ttgcaggtgt ttaaaagaa agaaaagttg     4740 ttttatctaa tactgtaagt agttgtcata ttctggaaaa tttaatagtt ttagagttaa    4800
gatatctcct ctctttggtt agggaagaag aaagcccttc accattgtgg aatgatgccc    4860
tggctttaag gtttagctcc acatcatgct tctcttgaga attctatttg gtagttacaa    4920
ttacagaaac tgattagttt gtcagtttgc agatagattt agcacagtac tcatcactcg    4980
gatagattga gatgttcttt cacatcagat gatctgtaac actgtaagat actgatcttt    5040
acaactgttt aatcagtttt atttttgtac agtattagtg acctaagtta ttttgctgtc    5100 ccgttttgt aaatcaaatg aaattataaa agaggattct gacagtaggt attttgtaca     5160
tatgtatata tgttgtccaa ataaaaataa taaatgataa agactgaa                 5208

<210> SEQ ID NO 87
<211> LENGTH: 2535
<212> TYPE: DNA
<213> ORGANISM: Homo sapiens

<400> SEQUENCE: 87
gcactgcctc tggcacctgg ggcagccgcg cccgcggagt tttccgcccg gcgctgacgg      60
ctgctgcgcc cgcggctccc cagtgccccg agtgccccgc gggccccgcg agcgggagtg     120
ggacccagcc cctaggcaga acccaggcgc cgcgcccggg acgcccgcgg agagagccac     180
tcccgcccac gtcccatttc gcccctcgcg tccggagtcc ccgtggccag gtgtgtgtct     240
ggggaagaga cttacagaag tggagttgct gagtcaaaga tctaaccatg agctaccctg     300
gctatccccc gccccccaggt ggctacccac cagctgcacc aggtggtggt ccctggggag    360
gtgctgccta ccctcctccg cccagcatgc ccccatcgg gctggataac gtggccacct      420
atgcggggca gttcaaccag gactatctct cgggaatggc ggccaacatg tctgggacat     480
ttggaggagc caacatgccc aacctgtacc ctggggcccc tggggctggc tacccaccag     540 tgcccctgg cggctttggg cagccccct ctgcccagca gctgttcct ccctatggga       600 tgtatccacc cccaggagga aacccacccct ccaggatgcc ctcatatccg ccatacccag    660
gggcccctgt gccgggccag cccatgccac ccccgacaa gcagccccca ggggcctacc     720
ctgggcagcc accagtgacc taccctggtc agcctccagt gccactccct gggcagcagc     780
agccagtgcc gagctaccca ggatacccgg ggtctgggac tgtcaccccc gctgtgcccc     840
caacccagtt tggaagccga ggcaccatca ctgatgctcc cggctttgac cccctgcgag     900
atgccgaggt cctgcggaag gccatgaaag cttcgggac ggatgagcag gccatcattg      960
```

```
actgcctggg gagtcgctcc aacaagcagc ggcagcagat cctactttcc ttcaagacgg    1020
cttacggcaa ggatttgatc aaagatctga aatctgaact gtcaggaaac tttgagaaga    1080
caatcttggc tctgatgaag accccagtcc tctttgacat ttatgagata aaggaagcca    1140
tcaaggtggt tggcactgat gaagcctgcc tgattgagat cctcgcttcc cgcagcaatg    1200
agcacatccg agaattaaac agagcctaca agcagaatt caaaaagacc ctggaagagg    1260
ccattcgaag cgacacatca gggcacttcc agcggctcct catctctctc tctcagggaa    1320
accgtgatga agcacaaac gtggacatgt cactcgccca gagagatgcc caggagctgt    1380
atgcggccgg ggagaaccgc ctgggaacag acgagtccaa gttcaatgcg gttctgtgct    1440
cccggagccg ggcccacctg gtagcagttt tcaatgagta ccagagaatg acaggccggg    1500
acattgagaa gagcatctgc cgggagatgt ccggggacct ggaggagggc atgctggccg    1560
tggtgaaatg tctcaagaat accccagcct tctttgcgga gaggctcaac aaggccatga    1620
gggggggcag aacaaaggac cggaccctga ttcgcatcat ggtgtctcgc agcgagaccg    1680
acctcctgga catcagatca gagtataagc ggatgtacgg caagtcgctg taccacgaca    1740
tctcgggaga tacttcaggg gattaccgga agattctgct gaagatctgt ggtggcaatg    1800
actgaacagt gactggtggc tcacttctgc ccacctgccg gcaacaccag tgccaggaaa    1860
aggccaaaag aatgtctgtt tctaacaaat ccacaaatag ccccgagatt caccgtccta    1920
gagcttaggc ctgtcttcca cccctcctga cccgtatagt gtgccacagg acctgggtcg    1980
gtctagaact ctctcaggat gccttttcta ccccatccct cacagcctct tgctgctaaa    2040
atagatgttt catttttctg actcatgcaa tcattcccct ttgcctgtgg ctaagacttg    2100
gcttcatttc gtcatgtaat tgtatatttt tatttggagg catattttct tttcttacag    2160
tcattgccag acagaggcat acaagtctgt ttgctgcata cacatttctg gtgagggcga    2220
ctgggtgggt gaagcaccgt gtcctcgctg aggagagaaa gggaggcgtg cctgagaagg    2280
tagcctgtgc atctggtgag tgtgtcacga gctttgttac tgccaaactc actccttttt    2340
agaaaaaaca aaaaaaaagg gccagaaagt cattccttcc atcttccttg cagaaaccac    2400
gagaacaaag ccagttccct gtcagtgaca gggcttcttg taatttgtgg tatgtgcctt    2460
aaacctgaat gtctgtagcc aaaacttgtt tccacattaa gagtcagcca gctctggaat    2520
ggtctggaaa tgtca                                                     2535
```

<210> SEQ ID NO 88
<211> LENGTH: 7080
<212> TYPE: DNA
<213> ORGANISM: Homo sapiens

<400> SEQUENCE: 88

```
gagctagcgc tcaagcagag cccagcgcgg tgctatcgga cagagcctgg cgagcgcaag      60
cggcgcgggg agccagcggg gctgagcgcg gccagggtct gaacccagat ttcccagact     120
agctaccact ccgcttgccc acgccccggg agctcgcggc gcctggcggt cagcgaccag     180
acgtccgggg ccgctgcgct cctggcccgc gaggcgtgac actgtctcgg ctacagaccc     240
agagggagca cactgccagg atgggagctg ctggaggga ggacttcctc ttcaaggcca     300
tgctgaccat cagctggctc actctgacct gcttccctgg ggccacatcc acagtggctg     360
ctgggtgccc tgaccagagc cctgagttgc aaccctggaa ccctggccat gaccaagacc     420
accatgtgca tatcggccag ggcaagacac tgctgctcac ctcttctgcc acggtctatt     480
```

```
ccatccacat ctcagaggga ggcaagctgg tcattaaaga ccacgacgag ccgattgttt    540
tgcgaacccg gcacatcctg attgacaacg gaggagagct gcatgctggg agtgccctct    600 gcccttttcca gggcaatttc accatcattt tgtatggaag ggctgatgaa ggtattcagc   660
cggatcctta ctatggtctg aagtacattg gggttggtaa aggaggcgct cttgagttgc    720
atggacagaa aaagctctcc tggacatttc tgaacaagac ccttcaccca ggtggcatgg    780
cagaaggagg ctattttttt gaaaggagct ggggccaccg tggagttatt gttcatgtca    840
tcgaccccaa atcaggcaca gtcatccatt ctgaccggtt tgacacctat agatccaaga    900
aagagagtga acgtctggtc cagtatttga acgcggtgcc cgatggcagg atcctttctg    960
ttgcagtgaa tgatgaaggt tctcgaaatc tggatgacat ggccaggaag gcgatgacca   1020
aattgggaag caaacacttc ctgcaccttg gatttagaca cccttggagt tttctaactg   1080
tgaaaggaaa tccatcatct tcagtggaag accatattga atatcatgga catcgaggct   1140
ctgctgctgc ccgggtattc aaattgttcc agacagagca tggcgaatat ttcaatgttt   1200
ctttgtccag tgagtgggtt caagacgtgg agtggacgga gtggttcgat catgataaag   1260
tatctcagac taaaggtggg gagaaaattt cagacctctg gaaagctcac ccaggaaaaa   1320
tatgcaatcg tcccattgat atacaggcca ctacaatgga tggagttaac ctcagcaccg   1380
aggttgtcta caaaaaaggc caggattata gtttgcttg ctacgaccgg ggcagagcct    1440
gccggagcta ccgtgtacgg ttcctctgtg gaagcctgt gaggcccaaa ctcacagtca    1500
ccattgacac caatgtgaac agcaccattc tgaacttgga ggataatgta cagtcatgga   1560
aacctggaga taccctggtc attgccagta ctgattactc catgtaccag gcagaagagt   1620
tccaggtgct tccctgcaga tcctgcgccc caaccaggt caaagtggca gggaaaccaa    1680
tgtacctgca catcggggag gagatagacg gcgtggacat gcgggcggag gttgggcttc   1740
tgagccggaa catcatagtg atgggggaga tggaggacaa atgctacccc tacagaaacc   1800
acatctgcaa tttctttgac ttcgatacct ttggggggcca tcaagtttt gctctgggat    1860 ttaaggcagc acacttggag ggcacggagc tgaagcatat gggacagcag ctggtgggtc   1920
agtacccgat tcacttccac ctggccggta tgtagacga aagggggagt tatgaccccac   1980 ccacatacat cagggaccct ccatccatc atacattctc tcgctgcgtc acagtccatg    2040
gctccaatgg cttgttgatc aaggacgttg tgggctataa ctctttgggc cactgcttct   2100
tcacggaaga tgggccggag gaacgcaaca ctttttgacca ctgtcttggc ctccttgtca   2160
agtctggaac cctcctcccc tcggaccgtg acagcaagat gtgcaagatg atcacagagg   2220
actcctaccc ggggtacatc cccaagccca ggcaagactg caatgctgtg tccaccttct   2280
ggatggccaa tccaacaac aacctcatca actgtgccgc tgcaggatct gaggaaactg    2340
gattttggtt tatttttcac cacgtaccaa cgggcccctc cgtgggaatg tactccccag   2400
gttattcaga gcacattcca ctgggaaaat tctataacaa ccgagcacat tccaactacc   2460
gggctggcat gatcatagac aacggagtca aaaccaccga ggcctctgcc aaggacaagc   2520
ggccgttcct ctcaatcatc tctgccagat acagccctca ccaggacgcc gacccgctga   2580
agccccggga gccggccatc atcagacact tcattgccta caagaaccag gaccacgggg   2640
cctggctgcg cggcggggat gtgtggctgg acagctgccg gtttgctgac aatggcattg   2700
gcctgaccct ggccagtggt ggaacccttc cgtatgacga cggctccaag caagagataa   2760
agaacagctt gtttgttggc gagagtgcca acgtgggggac ggaaatgatg acaataggaa  2820
tctggggccc tggcggcttg gaccatagcg gaaggaccct ccctataggc cagaattttc   2880
```

```
caattagagg aattcagtta tatgatggcc ccatcaacat ccaaaactgc actttccgaa    2940
agtttgtggc cctggagggc cggcacacca gcgccctggc cttccgcctg aataatgcct    3000
ggcagagctg cccccataac aacgtgaccg gcattgcctt tgaggacgtt ccgattactt    3060
ccagagtgtt cttcggagag cctgggccct ggttcaacca gctggacatg gatgggata     3120 agacatctgt gttccatgac gtcgacggct ccgtgtccga gtaccctggc tcctacctca    3180
cgaagaatga caactggctg gtccggcacc cagactgcat caatgttccc gactggagag    3240
gggccatttg cagtgggtgc tatgcacaga tgtacattca agcctacaag accagtaacc    3300
tgcgaatgaa gatcatcaag aatgacttcc ccagccaccc tctttacctg gagggggcgc    3360
tcaccaggag cacccattac cagcaatacc aaccggttgt caccctgcag aagggctaca    3420
ccatccactg ggaccagacg gcccccgccg aactcgccat ctggctcatc aacttcaaca    3480
agggcgactg gatccgagtg gggctctgct acccgcgagg caccacattc tccatcctct    3540
cggatgttca caatcgcctg ctgaagcaaa cgtccaagac gggcgtcttc gtgaggacct    3600
tgcagatgga caaagtggag cagagctacc ctggcaggag ccactactac tgggacgagg    3660 actcaggggct gttgttcctg aagctgaaag ctcagaacga gagagagaag tttgctttct    3720
gctccatgaa aggctgtgag aggataaaga ttaaagctct gattccaaag aacgcaggcg    3780
tcagtgactg cacagccaca gcttacccca agttcaccga gagggctgtc gtagacgtgc    3840
cgatgcccaa gaagctcttt ggttctcagc tgaaaacaaa ggaccatttc ttggaggtga    3900
agatggagag ttccaagcag cacttcttcc acctctggaa cgacttcgct tacattgaag    3960
tggatgggaa gaagtacccc agttcggagg atggcatcca ggtggtggtg attgacggga    4020
accaagggcg cgtggtgagc cacacgagct caggaactc cattctgcaa ggcataccat     4080
ggcagctttt caactatgtg gcgaccatcc ctgacaattc catagtgctt atggcatcaa    4140
agggaagata cgtctcccaga ggcccatgga ccagagtgct ggaaaagctt ggggcagaca    4200
ggggtctcaa gttgaaagag caaatggcat tcgttggctt caaaggcagc ttccggccca    4260
tctgggtgac actggacact gaggatcaca aagccaaaat cttccaagtt gtgcccatcc    4320
ctgtggtgaa gaagaagaag ttgtgaggac agctgccgcc cggtgccacc tcgtggtaga    4380
ctatgacggt gactcttggc agcagaccag tggggatgg ctgggtcccc cagcccctgc     4440
cagcagctgc ctgggaaggc cgtgtttcag ccctgatggg ccaagggaag gctatcagag    4500
accctggtgc tgccacctgc ccctactcaa gtgtctacct ggagcccctg ggcggtgct     4560 ggccaatgct ggaaacattc actttcctgc agcctcttgg gtgcttctct cctatctgtg    4620
cctcttcagt gggggtttgg ggaccatatc aggagacctg ggttgtgctg acagcaaaga    4680
tccactttgg caggagccct gacccagcta ggaggtagtc tggagggctg gtcattcaca    4740
gatccccatg gtcttcagca gacaagtgag ggtggtaaat gtaggagaaa gagccttggc    4800
cttaaggaaa tctttactcc tgtaagcaag agccaacctc acaggattag gagctggggt    4860
agaactggct atccttgggg aagaggcaag ccctgcctct ggccgtgtcc acctttcagg    4920
agactttgag tggcaggttt ggacttggac tagatgactc tcaaaggccc ttttagttct    4980
gagattccag aaatctgctg catttcacat ggtacctgga acccaacagt tcatggatat    5040
ccactgatat ccatgatgct gggtgcccca gcgcacacgg gatggagagg tgagaactaa    5100
tgcctagctt gaggggtctg cagtccagta gggcaggcag tcaggtccat gtgcactgca    5160
atgccaggtg gagaaatcac agagaggtaa aatggaggcc agtgccattt cagaggggag    5220
```

```
gctcaggaag gcttcttgct tacaggaatg aaggctgggg gcattttgct gggggagat    5280 gaggcagcct ctggaatggc tcagggattc agccctccct gccgctgcct gctgaagctg    5340
gtgactacgg ggtcgcccctt tgctcacgtc tctctggccc actcatgatg gagaagtgtg    5400
gtcagagggg agcaatgggc tttgctgctt atgagcacag aggaattcag tccccaggca    5460
gccctgcctc tgactccaag agggtgaagt ccacagaagt gagctcctgc cttagggcct    5520
catttgctct tcatccaggg aactgagcac aggggggcctc caggagaccc tagatgtgct    5580
cgtactccct cggcctggga tttcagagct ggaaatatag aaaatatcta gcccaaagcc    5640
ttcattttaa cagatgggga aagtgagccc ccaagatggg aaagaaccac acagctaagg    5700
gagggcctgg ggagccccac cctagccctt gctgccacac acattgcct caacaaccgg    5760 ccccagagtg cccaggcact cctgaggtag cttctggaaa tggggacaag tcccctcgaa    5820
ggaaaggaaa tgactagagt agaatgacag ctagcagatc tcttccctcc tgctcccagc    5880
gcacacaaac ccgccctccc cttggtgttg gcggtccctg tggccttcac tttgttcact    5940
acctgtcagc ccagcctggg tgcacagtag ctgcaactcc ccattggtgc tacctggctc    6000
tcctgtctct gcagctctac aggtgaggcc cagcagaggg agtagggctc gccatgtttc    6060
tggtgagcca atttggctga tcttgggtgt ctgaacagct attgggtcca ccccagtccc    6120
tttcagctgc tgcttaatgc cctgctctct ccctggccca ccttatagag agcccaaaga    6180
gctcctgtaa gagggagaac tctatctgtg gtttataatc ttgcacgagg caccagagtc    6240
tccctgggtc ttgtgatgaa ctacatttat ccccttttcct gccccaacca caaactcttt    6300
ccttcaaaga gggcctgcct ggctccctcc acccaactgc acccatgaga ctcggtccaa    6360
gagtccattc cccaggtggg agccaactgt cagggaggtc tttcccacca acatctttc    6420 agctgctggg aggtgaccat agggctctgc ttttaaagat atggctgctt caaaggccag    6480
agtcacagga aggacttctt ccagggagat tagtggtgat ggagaggaga gttaaaatga    6540
cctcatgtcc ttcttgtcca cggttttgtt gagttttcac tcttctaatg caagggtctc    6600
acactgtgaa ccacttagga tgtgatcact ttcaggtggc caggaatgtt gaatgtctttt    6660 ggctcagttc atttaaaaaa gatatctatt tgaaagttct cagagttgta catatgtttc    6720
acagtacagg atctgtacat aaaagtttct ttcctaaacc attcaccaag agccaatatc    6780
taggcatttt cttggtagca caaattttct tattgcttag aaaattgtcc tccttgttat    6840
ttctgtttgt aagacttaag tgagttaggt ctttaaggaa agcaacgctc ctctgaaatg    6900
cttgtctttt ttctgttgcc gaaatagctg gtcctttttc gggagttaga tgtatagagt    6960
gtttgtatgt aaacatttct tgtaggcatc accatgaaca aagatatatt ttctatttat    7020
ttattatatg tgcacttcaa gaagtcactg tcagagaaat aaagaattgt cttaaatgtc    7080
```

<210> SEQ ID NO 89
<211> LENGTH: 1515
<212> TYPE: DNA
<213> ORGANISM: Homo sapiens

<400> SEQUENCE: 89

```
ggctcgggag agaccttgga gcgcgcggga aagagaccaa tataaactgt ggcgggatag      60
ttttcgggtc cttgtccagt gaaacaccct cggctgggaa gtcagttcgt tctctcctct     120
cctctcttct tgtttgaaca tggtgcggac taaagcagac agtgttccag gcacttacag     180
aaaagtggtg gctgctcgag cccccagaaa ggtgcttggg tcttccacct ctgccactaa     240
ttcgacatca gtttcatcga ggaaagctga aaataaatat gcaggaggga accccgtttg     300
```

-continued

| | |
|---|---|
| cgtgcgccca actcccaagt ggcaaaaagg aattggagaa ttctttaggt tgtcccctaa | 360 |
| agattctgaa aaagagaatc agattcctga agaggcagga agcagtggct taggaaaagc | 420 |
| aaagagaaaa gcatgtcctt tgcaacctga tcacacaaat gatgaaaaag aatagaactt | 480 |
| tctcattcat ctttgaataa cgtctccttg tttaccctgg tattctagaa tgtaaattta | 540 |
| cataaatgtg tttgttccaa ttagctttgt tgaacaggca tttaattaaa aaatttaggt | 600 |
| ttaaatttag atgttcaaaa gtagttgtga aatttgagaa tttgtaagac taattatggt | 660 |
| aacttagctt agtattcaat ataatgcatt gtttggtttc ttttaccaaa ttaagtgtct | 720 |
| agttcttgct aaaatcaagt cattgcattg tgttctaatt acaagtatgt tgtatttgag | 780 |
| atttgcttag attgttgtac tgctgccatt tttattggtg tttgattatt ggaatggtgc | 840 |
| catattgtca ctccttctac ttgctttaaa aagcagagtt agatttttgc acattaaaaa | 900 |
| attcagtatt aattaaacat tacttattct accctctttt ttggcaagga ggacaaatac | 960 |
| gcaatgttgg aaaaccttgg atggatatct tctctttaaa aaaatgtaaa gataatttgg | 1020 |
| tcttgagggt ttaaacggtt gataatgcct ctacaacaac aagaaaaaag ataaaatact | 1080 |
| aggatagaat catggtgggc acagtggctt ctcaggaggc tgaggaggga ggtttgcttg | 1140 |
| agtccaggag ttggagacca gcccaggcaa catagcgtaa accctatctc taaaacaatt | 1200 |
| tttagccggg tgcggtggct cacgcctgta atcccagcac tctgggaggc cgaggcgggt | 1260 |
| ggatcatgag gtcaggagat cgagaccatc ctgcctaaca aggtgaaacc ccgtctctac | 1320 |
| taaaaataca aaaaattagc cgggcgcggt ggcgggcgcc tgtagtccca gctactcggg | 1380 |
| aggctgaggc aggagaatgg cgtgaacccg ggaagtggag cttgcagtga gccgagattg | 1440 |
| cgccactgca gtcggcagtc cggcttgggc gacagagcga gactccgtct caaaaaaaaa | 1500 |
| aaaaaaaaaa aaaaa | 1515 |

<210> SEQ ID NO 90
<211> LENGTH: 1774
<212> TYPE: DNA
<213> ORGANISM: Homo sapiens

<400> SEQUENCE: 90

| | |
|---|---|
| agtactgaaa ttaagcagca tccaacacag gcctactctt acgacatgtg actttactgt | 60 |
| tttccgtttt tgttgaaaga gtcattaaca gttaggagtt gatggcagtt tcaataacag | 120 |
| gtcattgccg agaaaaggat agcactataa tatgcagaaa tctacaaatt ctgatacttc | 180 |
| cgtggaaaca ctgaattcta cccgccaagg cacaggagct gtgcaaatga gatcaaaaa | 240 |
| tgccaacagc caccatgaca ggctcagcca agtaaatcc atgatcctca ccgatgtcgg | 300 |
| gaaggtcact gaacctatat ccagacacag aaggaatcat tcacagcata tcttgaaaga | 360 |
| tgtcattcct ccattggaac aactgatggt tgaaaagaa ggttatctgc aaaaagctaa | 420 |
| aattgcagat ggaggaaaga aactaaggaa aaactggtct acttcctgga ttgttctttc | 480 |
| tagtcgaaga attgaatttt acaaagaatc caagcaacag gctctgtcca atatgaaaac | 540 |
| tgggcacaaa ccagaaagtg tggatttgtg tggagcacac attgaatggg ccaaggaaaa | 600 |
| atcgagcaga aagaatgtct ttcagatcac aacagtatca ggaaatgagt tccttctaca | 660 |
| gtcagatatt gacttcatca tattggattg gttccacgct atcaaaaatg caattgacag | 720 |
| attgccaaag gattcaagtt gtccatcaag aaacctggaa ttattcaaaa tccaaagatc | 780 |
| ctctagcact gaattgctaa gtcactacga cagtgatata aagaacaga aaccagagca | 840 |

| | |
|---|---|
| cagaaaatct ttaatgttca gactgcatca cagtgcttcc gatacaagcg acaaaaatcg | 900 |
| agttaaaagc agattaaaga agtttattac ccgaagacct tccctgaaaa ctctgcaaga | 960 |
| aaaaggactt attaaagatc aaattttttgg ctctcatctg cacaaagtgt gtgaacgtga | 1020 |
| aaattccaca gttccgtggt ttgtaaagca atgcattgaa gctgttgaga aaagaggtct | 1080 |
| agatgttgat ggaatatatc gagttagtgg caatctggca acaatacaga agttaagatt | 1140 |
| tattgtcaac caagaagaga agctgaattt ggacgacagc cagtgggagg acatccacgt | 1200 |
| tgtcaccgga gcactgaaga tgttttttccg ggagctgcct gagccgctct tcccttacag | 1260 |
| tttctttgag cagtttgtgg aagcgatcaa aaagcaagac aacaacacaa gaattgaagc | 1320 |
| tgtaaaatct cttgtacaaa aactccctcc gccaaatcgt gacaccatga aagtcctctt | 1380 |
| tggacatcta actaagatag tggccaaagc ctccaagaac ctcatgtcca cgcaaagctt | 1440 |
| ggggattgta tttggaccta cccttctgcg agctgaaaat gaaacaggaa acatggcgat | 1500 |
| ccacatggtc taccagaacc agatagctga gctcatgctg agtgagtaca gtaagatctt | 1560 |
| cggctcagag gaagactgac agacaagaca agctactgaa tacgttcaca tctgtcttga | 1620 |
| tgcctaatat ttttacattt ctgtaaacat atttctgaaa tattttttgc ctttcaagcg | 1680 |
| acagatgcct cattttgtga aaacttaatg atgattttgt gtttaagttc caaacatttg | 1740 |
| aataaaataa ttgacaataa aaaaaaaaaa aaaa | 1774 |

<210> SEQ ID NO 91
<211> LENGTH: 2707
<212> TYPE: DNA
<213> ORGANISM: Homo sapiens

<400> SEQUENCE: 91

| | |
|---|---|
| gtatgctgct gctgccgggt gtccatggcc cgcaccccca agctgccact gcagcagtca | 60 |
| gagtggcagc tgaaggctcg gttcatgccg tgcccccggg cagttctggt gaggctaagc | 120 |
| aagaggcctc tgcatcttga cacctaggag agcaggacg gagtctccca gggtggagga | 180 |
| ccatgctgcg ccgcaagccc tccaatgcca gtgagaagga gcccactcag aagaaaaagc | 240 |
| tctcccttca gcgctccagc agcttcaagg attttgccaa atccaaaccc agctcccccg | 300 |
| tggtgagcga gaaggagttt aatctggatg ataacattcc agaagatgac tcaggtgtcc | 360 |
| ccaccccaga agatgctggg aagagtggca aaaagctggg gaagaagtgg agggcagtga | 420 |
| tttcccgaac catgaacagg aagatgggca agatgatggt gaaggccctg tcagaagaga | 480 |
| tgcagacac tctggaggag ggctctgcct ccccgacatc tccagactac agcctggaca | 540 |
| gccctggccc tgagaagatg gcgctggcct tttctgagca agaggagcat gaacttccgg | 600 |
| tgctcagccg ccaggcatca acaggcagtg agctctgcag ccccagccca ggttctggca | 660 |
| gcttcgggga ggaaccacct gccccccagt acacagggcc tttctgtggc cgggcacgag | 720 |
| tccacaccga cttcactccc agccctatg accacgactc gctgaaactg cagaaaggag | 780 |
| atgtgatcca gatcattgaa aagccacctg tgggcacgtg gctggcccta ctcaatggca | 840 |
| aggtgggctc tttcaaattc atctatgtgg atgtgctgcc cgaggaggcc gtggggcatg | 900 |
| cccgccccag ccgccgacag agcaagggca agaggcccaa gctaagacc ctgcatgagc | 960 |
| tgctggagcg catcggcctg gaggagcaca atccaccct cctgctcaat ggctaccaga | 1020 |
| cactggaaga cttcaaagag ctgcgagaaa cacacctcaa tgagctgaac atcatggatc | 1080 |
| cacagcaccg ggccaagctg ctcacggccg ccgagctgct gctggactat gacactggca | 1140 |
| gtgaggaggc tgaagagggc gccgagagca gccaggagcc agtggcacac acagtgtcgg | 1200 |

```
aacccaaggt ggacatcccg cgcgactcag gctgctttga gggctcggag agcgggcgcg    1260
atgacgcaga gctggcaggc actgaggagc agctgcaagg cctctccctg gccgggcac    1320 cttgaggtgg cggtggcaat aggccaaggc tgggacccag ctgcaaaggc tgtaggagtg    1380
ggcccagcct cccgtggtgg cccaggtcct gaggactggc actgagcctg gccctgcttc    1440
cccagggaca cttagggcca cagaggccag gccagggccc tacaggttcc aggctcagct    1500
ggagtggttg gggagtcgcc caagggcaca tcccacctgc ctgagcccg ccctccacca     1560 gcgactgaca gcgcagcccc tcctggcacc aactgctccc ctgccatggc cacggccaca    1620
gcaagtgggg cactgggaaa ccctgcccat gtccctcacc aacaaggcct ccaaatcctc    1680
ctcaccccca caccacctac ccctgtcgca ctgctcctga aaagggggcc aagtcaatgt    1740
ttcaggtcag tctaaaaacc ctagggaagc tggccattta aaagaaccca aactgaccat    1800
gggtaaatcc agttcccta aataaggcct gaagaaatcc acaggtacca ttcccacttt     1860
ccttctccct agctttctta gaggtttggc cactaaatct tatgagactt gaaccaagtg    1920
gcttcctctt tctaggctta ggacggggttg gggttagaaa gggtgatcac tgaaggcctt   1980
gcctgctctg acattctgtg acattaaatg tctattctcc tgttacctgt ggcctgggac    2040
accagtgggg tttatcgagg ggaccagagg ggcctcaggc tttcagatga aatggctcct    2100
cctactcacc cactttattc ctctccatgt aattcaggac aagctgcaac ttcccccagc    2160
ttaacacaat gcccatacct catacgatat gcgccctccc gttccatccc tggcccctc    2220 aaacgagact tctcacaagg ctgattacag atggtcaaac ctggcttcca aggacagaat    2280
tgcctctcgg aagccagctg tggatctgag tccagagttg gccacttgtg tgggtcctca    2340
caagcaaaga gagcactaaa cttgacattg ggggtccacc actccaactt tgctttctga    2400
aggttttggt gtacattgag ccccagaagg aaaggagagt atctgtgagt gggggcctcc    2460 cttgaccca gtacgaagtc tatgccctga atccccagag tagcccttcc tggtgcccaa     2520
ctggcctggg gacaaacagc gtccactaca tctaggactg ccggctaagt ggacacactt    2580
cttgacctcc taccaggaac tttggtaaaa gctagctttg gggaaggggt tgggtgtaaa    2640
tatgagaggg tggagggaga ccagctggta gcaataaaca tgggtagaac taaaaaaaaa    2700
aaaaaaa                                                              2707
```